United States Patent
Johnson et al.

(10) Patent No.: US 12,168,004 B2
(45) Date of Patent: *Dec. 17, 2024

(54) TREATMENT OF MIGRAINE

(71) Applicant: Merck Sharp & Dohme LLC, Rahway, NJ (US)

(72) Inventors: Mary Ann Johnson, Norristown, PA (US); Leonardo Resende Allain, Lansdale, PA (US); W. Mark Eickhoff, Lansdale, PA (US); Craig B. Ikeda, Harleysville, PA (US); Chad D. Brown, Quakertown, PA (US); Francis J. Flanagan, Jr., North Wales, PA (US); Rebecca Nofsinger, Lansdale, PA (US); Melanie J. Marota, Mount Laurel, NJ (US); Lisa Lupton, South San Francisco, CA (US); Paresh B. Patel, Langhome, PA (US); Hanmi Xi, Furlong, PA (US); Wei Xu, North Wales, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,025

(22) Filed: May 13, 2024

(65) Prior Publication Data

US 2024/0299369 A1    Sep. 12, 2024

Related U.S. Application Data

(60) Division of application No. 18/440,217, filed on Feb. 13, 2024, which is a continuation-in-part of application No. 18/523,481, filed on Nov. 29, 2023, which is a continuation of application No. 18/210,719, filed on Jun. 16, 2023, now Pat. No. 11,857,542, which is a continuation of application No. 17/559,177, filed on Dec. 22, 2021, now Pat. No. 11,717,515, said application No. 18/440,217 is a continuation-in-part of application No. 18/137,925, filed on Apr. 21, 2023, which is a continuation of application No. 17/110,398, filed on Dec. 3, 2020, now Pat. No. 11,925,709, which is a continuation of application No. 16/178,641, filed on Nov. 2, 2018, now abandoned, which is a continuation of application No. 15/115,026, filed as application No. PCT/US2015/013672 on Jan. 30, 2015, now Pat. No. 10,117,836.

(60) Provisional application No. 63/129,379, filed on Dec. 22, 2020, provisional application No. 61/936,019, filed on Feb. 5, 2014, provisional application No. 62/087,366, filed on Dec. 4, 2014.

(51) Int. Cl.
 A61K 31/4375    (2006.01)
 A61K 31/4545    (2006.01)
 A61P 25/06      (2006.01)

(52) U.S. Cl.
 CPC ...... *A61K 31/4375* (2013.01); *A61K 31/4545* (2013.01); *A61P 25/06* (2018.01)

(58) Field of Classification Search
 CPC .. A61K 31/4375; A61K 31/4545; A61P 25/06
 See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 7,205,293 B2 | 4/2007 | Bell et al. | |
| 7,390,798 B2 | 6/2008 | Williams et al. | |
| 7,629,338 B2 | 12/2009 | Wood | |
| 7,893,079 B2 | 2/2011 | Wood et al. | |
| 8,481,556 B2 | 7/2013 | Bell et al. | |
| 8,754,096 B2 | 6/2014 | Bell et al. | |
| 8,883,807 B2 | 11/2014 | Bell et al. | |
| 8,895,572 B2 | 11/2014 | Burgey et al. | |
| 8,912,210 B2 | 12/2014 | Bell et al. | |
| 9,067,941 B2 | 6/2015 | Burgey et al. | |
| 9,109,209 B2 | 8/2015 | Cabirol et al. | |
| 9,174,989 B2 | 11/2015 | Chen et al. | |
| 9,227,972 B2 | 1/2016 | Bell et al. | |
| 9,227,973 B2 | 1/2016 | Bell et al. | |
| 9,296,750 B2 | 3/2016 | Bell et al. | |
| 9,376,431 B2 | 6/2016 | Xiang et al. | |

(Continued)

FOREIGN PATENT DOCUMENTS

| | | |
|---|---|---|
| CN | 101018781 A | 8/2007 |
| CN | 101208303 A | 6/2008 |

(Continued)

OTHER PUBLICATIONS

Tepper, "Anti-Calcitonin Gene-Related Peptide (CGRP) Therapies: Update on a Previous Review After the American Headache Society 60th Scientific Meeting, San Francisco, Jun. 11, 2018," Headache 58.7 (2018): 276-290.

Israel et al., "CGRP Monoclonal Antibodies for the Preventative Treatment of Migraine," Current Pain and Headache Reports 22.5 (2018): 1-6.

Meglio, "Dose-Dependent Weight Reductions Observed With Atogepant", Neurology Live, Jun. 15, 2022 . . . .

(Continued)

*Primary Examiner* — Timothy R Rozof
(74) *Attorney, Agent, or Firm* — Foley Hoag LLP; Hathaway P. Russell; Benjamin A. Vaughan

(57) ABSTRACT

The present disclosure provides methods for the acute treatment of migraine with or without aura, comprising the administration of ubrogepant. In particular, the present disclosure provides methods for the acute treatment of migraine in patients having hepatic impairment; in patients with renal impairment; and in patients concurrently taking CYP3A4 modulators or BCRP and/or P-gp only inhibitors.

30 Claims, 12 Drawing Sheets

(56) References Cited

U.S. PATENT DOCUMENTS

| | | | |
|---|---|---|---|
| 9,409,916 | B2 | 8/2016 | Bell et al. |
| 9,487,523 | B2 | 11/2016 | Belyk et al. |
| 9,499,541 | B2 | 11/2016 | Bell et al. |
| 9,499,545 | B2 | 11/2016 | Bell et al. |
| 9,624,478 | B2 | 4/2017 | Cabirol et al. |
| 9,833,448 | B2 | 12/2017 | Bell et al. |
| 9,833,488 | B2 | 12/2017 | Buyuktimkin et al. |
| 9,850,246 | B2 | 12/2017 | Chen et al. |
| 10,106,541 | B2 | 10/2018 | Chen et al. |
| 10,117,836 | B2 | 11/2018 | Johnson et al. |
| 10,117,936 | B2 | 11/2018 | Nebuloni et al. |
| 10,272,077 | B2 | 4/2019 | Bell et al. |
| 11,717,515 | B2 | 8/2023 | Trugman et al. |
| 11,857,542 | B2 | 1/2024 | Trugman et al. |
| 11,925,709 | B2 | 3/2024 | Johnson et al. |
| 2004/0076668 | A1 | 4/2004 | Berchielli et al. |
| 2005/0196439 | A1 | 9/2005 | Sherwood et al. |
| 2010/0179166 | A1 | 7/2010 | Bell et al. |
| 2010/0227903 | A1 | 9/2010 | Geers et al. |
| 2012/0122899 | A1 | 5/2012 | Bell et al. |
| 2012/0122900 | A1 | 5/2012 | Bell et al. |
| 2012/0122911 | A1 | 5/2012 | Bell et al. |
| 2015/0023888 | A1 | 1/2015 | Cook et al. |
| 2016/0051561 | A1 | 2/2016 | Etter |
| 2016/0220552 | A1 | 8/2016 | Mahjour et al. |
| 2016/0346214 | A1 | 12/2016 | Johnson et al. |
| 2017/0027925 | A1 | 2/2017 | Bell et al. |
| 2017/0189443 | A1 | 7/2017 | Parsons |
| 2018/0008576 | A1 | 1/2018 | Kleideiter et al. |
| 2018/0092899 | A1 | 4/2018 | Liu et al. |
| 2018/0127417 | A1 | 5/2018 | Chen et al. |
| 2019/0070161 | A1 | 3/2019 | Mahjour et al. |
| 2019/0085061 | A1 | 3/2019 | Burstein |
| 2019/0135927 | A1 | 5/2019 | Levin |
| 2019/0209478 | A1 | 7/2019 | Johnson et al. |
| 2019/0374518 | A1 | 12/2019 | Trugman et al. |
| 2019/0374520 | A1 | 12/2019 | Trugman et al. |
| 2020/0383983 | A1 | 12/2020 | Brin et al. |
| 2021/0085612 | A1 | 3/2021 | Johnson et al. |
| 2021/0379029 | A1 | 12/2021 | Trugman et al. |
| 2022/0031686 | A1 | 2/2022 | Trugman et al. |
| 2022/0193051 | A1 | 6/2022 | Trugman et al. |
| 2022/0340650 | A1 | 10/2022 | Jakate et al. |
| 2023/0130736 | A1 | 4/2023 | Boinpally et al. |
| 2023/0158128 | A1 | 5/2023 | Brin et al. |
| 2023/0248655 | A1 | 8/2023 | Johnson et al. |
| 2023/0248715 | A1 | 8/2023 | Liu et al. |
| 2023/0321055 | A1 | 10/2023 | Trugman et al. |
| 2023/0330072 | A1 | 10/2023 | Trugman et al. |
| 2024/0100029 | A1 | 3/2024 | Trugman et al. |

FOREIGN PATENT DOCUMENTS

| | | |
|---|---|---|
| CN | 101448821 B | 3/2013 |
| JP | 2008/512480 A | 4/2008 |
| JP | 2008/512481 A | 4/2008 |
| JP | 2010/529119 A | 8/2010 |
| JP | 2011/504481 A | 2/2011 |
| JP | 2012/528827 A | 11/2012 |
| KR | 10-2013-0087037 A | 8/2013 |
| RU | 2216317 C2 | 11/2003 |
| WO | WO-2004/082602 A2 | 9/2004 |
| WO | WO-2004/092166 A2 | 10/2004 |
| WO | WO-2004/092168 A1 | 10/2004 |
| WO | WO-2006/031606 A2 | 3/2006 |
| WO | WO-2006/031610 A2 | 3/2006 |
| WO | WO-2006/069754 A1 | 7/2006 |
| WO | WO-2007/092642 A2 | 8/2007 |
| WO | WO-2007/133491 A1 | 11/2007 |
| WO | WO-2008/153849 A1 | 12/2008 |
| WO | WO-2009/050234 A1 | 4/2009 |
| WO | WO-2009/065922 A2 | 5/2009 |
| WO | WO-2009/100090 A1 | 8/2009 |
| WO | WO-2009/126530 A2 | 10/2009 |
| WO | WO-2010/114801 A1 | 10/2010 |
| WO | WO-2010/139717 A1 | 12/2010 |
| WO | WO-2011/156578 A1 | 12/2011 |
| WO | WO-2012/064910 A1 | 5/2012 |
| WO | WO-2012/121758 A1 | 9/2012 |
| WO | WO-2012/122279 A1 | 9/2012 |
| WO | WO-2015/038736 A2 | 3/2015 |
| WO | WO-2015/119848 A1 | 8/2015 |
| WO | WO-2015/120014 A1 | 8/2015 |
| WO | WO-2017/051385 A1 | 3/2017 |
| WO | WO-2019/050759 A1 | 3/2019 |
| WO | WO-2019/087161 A1 | 5/2019 |
| WO | WO-2019/234709 A1 | 12/2019 |
| WO | WO-2019/234710 A1 | 12/2019 |
| WO | WO-2020/051137 A1 | 3/2020 |
| WO | WO-2020/150703 A1 | 7/2020 |
| WO | WO-2020/214906 A1 | 10/2020 |
| WO | WO-2021/062282 A1 | 4/2021 |
| WO | WO-2022/140537 A1 | 6/2022 |
| WO | WO-2023/049920 A1 | 3/2023 |
| WO | WO-2023/173005 A2 | 9/2023 |
| WO | WO-2024/081718 A1 | 4/2024 |

OTHER PUBLICATIONS

Supplementary European Search Report for EP Application No. 21850713.5 dated Jun. 26, 2024.

"61st Annual Scientific Meeting", American Headache Society, 208 pages, (Jul. 11-14, 2019).

"Pharmacokinetics in Patients with Impaired Hepatic Function: Study Design, Data Analysis, and Impact on Dosing and Labeling," U.S. Food and Drug Administration (2003).

60th Annual Scientific Meeting, American Headache Society, 60th Annual Scientific Meeting American Headache Society, AHS 2018. San Francisco, CA, United States. Jun. 28-Jul. 1, 2018.

Ailani et al., "An optional second dose of ubrogepant is effective in achieving 2-hour pain freedom in the acute treatment of migraine (166)", Neurology, 94(15), (2020).

Ailani et al., "Atogepant for the Preventive Treatment of Migraine" The New England Journal of Medicine, vol. 385, No. 8, pp. 695-706 (2021).

Allergan plc. (Nov. 5, 2015), "Allergan Outlines Open Science Model and Highlights Key Development Programs at R&D Day, Press Release." Retrieved from the Internet: http://www/multivu.com/players/English/7671931-allergan-r-d-day/, (Allergan plc, 2015), 5 pages.

Amerge (naratriptan hydrochloride) tablets, Highlights of Prescribing Information (2016).

American Headache Society (Jun. 9, 2016), Clinical Data Presented at American Headache Society Meeting Shows Promise of New Treatments for Migraine Prevention [Press Release]. Retrieved from the Internet: (https://americanheadachesociety.org/news/clinical-data-presented-at-american-headache-society-meeting-shows-promise-of-new-treatments-for-migraine-prevention/), 5 pages.

Anonymous., "Handbook of Pharmaceutical Excipients," 5th Edition, Pharmaceutical Press, 2006, 10 pages.

Anonymous., "Sample Preparation of Pharmaceutical Dosage Forms," Springer, 2011, 5 pages.

Anonymous: "Highlights of Prescribing Information: Qulipta", retrieved online via <https://www.rxabbvie.com/pdf/qulipta_pi.pdf> (2021).

Anonymous: "Highlights of Prescribing Information: Ubrelvy (ubrogepant) tablets," retrieved online via <https://www.rxabbvie.com/pdf/ubrelvY-P i.pdf> (2021).

Ansel C.H., et al., "Pharmaceutical Dosage Forms and Drug Delivery Systems", 7th Edition, Lippincott Williams & Wilkins, 1999, pp. 367-369.

Armstrong., "Biohaven hopes to give Allergan a headache," Evaluate Vantage, retrieved online <https://www.evaluate.com/vantage/articles/interviews/biohaven-hopes-give-allergan-headache>: 3 pages (2018).

Arulmozhi et al., "Migraine: Current concepts and emerging therapies", Vascular Pharmacology, 43: 176-187 (2005).

Ashina et al. "Plasma levels of calcitonin gene-related peptide in chronic tension-type headache," Neurology 55.9: 1335-1340. (2000).

(56) References Cited

OTHER PUBLICATIONS

Awawdeh et al. "Quantitative analysis of substance P, neurokinin A and calcitonin gene related peptide in pulp tissue from painful and healthy human teeth," International endodontic Journal 35.1 : 30-36 (2002).
Bagley C.L., et al., "Validating Migraine-Specific Quality of Life Questionnaire v2.1 in Episodic and Chronic Migraine," Headache, Mar. 2012; vol. 5 2(3): pp. 409-421.
Barbanti et al., "The role of anti-CGRP antibodies in the pathophysiology of primary headaches," Neurol Sci 38 (Suppl. 1): pp. S31-S35 (2017).
Beer et al. "Systemic neuropeptide levels as predictive indicators for lethal outcome in patients with postoperative sepsis," Critical care medicine 30.8 : 1794-1798 (2002).
Belikov., "Pharmaceutical Chemistry," M. High School: 6 pages (1993).
Bell et al., MEDI 20: Discovery of AGN-241689: A potent, orally-acting CGRP receptor antagonist for migraine prophylaxis, 253 American Chemical Society, Abstracts, p. 20 (Apr. 2-6, 2017) (Year: 2017).
Bellamy et al. "Salivary levels of CGRP and VIP in rhinosinusitis and migraine patients," Headache: The Journal of Head and Face Pain 46.1 : 24-33(2006).
Bennet et al. "Alleviation of mechanical and thermal allodynia by CGRP8-37 in a rodent model of chronic central pain," Pain 86.1-2 : 163-175 (2000).
Bigal M.E., et al., "Body mass index and episodic headaches: a population-based study," Archives of internal medicine, Oct. 2007, vol. 167 (18), pp. 1964-1970.
Bigal M.E., et al., "Obesity and migraine: a population study," Neurology, 2006, vol. 66(4), pp. 545-550.
Boinpally et al., "63rd Annual Scientific Meeting American Headache Society: Evaluation of the pharmacokinetic interaction and safety of atogepant coadministered with esomeprazole magnesium", Headache 61 (S1): pp. 1-178 (2021).
Boinpally et al., "Single-Dose Pharmacokinetics and Safety of Atogepant in Adults With Hepatic Impairment: Results From an Open-Label, Phase 1 Trial," Clinical Pharmacology in Drug Development 10(7): pp. 726-733 (2021).
Boinpally et al., "Single-Dose Pharmacokinetics and Safety of Ubrogepant in Adults With Hepatic Impairment: Results From an Open-Label, Phase 1 Trial," Clinical Pharmacology in Drug Development, 0(0): 1-8 (2022).
Brauser, D., "Phase 3 Strive and Arise Trials Show Efficacy, Safety for Erenumab in Migraine Prevention," Medscape Medical News, 2017.
Burstein et al. "An association between migraine and cutaneous allodynia," Annals of neurology 47.5 614-624. (2000).
Cady et al. "Elevated saliva calcitonin gene-related peptide levels during acute migraine predict therapeutic response to rizatriptan," Headache: The Journal of Head and Face Pain 49.9: 1258-1266. (2009).
Cala M.L., et al., "The Activity Impairment in Migraine Diary (AIM-D): A novel migraine-specific patient-reported outcome measure to assess functioning based on activity impairment in episodic and chronic migraine patients", MTIS2018-005, Cephalalgia, 2018, vol. 38, pp. 1-115.
Chedid et al., "Hepatocellular Carcinoma: Diagnosis and Operative Management," ABCD Arq Bras Cir Dig 30(4): pp. 272-278 (2017).
Chen et al. "Menopausal flushes and calcitonin-gene-related peptide," The Lancet 342.8862 :p. 49.(1993).
Cheng et al. "The concentration of inhibitor which causes 50 percent inhibition (I) of an enzymatic reaction," Biochem. Pharmacol 22 : 3099-3108 (1973).
CHMP Guideline, "Guideline on the evaluation of the pharmacokinetics of medicinal products in patients with decreased renal function", European Medicines Agency, 15 pages, (2015).
Cho et al. "Development of Novel Fast-Dissolving Tacrolimus Solid Dispersion-Loaded Prolonged Release Tablet". European Journal of Pharmaceutical Sciences. Jan. 2014 [Online], 4:1-7. (Year: 2014).
Clinical Trial NCT02828020: Efficacy, Safety, and Tolerability Study of Oral Ubrogepant in the Acute Treatment of Migraine (Achieve I), https://clinicaltrials.gov/ct2/history/NCT02828020?V_1=View#StudyPageTop (2016).
Clinical Trial NCT02848326: Efficacy, Safety, and Tolerability of Multiple Dosing Regimens of Oral Atogepant (AGN-241689) in Episodic Migraine Prevention, https://clinicaltrials.gov/ct2/show/NCT02848326 (2016).
Clinical Trial NCT02867709: Efficacy, Safety, and Tolerability of Oral Ubrogepant in the Acute Treatment of Migraine (Achieve II), https://clinicaltrials.gov/ct2/show/results/NCT02867709 (2016).
Clinical Trial NCT03700320: Study to Evaluate the Safety and Tolerability of Treatment With Atogepant 60 mg Daily for the Prevention of Migraine in Participants With Episodic Migraine, https://clinicaltrials.gov/ct2/show/NCT03700320 (2018).
Clinical Trial NCT03777059: 12-Week Placebo-controlled Study of Atogepant for the Preventive Treatment of Migraine in Participants With Episodic Migraine, https://www.clinicaltrials.gov/ct2/show/NCT03777059 (2018).
Connor et al., "Randomized, controlled trial of telcagepant for the acute treatment of migraine", Neurology, 2009, pp. 970-977, 73.
Curto et al., "Ubrogepant for the treatment of migraine." Expert Opinion on Pharmacotherapy 21(7) (2020): 755-759.
Dahlof CGH. "Infrequent or non-response to oral sumatriptan does not predict response to other triptans—review of four trials," Cephalagia, Feb. 2006, vol. 26 (2), pp. 98-106.
Deen et al. "Blocking CGRP in migraine patients—a review of pros and cons," The Journal of Headache and Pain 18(96): 9 pages (2017).
Delay-Goyet et al. "Relative involvement oi substance P and CGRP mechanisms in antidromic vasodilation in the rat skin," Acta physiologica scandinavica 146.4 : 537-538.(1992).
Do et al., "Therapeutic novelties in migraine: new drugs, new hope?," The Journal of Headache and Pain, 20: Article 37 pp. 1-13 (2019).
Dodick et al., "Ubrogepant Achieves Onset of Pain Relief at 1 Hour for the Acute Treatment of Migraine (1223)", Neurology, 94(15), (2020).
Dodick et al., "Ubrogepant for the Acute Treatment of Migraine When Administered During the Prodrome (Premonitory Phase): Results From a Phase 3, Randomized, Double-blind, Placebo-Controlled, Crossover Study (S47. 001)." Neurology, (100)17 (2023).
Dodick et al., "Ubrogepant for the treatment of migraine", *New England Journal of Medicine* 381.23: 2230-2241 (2019).
Doods "Development of CGRP antagonists for the treatment of migraine," Current opinion in investigational Drugs 2.9: 1261-1268. (2001).
Doods et al. "Pharmacological profile of BIBN4096BS, the first selective small molecule CGRP antaaonist," British Journal of Pharmacology 29.3 : 420-423. (2000).
Dos Santos et al., "Small molecule CGRP receptor antagonists for the preventive treatment of migraine: a review." European Journal of Pharmacology 922 (2022): 174902.
Edvinsson et al. "Characterization of the effects of a non-peptide CGRP receptor antagonist in SK-N-MC cells and isolated human cerebral arteries," European journal of pharmacology 415. : 39-44. (2001).
Edvinsson et al., "Basic mechanisms of migraine and its acute treatment", Pharmacology and Therapeutics, 136: 319-333 (2012).
Edvinsson et al., "CGRP as the target of new migrainetherapies—successful translation from bench to clinic", Nature Reviews, 14: 338-350 (2018).
Edvinsson et al., "Neuropeptides in Migraine and Cluster Headache Review Article", Cephalalgia, Oct. 14, 1994 (Oct. 14, 1994), pp. 320-327, XP055542226.
Escott et al. "Trigeminal ganglion stimulation increases facial skin blood flow in the rat: a major role for calcitonin gene-related peptide," Brain research 669.i : 93-99 (1995).
Evans et al. "The asymmetric synthesis of. alpha.-amino acids. Electrophilic azidation of chiralimide enolates, a practical approach to the syntheses of (R) and (S)-alpha azido carboxylic acids," Journal of the American Chemical Society 112.10 : 4011-4030. (1990).

(56) References Cited

OTHER PUBLICATIONS

Extended European Search Report for EP Application No. 20869848.0 dated Dec. 22, 2023.
Fierce Biotech, "Merck kills Phill migraine drug program" (Jul. 29, 2011), available at <https://www.fiercebiotech.com/biotech/merck-kills-phiii-migraine-drug-program>.
Food and Drug Administration, "The Impact of Renal Impairment on Patient Drug Response Assessing the Need for a Consensus Approach", Pharmaceutical Science and Clinical Pharmacology Advisory Committee Meeting, (2019).
Foster et al. "Calcitonin gene-related peptide is chemotactic for human T lymphocytes," Annals of the New York Academy of Sciences 657.1 : 397-404. (1992).
Friesen et al., "Hydroxypropyl Methylcellulose Acetate Succinate-Based Spray-Dried Dispersions: An Overview," Molecular Pharmaceutics, 5(6): 1003-1019 (2008).
Gelaye B., et al., "Body composition status and the risk of migraine: a meta-analysis," Neurology, May 2017, vol. 88 (19), pp. 1795-1804.
Gennaro Alfonso R., "Remington: The Science and Practice of Pharmacy", 2000, 20th edition, Table of Contents.
Global Health Metrics, "Global burden of 369 diseases and injuries in 204 countries and territories, 1990-2019: a systematic analysis for the Global Burden of Disease Study 2019", The Lancet, 396 (10258), pp. 1204-1222.
Goadsby et al. "Release of vasoactive peptides in the extracerebral circulation of humans and the cat during activation of the trigerninovascular system," Annals of Neurology: Official Journal of the American Neurological Association and the Child Neurology Society 23.2 : 193-196 (1988).
Goadsby et al. "Vasoactive peptide release in the extracerebral circulation of humans during migraine headache," Annals of Neurology: Official Journal of the American Neurological Association and the Child Neurology Society 28.2 183-187. (1990).
Goadsby et al., "Efficacy of Ubrogepant for the Treatment of Migraine Symptoms During the Prodrome (Premonitory Phase): Results From the Prodrome Trial" (2023)., Neurology, [Online] pp. 1-6.
Goadsby et al., "Safety and tolerability of ubrogepant following intermittent, high-frequency dosing: randomized, placebo-controlled trial in healthy adults." Cephalalgia 39.14 (2019): 1753-1761.
Goadsby et al., "Safety, tolerability, and efficacy of orally administered atogepant for the prevention of episodic migraine in adults: a double-blind, randomised phase 2b/3 trail" (2020).
Goadsby, "Bench to bedside advances in the 21st century for primary headache disorders: migraine treatments for migraine patients," Brain 139(10): pp. 2571-2577 (2016).
Goodman & Gilman's The Pharmacological Basis of Therapeutics, Joel G. Hardman et al., eds., McGraw-Hill Professional, 10th ed. 2001, Table of Contents.
Guo et al., "The Applications of Vitamin E TPGS in Drug Delivery," European Journal of Pharmaceutical Sciences, 49(2): 175-186 (2013).
Harmon et al. "Reaction of arylsulfonyl azides with N-methylindole," The Journal of Organic Chemistry, 38.1, 11-16 (1973).
Herzog et al. "CGRP receptors in the gerbil spiral modular artery mediate a sustained vasodilation via a transient cAMP-mediated Ca2+-decrease," The Journal of membrane biology 189.3, 225-236. (2002).
Hewitt et al., "Randomized controlled trial of the CGRP receptor antagonist MK-3207 in the acute treatment of migraine," Cephalalgia Apr. 2011; 31(6): 712-22.
Ho et al., "Efficacy and Tolerability of MK-097 (telcagepant), a new oral antagonist of cacitonin gene-related peptide receptor, compared with zoimitriptant for acute migraine; a randomised, placebo-controlled parallel-treatment trial":, vol. 372,pp. 2115-2123, The Lancet, 2008, pp. 2115-2123, 372.
Ho et al., "Randomized Controlled trial of an oral CGRP receptor antagonist, MK-0974, in acute treatment of migraine", Neurology, Apr. 15, 2008; 70 (16): 1304-12.
Ho et al., "Randomized Controlled Trial of the CGRP receptor antagonist telcagepant for migraine prevention", Neurology, Sep. 9, 2014; 83(11): 958-66.
Ho et al., "Randomized controlled trial of the CGRP receptor antagonist telcagepant for prevention of headache in women with perimenstrual migraine", Cephalalgia, Feb. 2016;36(2): 148-61.
Holland P.R., and Goadsby P.J., "Targeted CGRP Small Molecule Antagonists for Acute Migraine Therapy," Neurotherapeutics, Apr. 2018, vol. 15 (2), pp. 304-312.
Holzer et al., "Evaluation o Sodium Stearyl Fumarate as a Tablet Lubricant," International Journal of Pharmaceutics, 2(3-4): 145-153 (Abstract Only)(1979).
Hutchinson et al., "Ubrogepant for the Acute Treatment of Migraine: Pooled Safety and Tolerability From Achieve I and Achieve II Phase 3 Studies (117)", Neurology, 94(15), (2020).
IMITREX (sumatriptan) tablets, Highlights of Prescribing Information (2020).
International Preliminary Report on Patentability for International Application No. PCT/IB2019/054780 dated Dec. 8, 2020.
International Preliminary Report on Patentability for International Application No. PCT/US2015/013672 dated Aug. 9, 2016.
International Preliminary Report on Patentability for International Application No. PCT/US2020/028666 dated Oct. 28, 2021.
International Preliminary Report on Patentability for International Application No. PCT/US2021/043791 dated Nov. 18, 2021.
International Search Report and Written Opinion for International Application No. PCT/US23/76576 dated Feb. 23, 2024.
International Search Report and Written Opinion for International Application No. PCT/IB2019/054780, mailed on Oct. 28, 2019, 8 pages.
International Search Report and Written Opinion for International Application No. PCT/IB2019/054781, dated Oct. 22, 2019, 10 pages.
International Search Report and Written Opinion for International Application No. PCT/US15/13672 dated Apr. 21, 2015.
International Search Report and Written Opinion for International Application No. PCT/US2011/060081, dated Dec. 19, 2011.
International Search Report and Written Opinion for International Application No. PCT/US2020/028666 dated Aug. 28, 2020.
International Search Report and Written Opinion for International Application No. PCT/US2020/052891 dated Feb. 17, 2021.
International Search Report and Written Opinion for International Application No. PCT/US2021/064853 dated Mar. 18, 2022.
International Search Report and Written Opinion for International Application No. PCT/US2022/077061 dated Jan. 4, 2023.
International Search Report and Written Opinion for International Application No. PCT/US2023/064027 dated Sep. 26, 2023.
Jakate et al., "Effects of CYP3A4 and P-glycoprotein inhibition or induction on the pharmacokinetics of ubrogepant in healthy adults: Two phase 1, open-label, fixed-sequence, single-center, crossover trials," Cephalalgia Reports, 4: 1-10 (2021).
Johnson et al., "A pharmacogenomic evaluation of migraine therapy", Expert Opinion on Pharmacotherapy, 8: 1821-1835 (2007).
Kasarala G. et al., "Standard Liver Tests," Clinical Liver Disease, Jul. 2016, vol. 8 (1), pp. 13-18.
Kibbe, "Handbook of Pharmaceuticals Excipients", 2000, Pharmaceutical Press, XP002773202, p. 386.
Kielbasa et al., "A new era for migraine: pharmacokinetic and pharmacodynamic insights into monoclonal antibodies with a focus on galcanezumab, an anti-CGRP antibody", Cephalalgia 39.10: 1284-1297 (2019).
Kopruszinski et al., "Prevention of stress- or nitric oxide donor-induced medication overuse headache by a calcitonin gene-related peptide antibody in rodents," Cephalalgia, 37(6): 560-570 (2017).
Kristoffersen E.S., et al., "Migraine, Obesity, and Body Fat Distribution—a Population—Based Study," The journal of headache and pain, Aug. 2020, vol. 21 (1), pp. 97.
Lance "Headache Pathogenesis: Monoarnines," Neuropeptides, Purines & Nitric Oxide 3-9 (1997).
Lars Edvinsson: "CGRP as the target of new migraine therapies—successful translation from bench to clinic", Nature Reviews, Apr. 24, 2018 (Apr. 24, 2018). XP055476796.

(56) References Cited

OTHER PUBLICATIONS

Lassen et al. "CGRP may play a causative role in migraine," Cephalalgia 22.1 (2002): 54-61.

Late-Breaking Abstracts: 60th Annual Scientific Meeting, American Headache Society, 60th Annual Scientific Meeting American Headache Society, AHS 2018. San Francisco, CA, United States. Jun. 28-Jul. 1, 2018.

Li et al. "Effect of CGRP receptor antagonist CGRP8-37 on nociceptive response, NOS expression and NO content in the dorsal horn of spinal cord during formalin-induced inflammatory pain in rats," Chinese Journal of Applied Physiology. 20(3): 291-295. (2004).

Lipton et al., "Effect of ubrogepant vs placebo on pain and the most bothersome associated symptom in the acute treatment of migraine: the Achieve II randomized clinical trial." *Jama* 322.19: 1887-1898 (2019).

Lipton et al., "Efficacy, safety, and tolerability of rimegepant 75 mg orally dissolving tablet for the acute treatment of migraine: Results from a phase 3, double-blind, randomized, placebo-controlled trial, Study 303", Headache, 59: 21-22 (2019).

Lipton et al., (Postgraduate Medicine, Minneapolis (2001) 109: 1-6)(2001).

Lipton R.B, et al., "Impact of NSAID and Triptan Use on Developing Chronic Migraine: Results from the American Migraine Prevalence and Prevention (AMPP) Study, " Headache, Nov./Dec. 2013, vol. 53 (10), pp. 1548-1563.

Magellan RX Management, Ubrogepant (Ubrelvy™) New Drug Update; retrieved online <https://www.hhs.texas.gov/sites/default/files/documents/about-hhs/communications-events/meetings-events/dur/may-2020/may-2020-durb-agenda-item-5c.pdf>: 8 pages (2020).

McCarthy, "Oral rimegepant increased freedom from pain and from most bothersome symptom at 2 h in acute migraine." Annals of internal medicine 171(10) (2019): JC59.

Medsafe, "Drug Metabolism—The Importance of Cytochrome P450 3A4", retrieved online https://www.medsafe.govt.nz/profs/PUArticles/March2014DrugMetabolismCytochromeP4503A4.htm (2014).

Menard et al. "A calcitonin gene-related peptide receptor antagonist prevents the development of tolerance to spinal morphine analgesia," Journal of Neuroscience 16. 7, 2342-2351 (1996).

Merck, B.I. and Co Inc Harleysville PA USA et al.: "Discovery of AGN-241689: A potent, orally-acting CGRP receptor antagonist for migraine prophylaxis", Abstracts of Papers, ACS National Meeting & Exposition; 253rd National Meeting Of The American-Chemical-Society (ACS) On Advanced Materials, Technologies, Systems, And Processes; San Francisco, CA, USA, Apr. 2-6, 2017. American Chemical Society, vol. 253. Apr. 2, 2017 (Apr. 2, 2017). p. 20. XP009516497.

Messali A.J., et al., "Treatment persistence and switching in triptan users: a systematic literature review," Headache, Jul.-Aug. 2014, vol. 54 (7), pp. 1120-1130.

Messina R., et al., "CGRP—A Target for Acute Therapy in Migraine: Clinical Data," Cephalalgia, An International Journal of Headache, 2019, vol. 39(3), pp. 420-427.

Molina et al. "Induction of Insulin Resistance In Vivo by Amylin and Calcitonin Gene—Related Peptide," Diabetes 39.2, 260-265 (1990).

Mullin et al., "Potential for treatment benefit of small molecule CGRP receptor antagonist plus monoclonal antibody in migraine therapy", Neurology, vol. 94, No. 20, Jan. 13, 2020, pp. e2121-e2125.

Mullin, "Acute treatment benefit from oral CGRP receptor antagonist and monoclonal antibody combination: rimegepant 75mg for acute treatment of attacks during preventive therapy with erenumab", 61st Annual Scientific Meeting American Headache Society, Jun. 1, 2019, pp. 176-177.

Mullin, "Successful gepant-monoclonal antibody combination: Rimegepant 75mg for acute treatment of attacks during preventive therapy with erenumab", Cephalalgia Sep. 1, 2019 Sage Publications Ltd NLD, vol. 39, No. 1, Supplement, Sep. 1, 2019.

National Center for Biotechnology Information ""*Homo sapiens* mRNA encoding RAMP1,"" GenBank Accession No. AJ001014, 2 pages, (2008).

National Center for Biotechnology Information "*Homo sapiens* (clone HSNME29) CGRP type 1 receptor mRNA, complete ends," GenBank Accession No. L76380,2 pages, (1996).

Negro A., et al., "CGRP Receptor Antagonists: An Expanding Drug Class for Acute Migraine?," Expert Opinion on Investigational Drugs, 2012, vol. 21(6), pp. 807-818.

Negro A., et al., "Serotonin receptor agonists in the acute treatment of migraine: a review on their therapeutic potential," Journal of Pain Research, Mar. 2018, vol. 11, pp. 515-526.

Neuschwander-Tetri B.A. et. al., "The upper limits of normal for serum ALT levels reported by clinical laboratories depend on local reference populations," Arch Intern Med., Mar. 2004, vol. 168(6), pp. 663-666.

Olesen et al. "Calcitonin gene-related peptide receptor antagonist BIBN 4096 BS for the acute treatment of migraine," New England Journal of Medicine 350.11, 1104-1110. (2004).

Ornello R., et al., "Migraine and body mass index categories: a systematic review and meta-analysis of observational studies," The journal of headache and pain, Mar. 2015, vol. 16 (1), 14 pgs.

Partial EP Search Report for EP Application No. 20869848.0 dated Sep. 21, 2023.

Peterlin B.L., et al., "Obesity and migraine: the effect of age, gender and adipose tissue distribution," Headache, Jan. 2010, vol. 50 (1), pp. 52-62.

Petersen et al. "BIBN4096BS Antagonizes Human a-calcitonin Gene Related Peptide-C35 induced Headache and Extracerebral Artery Dilatation," Clinical Pharmacology & Therapeutics 77.3 :202-213.(2005).

Pitt et al., "Determination of the Tensile Strength of Elongated Tablets," Powder Technology, 238: 169-175 (2013).

Ramadhani et al. "Preparation and Characterisation of Kolliphor P188 and P 237 Solid Dispersion Oral Tablets Containing the Poorly Water Soluble DrugDisulfiram". International Journal of Pharmaceutics. Sep. 2014 [Online], 475:514-522. (Year: 2014).

Rapoport et al., "Triptans are all Different", Arch Neurol, 58(9):1479-1480 (2001).

Remington J.P "Remington's Pharmaceutical Sciences," 17th Edition Edited by Alfonso R. Gennaro, Mack Publishing Co, Journal of Pharmaceutical Science, 1985, vol. 74 (10).

Remington, "The Science and Practice of Pharmacy", 2000, Lippincott Williams&Wilkins, XP002773203, pp. 861-862.

Repka et al., "Melt Extrusion: Process to Product," Expert Opinion on Durg Delivery, Dec. 6, 2011, 9(1): 105-125.

Reuter, "A Review of Monoclonal Antibody Therapies and Other Preventative Treatments in Migraine", Headache, Woodbury, NJ, United States, vol. 58, Apr. 26, 2018, pp. 48-59.

Rohrenbeck et al. "Upregulation of COX-2 and CGRP expression in resident cells of the C36 Borna disease virus-infected brain is dependent upon inflammation," Neurobiology of disease 6.1 : 15-34.(1999).

Rowe et al., "Handbook of Pharmaceutical Excipients", 2000, Pharmaceutical Press, XP002773225, p. 201.

Rowe R.C., et al., "Handbook of Pharmaceutical Excipients," APhA Publications, 4th edition, 2003. pp. 1-6.

Russo., "CGRP-Based Migraine Therapeutics: How Might They Work, Why So Safe, and What Next?," ACS Pharmacology & Translational Science, 2(1): 2-8 (2019).

Salmon et al. "Altered neuroadaptation in opiate dependence and neurogenic inflammatory nociceotion in aCGRP-deficient mice," Nature neuroscience 4.4, : 357-358. (2001).

Saunders , B., "Allergan 2015 R&D Day", (Nov. 5, 2015), Powerpoint Presentation, slide 1-3 and 49-51. (Allergan plc, 2015).

Scher A.I., et al., "Factors associated with the onset and remission of chronic daily headache in a population-based study," Pain, Nov. 2003, vol. 106 (1-2), pp. 81-89.

Schini-Kerth et al. "CGRP enhances induction of NO synthase in vascular smooth muscle C38 cells via a cAMP-dependent mechanism," American Journal of Physiology—Heart and Circulatory Physiology 267.6 : 2483-2490 (1994).

(56) References Cited

OTHER PUBLICATIONS

Schuster et al., "Calcitonin Gene-Related Peptide-Targeted Therapies for Migraine and Cluster Headache: A Review," Clinical Neuropharmacology, 40(4): 169-174 (2017).
Schwedt et al., "Time course efficacy of atogepant for the preventive treatment of migraine: Results from the randomized, double-blind Advance trial" Cephalgia, vol. 42, No. 1, p. 3-11 (2022).
Scott., "Ubrogepant: First Approval," Drugs, 80: 323-328 (2020).
Serrano D., et al., "Effects of Switching Acute Treatment on Disability in Migraine Patients Using Triptans," Headache, Oct. 2013, vol. 53 (9), pp. 1415-1429.
Shaw et al., "Carprolactams as Potent CGRP Receptor Antagonists for the Treatment of Migraine", Bioorg Med. Chem Lett, 2007, pp. 4795-4798, 17.
Silberstein S.D., et al., "Pharmacologic treatment for episodic migraine prevention in adult," American Academy of Neurology, Apr. 2012, vol. 78 (17), pp. 1337-1345.
Spetz et al. "Momentary increase in plasma calcitonin gene-related peptide is involved in hot flashes in men treated with castration for carcinoma of the prostate," The Journal of urology 166.5, 1720-1723.(2001).
Szkutnik-Fiedler et al., "Pharmacokinetics, Pharmacodynamics and Drug-Drug Interactions of New Anti-Migraine Drugs-Lasmiditan, Gepants, and Calcitonin-Gene-Related Peptide (CGRP) Receptor Monoclonal Antibodies," Pharmaceutics, 12(12): 1-22 (2020).
Talal et al., "Assessment of hepatic impairment and implications for pharmacokinetics of substance use treatment", Clinical pharmacology in drug development 6.2: 206-212 (2017).
Tepper et al., "Erenumab in chronic migraine with medication overuse" Neurology, 92(20): e2309-2320 (2019).
Tepper et al., "Safety and efficacy of erenumab for preventive treatment of chronic migraine: a randomised, double-blind, placebo-controlled phase 2 trial," The Lancet Neurology, 16(6): 425-434 (2017).
Tepper, "CGRP and headache: a brief review", Neurological Sciences (Testo Stampato), Springer Verlag, Milan, IT, vol. 40, No. 1, Mar. 5, 2019, pp. 99-105.
Viana M., et al., "Triptan non-responders: do they exist and who are they?," Cephalalgia, Aug. 2013, vol. 33 (11 ), pp. 891-896.
Voss et al., "A phase IIb randomized, double-blind, placebo-controlled trial of ubrogepant for the acute treatment of migraine," Cephalalgia, 36(9): 887-898 (2016).
Walker et al. "Mice lacking the neuropeptide a-calcitonin gene-related peptide are protected against diet-induced obesity," Endocrinology 151.9 : 4257-4269. (2010).
Wallengren "Dual effects of CGRP-antagonist on allergic contact dermatitis in human skin." Contact dermatitis 43.3, : •137-143 (2000).
Williamson et al. ""The CGRP Family: Calcitonin Gene-Related Peptide (CGRP), Amylin, and Adrenomedullin, Landes,"" Bioscience 245-247.(2000).
Williamson et al. "Sumatriptan inhibits neurogenic vasodilation of dural blood vessels in the anaesthetized rat-intravital microscope studies," Cephalalaia 17.4 : 525-531 (1997).
Winter A.C. "Body mass index, migraine, migraine frequency and migraine features in women," Cephalalgia, Feb. 2009, vol. 29(2), pp. 269-278.
Wu et al., "Regulatory perspectives of Type II prodrug development and time-dependent toxicity management: Nonclinical Pharm/Tox analysis and the role of comparative toxicology," Toxicology 236(1-2): pp. 1-6 (2007).
Yang M., et al., "Validation of the Headache Impact Test (HIT-6™) Across Episodic and Chronic Migraine," Cephalalgia, Feb. 2011; vol. 31(3), pp. 357-367.
Yoshida et al. "Systematic and quantitative assessment of the effect of chronic kidney disease on CYP2D6 and CYP3A4/5." Clinical Pharmacology & Therapeutics 100.1 (2016): 75-87.
Yu et al. "Effects of calcitonin gene-related peptide-(8-37) on withdrawal responses in rats with inflammation," European journal of pharmacology 347.2-3, 275-282. (1998).
Yuan et al., "CGRP therapeutics for the treatment of migraine—a narrative review." Ann Head Med 1 (2020): 1-22.
Zhang et al. "Arthritic calcitonin/a calcitonin gene-related peptide knockout mice have reduced nociceptive hypersensitivity," Pain 89.2-3,: 265-273. (2001).
Zheng et al. "Severity of neurological signs and degree of inflammatory lesions in the brains of rats with Borna disease correlate with the induction of nitric oxide synthase," Journal of Virology 67.10, 5786-5791. (1993).

Mean ±SD Plasma Ubrogepant Concentration (ng/mL) – Time Profile, Linear Scale – PK Population

TREATMENT OF MIGRAINE

CROSS-REFERENCE TO RELATED APPLICATIONS

The present application is a divisional of U.S. application Ser. No. 18/440,217, filed Feb. 13, 2024; which is a continuation-in-part of U.S. application Ser. No. 18/523,481, filed Nov. 29, 2023; which is a continuation of U.S. application Ser. No. 18/210,719, filed Jun. 16, 2023; which is a continuation of U.S. application Ser. No. 17/559,177, filed Dec. 22, 2021; which claims the benefit of U.S. Provisional Application No. 63/129,379, filed Dec. 22, 2020.

U.S. application Ser. No. 18/440,217 is also a continuation-in-part of U.S. application Ser. No. 18/137,925, filed Apr. 21, 2023; which is a continuation of U.S. patent application Ser. No. 17/110,398, filed Dec. 3, 2020, which is a continuation of U.S. patent application Ser. No. 16/178,641, filed Nov. 2, 2018, which is a continuation of U.S. patent application Ser. No. 15/115,026, filed Jul. 28, 2016 now U.S. Pat. No. 10,117,836, which is a U.S. National Phase application under 35 U.S.C. § 371 of PCT Application No. PCT/US2015/013672, filed Jan. 30, 2015, which claims the benefit of U.S. Provisional Patent Application Ser. No. 61/936,019 filed Feb. 5, 2014 and U.S. Provisional Patent Application Ser. No. 62/087,366 filed Dec. 4, 2014.

The contents of each of these applications is incorporated by reference herein in its entirety.

FIELD

The present disclosure is related to medicaments and methods for treating migraine. In particular, the present disclosure is related to medicaments and methods for the acute treatment of migraine with or without aura.

BACKGROUND

Migraine is a highly prevalent, severe, and disabling neurological condition with a significant unmet need for effective treatments. (Holland, P. R. & Goadsby, P. J. Neurotherapeutics (2018). Migraine represents a significant burden to patients and society. There remains a need for optimized and targeted methodologies and dosing regimens to treat migraines.

CGRP (calcitonin gene-related peptide) is a naturally occurring 37-amino acid peptide that is generated by tissue-specific processing of calcitonin messenger RNA and is widely distributed in the central and peripheral nervous system. CGRP is a potent vasodilatory neurotransmitter believed to play a key role in migraine pathophysiology.

The initial clinical validation of the CGRP target was provided by Boehringer Ingelheim in 2003 with the report that an IV formulation comprising olcegepant was efficacious in the acute treatment of migraine and the mechanism was confirmed by a study using telcagepant (a CGRP antagonist) in an oral formulation. The first clinically tested CGRP antagonist, olcegepant, was based on a dipeptide backbone, had a high molecular weight, and was not orally bioavailable. Later, a number of orally-acting CGRP antagonists were advanced to clinical trials, including MK-3207 and telcagepant. However, elevated liver enzyme levels were observed for MK-3207 and telcagepant, leading to the discontinuation of both programs.

It would thus be advantageous to develop effective methods of treating acute migraine with CGRP antagonists.

SUMMARY

In embodiments, the present disclosure provides a method for the acute treatment of migraine with or without aura in a patient with severe hepatic impairment, where the method involves administering 50 mg of ubrogepant to a patient having a Child-Pugh score/classification of Child-Pugh Class C. In embodiments, the patient may optionally be administered a second 50 mg dose of ubrogepant at least 2 hours after the first 50 mg dose. In embodiments, the second dose of ubrogepant may be administered between 2-24 hours after the first dose of ubrogepant.

In embodiments, the present disclosure provides a method for the acute treatment of migraine with or without aura in a patient with severe renal impairment, the method comprising administering a first 50 mg dose of ubrogepant to a patient, wherein the patient's estimated creatinine clearance as determined using the Cockcroft-Gault equation is 15-29 mL/min. In embodiments, an optional second dose of 50 mg ubrogepant may be administered at least 2 hours after the first dose of ubrogepant. In embodiments, the optional second dose of ubrogepant is administered between 2-24 hours after the first dose of ubrogepant.

In embodiments, the present disclosure provides a method for the acute treatment of migraine with or without aura in patients undergoing treatment with a moderate CYP3A4 inhibitor, the method comprising administering 50 mg ubrogepant to the patient undergoing treatment with the moderate CYP3A4 inhibitor. In embodiments, the 50 mg dose of ubrogepant is the only dose of ubrogepant administered to the patient in a 24 hour period (i.e., the maximum amount of ubrogepant administered to the patient in a 24-hour period is 50 mg).

In embodiments, the present disclosure provides a method for the acute treatment of migraine with or without aura in patients undergoing treatment with a weak CYP3A4 inhibitor, the method comprising administering 50 mg ubrogepant to the patient taking the weak CYP3A4 inhibitor. In embodiments, an optional second 50 mg dose of ubrogepant may be administered to the patient at least 2 hours after the first dose of ubrogepant. In embodiments, the second dose of ubrogepant is administered between 2 and 24 hours after the first dose of ubrogepant. In embodiments, the maximum dosage of ubrogepant in a 24-hour period for a patient taking a weak CYP3A4 inhibitor is 100 mg.

In embodiments, the present disclosure provides a method for the acute treatment of migraine with or without aura in a patient undergoing treatment with a weak or moderate CYP3A4 inducer, the method comprising administering 100 mg ubrogepant to the patient taking the weak or moderate CYP3A4 inducer. In embodiments, an optional second 100 mg dose of ubrogepant may be administered at least 2 hours after the first dose of ubrogepant. In embodiments, the optional second dose is administered between 2 and 24 hours after the first dose of ubrogepant. In embodiments, the maximum dosage of ubrogepant in a 24-hour period for a patient taking a weak or moderate CYP3A4 inducer is 200 mg.

In embodiments, the present disclosure provides a method for the acute treatment of migraine with or without aura in a patient undergoing concurrent treatment with a BCRP and/or P-gp only inhibitor, the method comprising administering 50 mg ubrogepant to said patient taking a BCRP and/or P-gp only inhibitor. In embodiments, an optional second 50 mg dose of ubrogepant may be administered at least 2 hours after the first dose of ubrogepant. In embodiments, the optional second dose is administered between 2-24 hours after the first dose of ubrogepant. In embodiments, the maximum dosage of ubrogepant in a 24-hour period for a patient taking a BCRP and/or P-gp only inhibitor is 100 mg.

Figure 8:
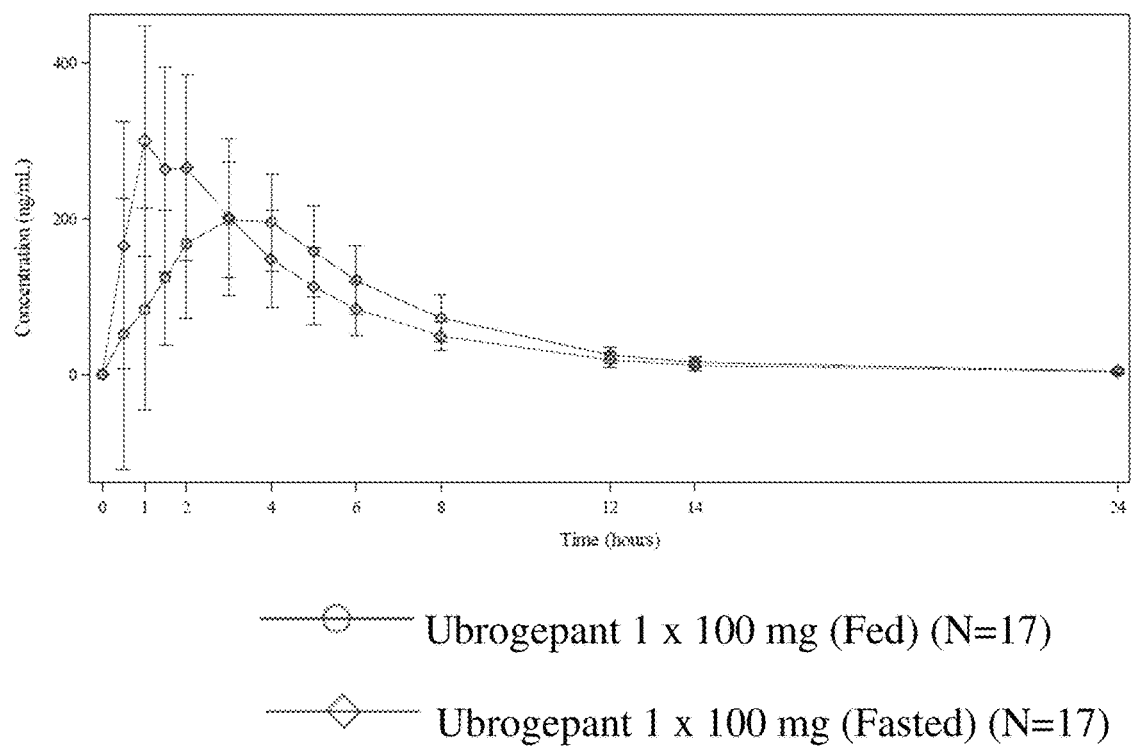
Figure 9:
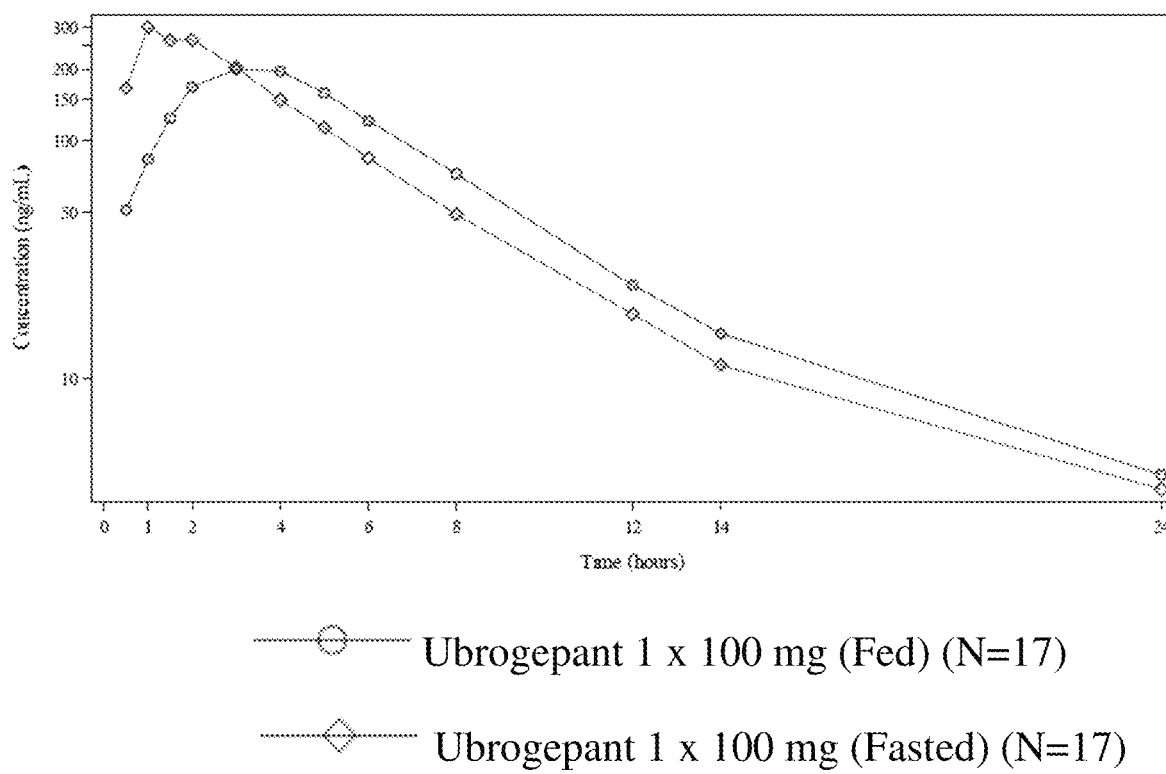

The mean concentration-time profiles for plasma ubrogepant after single-dose administration of the 100 mg ubrogepant tablet under fed and fasted conditions are shown in FIG. 8 (linear scale) and FIG. 9 (semilogarithmic scale).

Figure 10:
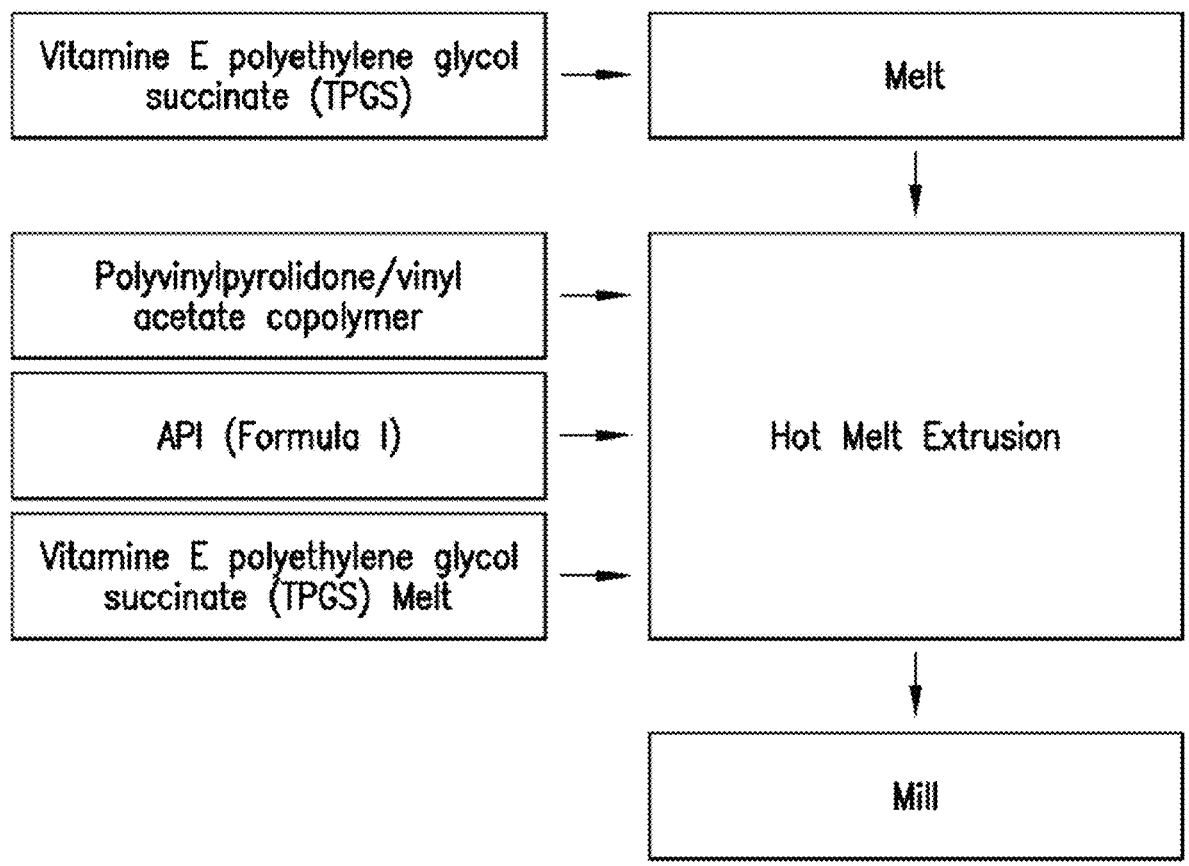

FIG. 10 is a flow chart illustrating unit operations in general preparation of dispersions of the present disclosure.

Formula I

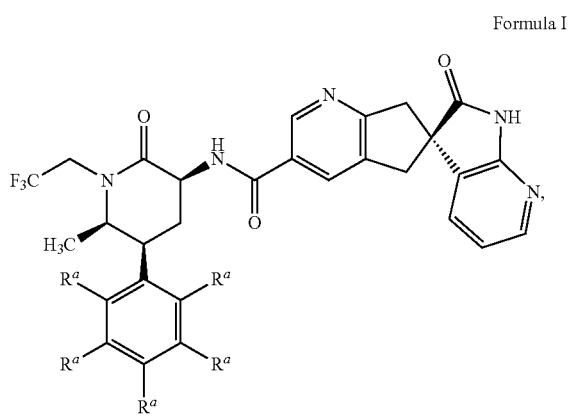

Figure 11:
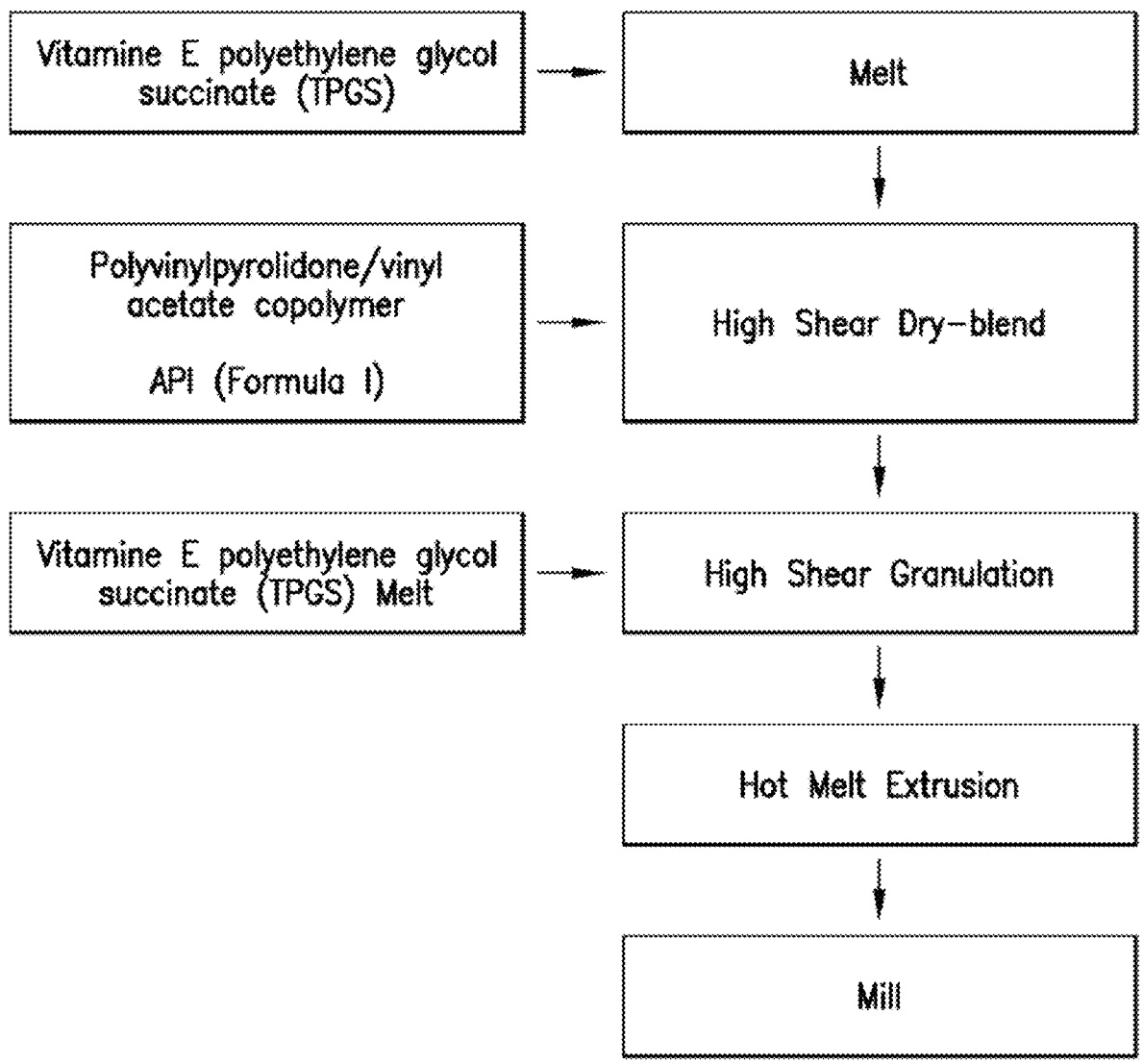

FIG. 11 is a flow chart illustrating unit operations in an alternative general preparation of a dispersion of the present disclosure.

Figure 12:
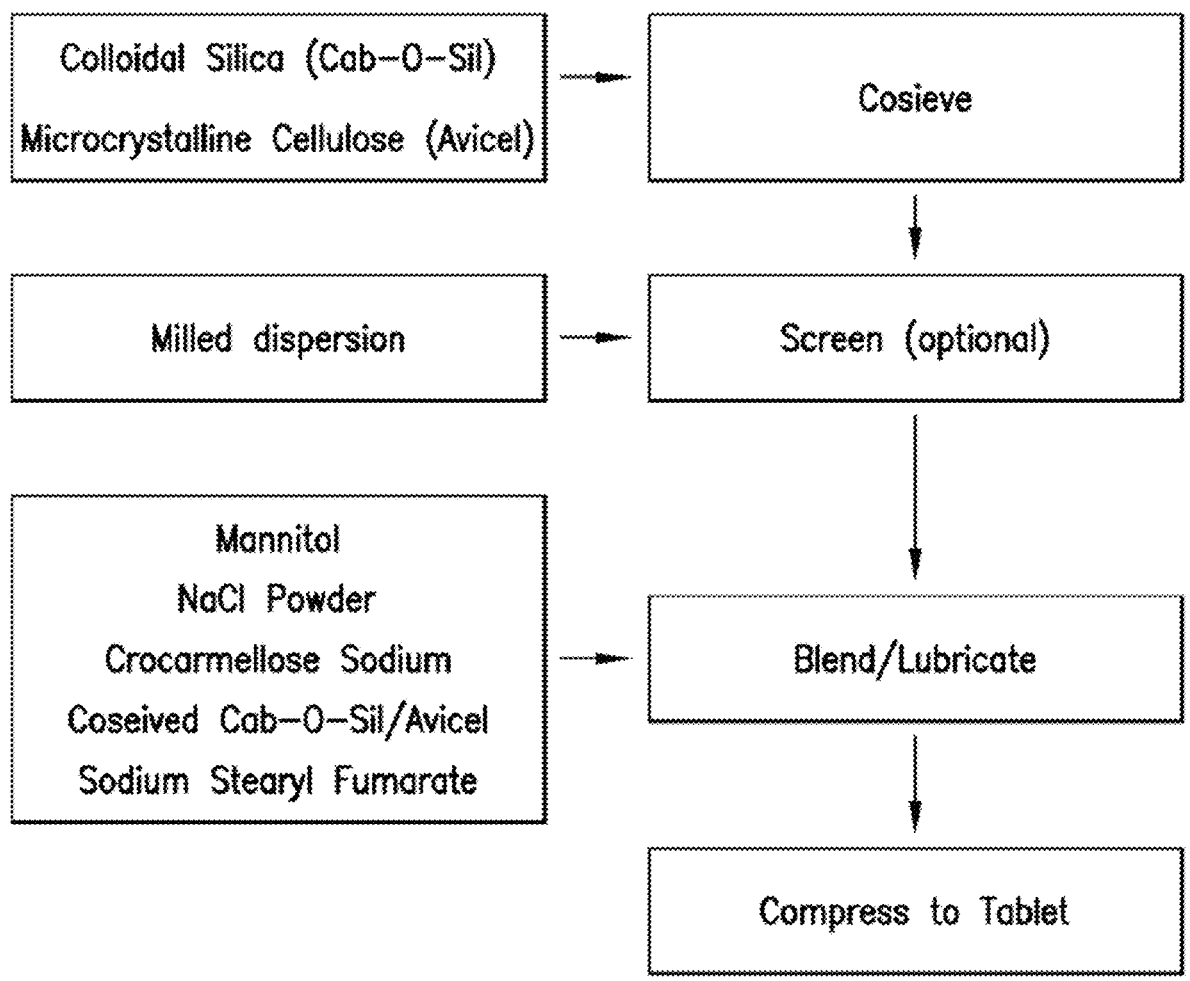

FIG. 12 is a flow chart illustrating flow operations in formulating tablets of the present disclosure.

DETAILED DESCRIPTION

Ubrelvy® (ubrogepant) is believed to have utility in treating patients suffering from acute migraine attack. Ubrogepant has the following structure:

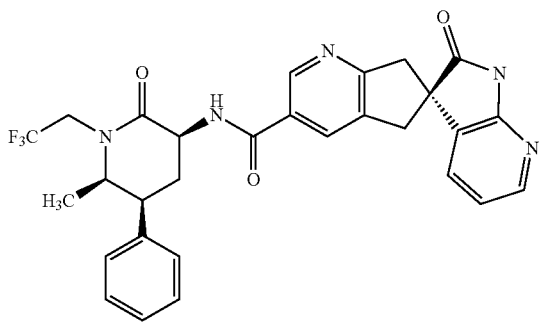 [SMILES: C[C@@H]1[C@H](c2ccccc2)C[C@H](NC(=O)c2cnc3c(c2)C[C@@]2(C3)C(=O)Nc3ncccc32)C(=O)N1CC(F)(F)F]

Ubrogepant is also known as (3'S)-N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide. Ubrogepant is a calcitonin gene-related peptide (CGRP) receptor antagonist that is primarily metabolized by cytochrome P450 3A4 (CYP3A4) and is a P-glycoprotein substrate.

Ubrogepant may be administered as tablets for oral administration. For example, tablet formulations described in U.S. Pat. No. 10,117,836, which is incorporated by reference in its entirety, can be used in any method of treatment described herein. Ubrogepant is also known as compound "FIa-H", described in U.S. Pat. No. 10,117,836. In embodiments, the tablets may comprise 50 mg or 100 mg ubrogepant.

The elimination half-life of ubrogepant is approximately 5-7 hours. The mean apparent oral clearance (CL/F) of ubrogepant is approximately 87 L/hr. Ubrogepant is excreted mainly through the biliary/fecal route, while the renal route is a minor route of elimination. Following single dose administration of [$^{14}$C]-ubrogepant to healthy male subjects, 42% and 6% of the dose was recovered as unchanged ubrogepant in feces and urine, respectively.

Following oral administration of ubrogepant, ubrogepant is absorbed with peak plasma concentrations at approximately 1.5 hours. When ubrogepant is administered with a high-fat meal, the time to maximum plasma concentration is delayed by 2 hours and results in a 22% reduction in $C_{max}$ with no change in AUC. In clinical studies, ubrogepant was administered without regard to food.

Plasma protein binding of ubrogepant is 87% in vitro. The mean apparent central volume of distribution of ubrogepant (V/L) after single dose oral administration is approximately 350 L.

Methods of Treating Acute Migraine

In embodiments, the present disclosure provides for a method for the acute treatment of migraine (e.g., treatment of acute migraine) with or without aura. In embodiments, the method comprises administering 50 mg or 100 mg of ubrogepant. In embodiments, ubrogepant is taken orally with or without food. In embodiments, a second dose may be taken at least 2 hours after the initial dose, where the maximum dose in a 24 hour period is 200 mg. In embodiments, the second dose of ubrogepant is taken between 2-24 hours after the first dose of ubrogepant.

It will be understood that a patient may be administered a particular amount of ubrogepant (e.g., 50 mg or 100 mg), or may be administered a pharmaceutically acceptable salt of ubrogepant in an amount equivalent to that dose (e.g., a pharmaceutically acceptable salt of ubrogepant in an amount equivalent in potency to 50 mg of ubrogepant, or a pharmaceutically acceptable salt in an amount equivalent in potency to 100 mg of ubrogepant). Disclosure of a particular dose of ubrogepant also includes pharmaceutically acceptable salts of ubrogepant in an amount equivalent to that dose.

Methods of Treating Acute Migraine in Patients Having Hepatic Impairment

Ubrogepant is mainly metabolized by hepatic CYP isoenzymes, thus creating the potential that patients with varying degrees of hepatic impairment might achieve higher systemic concentrations of ubrogepant. The present disclosure provides methods of safely administering ubrogepant to patients having mild, moderate, or severe hepatic impairment for the treatment of acute migraine with or without aura.

In embodiments, the present disclosure provides methods of treating acute migraine with or without aura in patients with hepatic impairment. In embodiments, the hepatic impairment is pre-existing. "Hepatic impairment' is used in accordance with its standard meaning and can, in embodiments, refer to scoring based on the Child-Pugh Score of A, B, and C.

In patients with pre-existing mild (Child-Pugh Class A) or moderate (Child-Pugh Class B) hepatic impairment, it was determined that ubrogepant exposure was increased by 7% and 50%, respectively. In patients with severe (Child-Pugh Class C) hepatic impairment, it was determined that ubrogepant exposure was increased by 115%.

Accordingly, in embodiments, patients with severe hepatic impairment (Child-Pugh Class C) require a dose adjustment as compared to patients without severe hepatic impairment. In embodiments, the present disclosure provides a method of treating acute migraine with or without aura in patients with severe hepatic impairment, the method comprising administering 50 mg of ubrogepant to a patient having severe hepatic impairment (Child-Pugh Class C). In embodiments, ubrogepant is taken orally with or without food.

In patients with migraine, it is sometimes not sufficient to take a single dose of a migraine medication. For example, a patient may take a migraine medication, and still experience symptoms including pain, photophobia, phonophobia, nausea, or emesis after 2 hours, and may require additional treatment. It was determined that patients having severe hepatic impairment may take a second dose of ubrogepant at least 2 hours after the first dose of ubrogepant. In embodiments, the second dose of ubrogepant is taken between 2 and 24 hours after the first dose of ubrogepant. In embodiments, the second dose of ubrogepant is 50 mg.

In embodiments, the present disclosure provides a method for the acute treatment of migraine with or without aura in patients having mild hepatic impairment (Child-Pugh Class A), the method comprising administering 50 or 100 mg of ubrogepant. In embodiments, ubrogepant is taken orally with or without food. In embodiments, a second dose of ubrogepant may be taken at least 2 hours after the initial dose, where the maximum dose in a 24 hour period is 200 mg. In embodiments, the second dose of ubrogepant is taken between 2 and 24 hours after the first dose of ubrogepant.

In embodiments, the present disclosure provides a method for the acute treatment of migraine with or without aura in patients having moderate hepatic impairment (Child-Pugh Class B), the method comprising administering 50 or 100 mg of ubrogepant. In embodiments, ubrogepant is taken orally with or without food. In embodiments, a second dose of ubrogepant may be taken at least 2 hours after the initial dose, where the maximum dose in a 24 hour period is 200 mg. In embodiments, the second dose of ubrogepant is taken between 2 and 24 hours after the first dose of ubrogepant.

In embodiments, the present disclosure provides a method for the acute treatment of migraine with or without aura in a patient having hepatic impairment, the method comprising first determining whether the patient has mild hepatic impairment (Child Pugh Class A), moderate hepatic impairment (Child Pugh Class B), or severe hepatic impairment (Child Pugh Class C). If the patient has mild or moderate hepatic impairment, the method further comprises administering 50 or 100 mg ubrogepant. In embodiments, ubrogepant may be taken orally with or without food. In embodiments, a second dose of ubrogepant may be taken by the patient having mild or moderate hepatic impairment at least 2 hours after the initial dose. In embodiments, the second dose is taken between 2 and 24 hours after the initial dose. In embodiments, the second dose of ubrogepant is 50 or 100 mg. In embodiments, the maximum dose in a 24 hour period is 200 mg. If the patient has severe hepatic impairment, the method further comprises administering 50 mg ubrogepant to the patient. In embodiments, ubrogepant may be taken orally with or without food. In embodiments, a second dose of ubrogepant may be taken by the patient having severe hepatic impairment at least two hours after the first dose of ubrogepant. In embodiments, the second dose of ubrogepant administered to the patient having severe hepatic impairment is a 50 mg dose of ubrogepant. In embodiments, the second dose of ubrogepant is taken between 2 and 24 hours after the first dose of ubrogepant.

Methods of Treating Acute Migraine in Patients Having Renal Impairment

The renal route elimination is a minor excretion pathway for ubrogepant (<10%). Population pharmacokinetic analysis based on pooled data from clinical studies was used to evaluate the effect of renal impairment characterized based on estimated creatinine clearance (CLcr) using the Cockcroft-Gault (C-G) equation. Renal impairment did not reveal a significant difference in the pharmacokinetics of ubrogepant in patients with mild or moderate renal impairment (CLcr 30-89 mL/min) relative to those with normal renal function (CLcr>90 mL/min).

Accordingly, in embodiments, the present disclosure provides a method for the acute treatment of migraine with or without aura in patients having mild or moderate renal impairment (CLcr 30-89 mL/min), the method comprising administering 50 or 100 mg of ubrogepant. In embodiments, ubrogepant is taken orally with or without food. In embodiments, a second dose of 50 or 100 mg of ubrogepant may be taken at least 2 hours after the initial dose, where the maximum dose in a 24 hour period is 200 mg.

However, in embodiments, dose adjustment is required in patients with severe renal impairment (CLcr 15-29 mL/min). In embodiments, the present disclosure provides a method for the acute treatment of migraine with or without aura in patients having severe renal impairment, the method comprising administering 50 mg of ubrogepant to a patient having severe renal impairment (CLcr 15-29 mL/min). In embodiments, ubrogepant is taken orally with or without food.

As discussed above, in some patients, a single dose of medication is not sufficient to address their migraine symptoms. That is, a patient may take a first dose of ubrogepant, and still experience some symptoms including pain, photophobia, phonophobia, nausea, or emesis after 2 hours, and may require additional treatment. In embodiments, the present disclosure provides a method of treating migraine in patients with severe renal impairment, the method comprising administering to a patient having severe renal disease a first dose of 50 mg ubrogepant as described above, and then optionally administering a second 50 mg dose of ubrogepant at least 2 hours after the first dose of ubrogepant. In embodiments, the second dose of ubrogepant is administered between 2 and 24 hours after the first dose of ubrogepant.

In embodiments, the present disclosure provides that use of ubrogepant should be avoided in patients with end-stage renal disease (ESRD) (CLcr<15 mL/min).

In embodiments, the present disclosure provides a method for the acute treatment of migraine with or without aura in a patient having renal impairment, the method comprising first determining whether the patient has mild renal impairment, moderate renal impairment, severe renal impairment (CLcr 15-29 mL/min) or end-stage renal disease (CLcr<15 mL/min). In embodiments, if the patient has mild or moderate renal impairment, the method comprises administering 50 or 100 mg ubrogepant to the patient. In embodiments, ubrogepant may be taken orally with or without food. In embodiments, a second dose of ubrogepant may be taken by the patient having mild or moderate renal impairment at least 2 hours after the initial dose. In embodiments, the second dose is taken from 2 to 24 hours after the initial dose. In embodiments, the second dose of ubrogepant is 50 or 100 mg. In embodiments, the maximum dose in a 24 hour period is 200 mg. In embodiments, if the patient has severe renal impairment, the method comprises administering 50 mg ubrogepant to the patient. In embodiments, ubrogepant may be taken orally with or without food. In embodiments, a second dose of ubrogepant may be taken by the patient having severe renal impairment at least two hours after the first dose of ubrogepant. In embodiments, the second dose is administered between 2 and 24 hours after the first dose of ubrogepant. In embodiments, the second dose of ubrogepant administered to the patient having severe renal impairment is a 50 mg dose of ubrogepant. In embodiments, if the patient is determined to have end-stage renal disease, administration of ubrogepant is avoided.

Co-administration of Ubrogepant with CYP3A4 Inhibitors

Co-administration of ubrogepant with ketoconazole, a strong CYP3A4 inhibitor, resulted in a significant increase in exposure of ubrogepant. Ubrogepant should not be used with strong CYP3A4 inhibitors. Strong CYP3A4 inhibitors include, for example, ketoconazole, itraconazole, or clarithromycin.

Accordingly, in embodiments, the present disclosure provides a method for the acute treatment of migraine, the method comprising administering 50 mg or 100 mg of ubrogepant to a patient in need thereof, wherein if the patient begins concurrent treatment with a strong CYP3A4 inhibitor (e.g., ketoconazole, itraconazole, or clarithromycin), treatment with ubrogepant is discontinued.

"Concurrent"/"concurrently" or "concomitant"/"concomitantly" both include in their meaning (1) simultaneously in time (e.g., at the same time) and (2) at different times but within the course of a common treatment schedule.

Coadministration of ubrogepant with verapamil, a moderate CYP3A4 inhibitor, resulted in an increase in ubrogepant exposure. Dose adjustment is therefore recommended with concomitant use of ubrogepant and moderate CYP3A4 inhibitors. Moderate CYP3A4 inhibitors include, for example, cyclosporine, ciprofloxacin, fluconazole, fluvoxamine, or grapefruit juice.

In embodiments, the present disclosure provides a method for the acute treatment of migraine with or without aura in patients undergoing concurrent treatment with a moderate CYP3A4 inhibitor, the method comprising administering 50 mg ubrogepant to the patient undergoing concurrent treatment with a moderate CYP3A4 inhibitor. In embodiments, the CYP3A4 inhibitor may be administered before, concomitantly with, or after the ubrogepant is administered. In embodiments, the maximum daily dose of ubrogepant when administered to patients concomitantly using moderate CYP3A4 inhibitors is 50 mg. That is to say, in patients who have taken a moderate CYP3A4 inhibitor and a first 50 mg dose of ubrogepant, a second dose of ubrogepant is avoided within 24 hours of the first dose of ubrogepant.

In embodiments, the present disclosure provides a method of administering ubrogepant in combination with a moderate CYP3A4 inhibitor, the method comprising administering 50 mg ubrogepant to a patient taking a moderate CYP3A4 inhibitor. In embodiments, the CYP3A4 is administered before, concurrently with, or after administration of ubrogepant. In embodiments, when a patient has been administered a CYP3A4 inhibitor and a first 50 mg dose of ubrogepant, a second dose of ubrogepant is avoided within 24 hours of the first dose of ubrogepant.

In embodiments, the present disclosure provides a method for the acute treatment of migraine with or without aura, the method comprising administering 50 or 100 mg of ubrogepant to a patient and optionally administering a second 50 or 100 mg dose of ubrogepant between 2-24 hours after the initial dose of ubrogepant, wherein if the patient begins concurrent therapy with a moderate CYP3A4 inhibitor, the dose of ubrogepant is reduced to 50 mg. In embodiments, the maximum daily dose of ubrogepant after the patient begins treatment with a moderate CYP3A4 inhibitor is 50 mg. That is, in embodiments, only one dose of 50 mg ubrogepant is administered in a 24 hour period in patients taking both ubrogepant and a moderate CYP3A4 inhibitor.

In embodiments, the present disclosure provides a method for the acute treatment of migraine with or without aura in patients undergoing concurrent treatment with a mild CYP3A4 inhibitor, the method comprising administering 50 mg ubrogepant to a patient taking a weak CYP3A4 inhibitor. In embodiments, the weak CYP3A4 inhibitor may be taken before, concurrently with, or after administration of ubrogepant. In embodiments, an optional second dose of 50 mg ubrogepant may be administered more than 2 hours after the first dose of ubrogepant. In embodiments, the second dose of ubrogepant is administered within 2 to 24 hours of the first 50 mg dose of ubrogepant.

In embodiments, the present disclosure provides a method for the acute treatment of migraine with or without aura, the method comprising administering 50 or 100 mg of ubrogepant to a patient and optionally administering a second 50 or 100 mg dose of ubrogepant between 2-24 hours after the initial dose of ubrogepant, wherein if the patient begins concurrent therapy with a weak CYP3A4 inhibitor, the dose of ubrogepant is reduced to 50 mg, and an optional second 50 mg dose of ubrogepant may be administered between 2-24 hours after the first 50 mg dose of ubrogepant.

Co-administration of Ubrogepant with CYP3A4 Inducers

It has been determined that co-administration of ubrogepant with rifampin, a strong CYP3A4 inducer, resulted in a significant reduction in ubrogepant exposure. Accordingly, ubrogepant should not be used with strong CYP3A4 inducers, as loss of ubrogepant efficacy may result.

In embodiments, the present disclosure provides a method of administering ubrogepant (such as for the acute treatment of migraine with or without aura), the method comprising administering 50 or 100 mg ubrogepant, wherein if the patient begins treatment with a strong CYP3A4 inhibitor, treatment with ubrogepant is discontinued. Strong CYP3A4 inducers include, for example, phenytoin, barbiturates, rifampin, or St. John's Wort.

Because ubrogepant is considered a sensitive CYP3A4 substrate (i.e., mainly eliminated by CYP3A4 metabolism and strong CYP3A4 inhibition resulted in about 10-fold increase in its exposure), drug interaction with weak or moderate inducers may reduce ubrogepant exposure by 20-50% or 50-80% respectively. Because 50 mg and 100 mg ubrogepant doses are considered safe and effective, the 100 mg dose may be used if concomitant use of a weak or moderate CYP3A4 inducer cannot be avoided.

Accordingly, in embodiments, the present disclosure provides a method for the acute treatment of migraine with or without aura in patients taking a moderate or weak CYP3A4 inducer, the method comprising administering 100 mg ubrogepant to the patient undergoing concurrent treatment with a moderate or weak CYP3A4 inducer. In embodiments, the CYP3A4 inducer may be administered before, concomitantly with, or after ubrogepant. In embodiments, an optional second dose of 100 mg ubrogepant may be administered at least 2 hours after the first dose of ubrogepant. In embodiments, the second dose of ubrogepant is administered between 2 and 24 hours after the first dose of ubrogepant.

In embodiments, the present disclosure provides a method for the acute treatment of migraine with or without aura, the method comprising administering 50 or 100 mg of ubrogepant to a patient in need thereof, and optionally administering a second 50 or 100 mg dose of ubrogepant within 2-24 hours of the first dose of ubrogepant, wherein if the patient begins concurrent treatment with a weak or moderate CYP3A4 inducer, the dose of ubrogepant is increased to 100 mg, and the optional second dose of ubrogepant is increased to 100 mg. In embodiments, the CYP3A4 inducer may be taken before, concurrently with, or after ubrogepant.

Co-Administration of Ubrogepant with BCRP and/or P-Gp Only Inhibitors

Ubrogepant is a substrate of BCRP and P-gp transporters in vitro, which creates the potential that use of inhibitors of BCRP and/or P-gp may increase the exposure of ubrogepant. It has been determined based on ADME and clinical interaction studies with CYP3A4/P-gp inhibitors that show that the highest predicted potential increase in exposure of ubrogepant is not expected to be more than 2-fold.

Accordingly, the present disclosure provides a method for the acute treatment of migraine with or without aura in patients taking a BCRP and/or P-gp only inhibitor, the method comprising administering 50 mg ubrogepant to the patient undergoing concurrent treatment with the BCRP and/or P-gp only inhibitor. In embodiments, the BCRP and/or P-gp only inhibitor may be administered before, concurrently with, or after ubrogepant. In embodiments, an optional second dose of 50 mg ubrogepant may be administered at least 2 hours after the first dose of ubrogepant. In embodiments, the second dose is administered 2-24 hours after the first dose of ubrogepant.

In embodiments, the present disclosure provides a method of administering ubrogepant in combination with a BCRP and/or P-gp only inhibitor, the method comprising administering 50 mg ubrogepant to a patient taking a BCRP and/or P-gp only inhibitor. In embodiments, the BCRP and/or P-gp only inhibitor is administered before, concurrently with, or after ubrogepant. In embodiments, a second 50 mg dose of ubrogepant may be administered at least 2 hours after the first dose of ubrogepant. In embodiments, the second dose of ubrogepant is administered between 2-24 hours after the first dose of ubrogepant.

In embodiments, the present disclosure provides a method for the acute treatment of migraine with or without aura, the method comprising administering 50 or 100 mg of ubrogepant to a patient and optionally administering a second 50 or 100 mg dose of ubrogepant between 2-24 hours after the first dose of ubrogepant, wherein if the patient begins concurrent therapy with a BCRP and/or P-gp only inhibitor, the dose of ubrogepant is adjusted to 50 mg. In embodiments, an optional second 50 mg dose of ubrogepant may be administered between 2-24 hours after the first dose of ubrogepant.

For any method of treatment described herein, ubrogepant in a tablet form as described in U.S. Pat. No. 10,117,836 can be used for oral administration. In embodiments, the tablet may be administered in the methods described within the present disclosure without regard to food (i.e., the tablet may be administered in the methods of the present disclosure with or without food).

In one aspect, the present disclosure provides a tablet comprising
  (a) an extrudate comprising
    (i) a water soluble polymer matrix;
    (ii) a dispersing agent; and
    (iii) a compound of Formula I, or a pharmaceutically acceptable salt thereof:

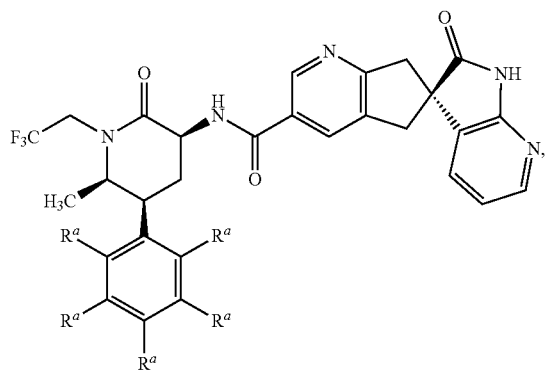

Formula I wherein "$R^a$" is independently —H or —F, and wherein the dispersing agent and compound of Formula I is dispersed within said polymer matrix; and
  (b) a disintegration system,
wherein said tablet has a hardness of from about 12 kP to about 18 kP, and wherein said tablet achieves complete disintegration in less than about 5 minutes in a standard tablet disintegration test complying with USP 31-NF26 Chapt. 701 using aqueous HCl (pH 1.8) at 37° C.

In some embodiments it is preferred for the disintegration system to comprise powdered sodium chloride and croscarmellose sodium, and more preferably in a 1:1 wt. ratio.

In some embodiments it is preferred for a tablet to have a hardness of from about 12 kP to about 16 kP. In some embodiments it is preferred for the tablet to have a tensile strength of about 1.75 MPa.

In some embodiments it is preferred for a tablet of the disclosure to release at least about 90 wt % of the compound of Formula I contained therein when subjected to a dissolution test complying with USP 30 NF25 Chapt. 711, apparatus #2 equipped with USP 2 paddles, operated at 50 rpm, in 900 ml of simulated gastric fluid (pH 1.8) at 37° C.

In some embodiments, preferably the tablet comprises a disintegration system comprising:
 (a) Powdered Sodium Chloride, wherein said sodium chloride is characterized by: (i) a d50 value of less than about 210 microns; (ii) a d10 value of less than about 50 microns; and (iii) a d90 value of less than about 470 microns; and
 (b) croscarmellose sodium,
wherein said Powdered Sodium Chloride and said croscarmellose sodium are present in a 1:1 weight ratio, and wherein the amount of extrudate present in the tablet is selected to provide from about 9 wt. % to about 10 wt. % of the compound of Formula I dispersed therein.

In some embodiments it is preferred for the disintegration system to comprise about 20 wt. % of the tablet. In some embodiments the tablet comprises about 50 wt. % extrudate.

In some embodiments, the tableting formulation of the disclosure comprises (i) the extrudate; (ii) the disintegration system; (iii) one or more diluents, in some embodiments it is preferred to select mannitol and microcrystalline cellulose as diluents; (iv) a glidant, in some embodiments it is preferred to use colloidal silica as a glidant; and (v), and one or more lubricants, in some embodiments it is preferred to use sodium stearyl fumarate as a lubricant.

In some embodiments, it is preferred for the compound of Formula I to be a compound of Formula Ia, or a salt thereof:

Formula Ia

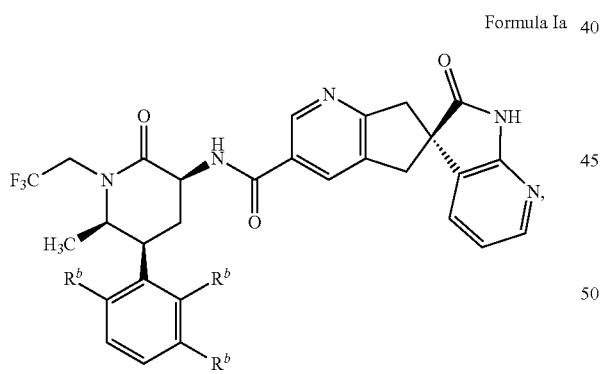

wherein each of "$R^b$" is —H or each of "$R^b$" is —F.

In some embodiments, preferably the water-soluble polymer matrix of said extrudate is a water-soluble polyvinylpyrolidone/vinyl acetate copolymer, preferably a polyvinylpyrolidone/vinyl acetate copolymer made by free-radical polymerization of a 6:4 ratio of vinylpyrrolidone:vinyl acetate monomer.

In some embodiments where the compound of Formula I is a compound of Formula Ia, preferably, the compound of Formula Ia is present in the extrudate from about 20 wt % of the extrudated to about 22 wt. % of the extrudate.

In some embodiments, preferably the extrudate comprises—tocepherol-polyethylene-glycolsuccinate (TPGS) as a dispersing agent, which is present in an amount comprising at least about 5 wt. % of the finished extrudate.

In some embodiments, preferably the extrudate comprises soluble polyvinylpyrolidone/vinyl acetate copolymer which is present in an amount comprising from about 50 wt. % of the extrudate to about 80 wt. % of the extrudate, preferably about 70 wt. % of the extrudate to about 75 wt. % of the extrudate.

In one aspect the present disclosure provides a formulation suitable for providing a pressed tablet, the formulation comprising:
 a) an extrudate composition comprising a water-soluble polyvinylpyrolidone/vinyl acetate copolymer (PVP-VA copolymer) matrix and dispersed therein:
  (i) an active compound of Formula Ia, or a pharmaceutically acceptable salt thereof:

Formula Ia

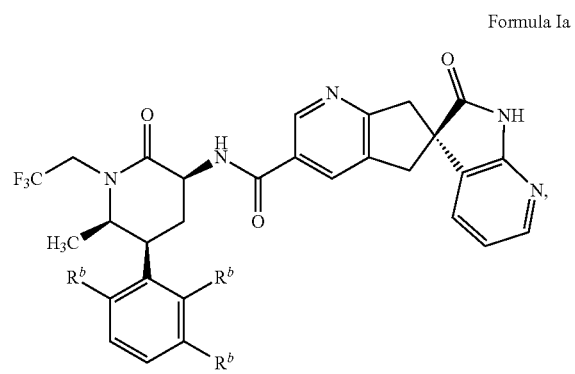

wherein all of $R^b$ are either —H or all of $R^b$ are —F; and
  (ii) tocepherol polyethylene glycol succinate (TPGS), wherein said compound of Formula Ia comprises from about 5 wt % to about 23 wt. % of said extrudate and TPGS comprises at least about 5 wt. % of said extrudate; and
 b) a disintegration system comprising: (i) croscarmellose sodium; and (ii) Powdered Sodium Chloride,
 wherein said disintegration system comprises about 20 wt. % of said formulation, and wherein said formulation is further characterized by providing a tablet having a hardness of from about 12 kP to about 18 kP, preferably about 12 kP to about 16 kP, which tablet when subjected to a dissolution test complying with USP 30 NF25 Chapt. 711, in a paddle-stirring apparatus equipped with USP 2 paddles, operated at 50 rpm, in 900 ml of simulated gastric fluid (pH 1.8) at 37° C. releases at least about 90% of the compound of Formula Ia contained therein in less than about 20 minutes.

In embodiments a tablet formulation of the disclosure comprises in addition to extrudate and disintegration system: (i) mannitol, preferably about 20 wt. % of the formulation; (ii) microcrystalline cellulose, preferably up to about 20 wt. % of the formulation; (iii) colloidal silica, preferably about 0.25 wt. % of the formulation; and (iv) sodium stearyl fumarate, preferably about 0.75 wt. % of the formulation. In some embodiments, preferably the tablet formulation comprises about 50 wt % of said extrudate.

In embodiments, the present disclosure provides an extruded composition (extrudate) comprising a soluble polymer matrix and dispersed or dissolved therein, a compound of Formula I, or a pharmaceutically acceptable salt thereof:

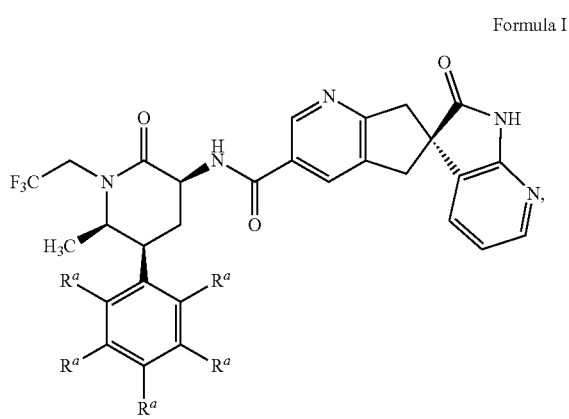

Formula I wherein $R^a$ is independently —H or —F, and a dispersing agent, for example, vitamin E polyethylene glycol succinate (TPGS), which extrudate is incorporated into a pharmaceutical formulation comprising a disintegration system, which formulation is suitable for providing tablets of up to 18 kP, in some embodiments, preferably 16 kP, hardness which disintegrate within about 5 minutes in standard disintegration tests.

Compound of Formula I suitable for use in compositions of the disclosure may be prepared in accordance with the synthesis described in WO 2012/064910. In some embodiments it is preferable to crystallize the crude compound of Formula I prepared in accordance with the foregoing from an ethanol/water solvent, thus providing a crystalline trihydrate form of the compound, and to mill the crystalline material to a particle size that provides a free-flowing powder which can be fed into the extruder equipment used in preparing the dispersion. As will be appreciated, where noted, weights and weight percentage relationships described for the compound of Formula I in formulations and tablets described herein are adjusted to reflect the weight of an equivalent amount of 100% active free-base of the compound without solvent of crystallization or inert material as would be taken into consideration when preparing the formulation using materials having less than 100% activity.

With reference to FIGS. 10 and 11, in general the extrudate is prepared by hot-melt extrusion (HME) of a compound of Formula I and various excipients which may or may not have received additional operations to render them suitable for HME processing.

It was surprisingly found that, contrary to common experience with Class II pharmaceutical compounds which are frequently dispersed in many different polymers, as discussed above, the compounds of Formula I tend to thermally degrade when attempts are made to incorporate them into a matrix comprising certain commercially available cellulosic polymers using HME techniques. For example, using HPMCAS as the polymer matrix leads to the formation of excessive degradation products in the dispersion produced. In some experiments, use of a cellulosic polymer as the dispersion matrix for preparing dispersions of the compound of Formula I by HME resulted in up to 25 times the amount of API degradation that subjecting the API alone to the same thermal excursion generated.

Surprisingly, it was found that one type of commercially available polymer material from which a dispersion of the compound of Formula I could be prepared without exacerbating thermal degradation of the compound was the commercially available water-soluble polymers, for example, polyvinylpyrrolidone/vinylacetate copolymers (PVP-VA polymers). It was surprisingly found that dispersions prepared by HME technique using a water-soluble polymer, for example a PVP-VA polymer and a compound of Formula I resulted in no greater thermal degradation than subjecting the raw compound of Formula I alone to the same thermal excursion. Accordingly, intimate mixtures of free base compound "FIa-H" (the compound of Formula Ia wherein all of "$R^a$" are —H,) or of the free base compound "FIa-F" (the compound of Formula Ia wherein all of "$R^a$" are —F) and one of two potential matrix polymers were subjected to 2 minutes of heating to 170° C. on a TGA instrument stage, then cooled to room temperature and evaluated spectroscopically for the formation of known thermal degradation products. This data is summarized in Table A.

TABLE A

| Composition | Initial mole % degradation products present | 170° C., 2 min. Mole % degradation products present |
| --- | --- | --- |
| FIa-H alone (crystalline material) | 0.18 | 0.18 |
| FIa-H alone (amorphous material) | 0.11 | 0.11 |
| FIa-F alone (amorphous material) | 0.11 | 0.11 |
| FIa-H + PVP-VA | 0.42 | 0.77 |
| FIa-H + HPMCAS | 0.15 | 3.57 |
| FIa-F + PVP-VA | 0.10 | 0.15 |
| FIa-F + HPMCAS | 0.08 | 2.25 |

As illustrated in Table A, these data indicate that some commercially available cellulosic polymers exacerbate thermal degradation of both the FIa-H compound and the FIa-F compound. Moreover, it was found that typically HME processing temperatures can reach 180° C., which results in even greater percentage of loss of a compound of Formula I to degradation products. Thus, the investigators surprisingly found that dispersing compounds of Formula I in soluble copolymers of polyvinylpyrrolidone/vinyl acetate copolymer (PVP-VA copolymer) using a hot-melt extrusion (HME) processing technique run with the same thermal excursions used when a cellulosic polymer was employed resulted in a reduction of degradation products detected in the extrudate product. Typically, the percentage increase of degradation product observed in such extrudate was no greater than the percentage of degradation product observed when samples of the same compound of Formula I was subjected to the same thermal excursion experienced in the HME process.

In accordance with the foregoing, suitable water-soluble polymers for use in compositions of the disclosure are any soluble PVP-VA copolymer which is made by free-radical polymerization of a 6:4 ratio of vinylpyrrolidone:vinyl acetate monomer. An example of commercially available copolymer of this type is the polyvinylpyrrolidone/vinylacetate copolymer sold under the trade name Kollidon® 64, and equivalents thereof.

In addition to a matrix polymer and at least one compound of Formula I, an extrudate of the present disclosure will include some amount of an excipient which acts as a dispersing agent. As the term is used herein a dispersing agent can reduce the thermal energy required to drive compound of Formula I into solution in the matrix polymer and promote formation of the dispersion with even lower degradation losses in the compound of Formula I dispersed in the matrix. For extrudates of the disclosure, in some embodiments it is preferred to employ vitamin E in the form of its polyethylene glycol succinate (d-alpha-tocopheryl polyethyleneglycol succinate, or TPGS, herein). An example of a commercially available TPGS suitable for use in extrudates of the present disclosure are any that provide esterified d-alpha-tocopheryl succinate with polyethylene glycol 1000, for example, but not limited to, Vitamin E d-TPGS NF from Eastman Chemical Company. In some embodiments, preferably TPGS is used as the dispersing agent and is present in the finished extrudate in an amount that is at least about 5 wt. % of the extruded composition.

It will be appreciated that other dispersing agents, for example, polyethoxylated castor oil (for example, cremophor) may also be employed.

The relative amount of the compound of Formula I, matrix polymer and dispersing agent employed in compositions of the disclosure, expressed as a wt. % of the extruded composition (extrudate), can vary and still be within the scope of the disclosure. Typically, the matrix polymer is present in an amount making up the balance of the composition after subtracting the wt. % of the API and dispersing agent. Typically the amount of matrix polymer is from about 70 wt. % to 75 wt. % of the finished extrudate. In some embodiments compositions of the present disclosure are preferred that include an amount of the compound of Formula I which, corrected for its relative activity in comparison to 100% pure freebase compound of Formula I, is equivalent to no more than 25 wt. % of 100% free-base compound contained within the finished extrudate composition. In some embodiments, preferably the amount of the compound of Formula I present in the finished extrudate is equivalent in activity to from about 5 wt. % to about 22 wt. % of 100% pure free-base compound in the finished extrudate, and more preferably an amount equivalent in activity to at least about 20 wt. % of the 100% free base compound in the finished extrudate.

Compositions of the present disclosure may be prepared by processes that are suitable for causing the selected API (for example, a compound of Formula Ia) to form a dispersion throughout the polymer matrix such that the drug is generally an amorphous uniform dispersion in the polymer or dissolved in the polymer. In general this requires some method of heating and mixing the constituents of the desired composition together and recovering the dispersion or solution in a solid form. Although it will be appreciated that any means affording a dispersion may be employed without departing from the present disclosure, in some embodiments it is preferred to prepare compositions of the present disclosure via Hot Melt Extrusion (HME). Hot melt extrusion (HME) is a technique in which an extruder, for example, a 27 mm Leistritz twin screw extruder, is employed to blend and heat the polymer, drug, and dispersing agent, whilst forming the finished composition dispersion or solution into a "noodle" or other conveniently handled shape which may be employed in further processing in the preparation of tableting formulations (extrudate).

In carrying out such operations, some or all of the components may be premixed prior to introducing them into the extruder, for example, by blending dry powders or wet milling or wet mixing, the constituents together in a blending, mixing or granulation process to insure intimately mixed constituents that lead to a homogeneous blend of constituents when the blend is fed into the extruder. Alternatively, the constituents may be fed into the extruder using independent feed streams (see Polymer Extrusion 4th Edition by Chris Rauwendaal 2001, Hanser Gardner Publications, Inc., Cincinnati, Ohio or Schenck et al., (2010), Achieving a Hot Melt Extrusion Design Space for the Production of Solid Solutions, in Chemical Engineering in the Pharmaceutical Industry: R&D to Manufacturing (ed. D. J. am Ende), John Wiley & Sons, Inc., Hoboken, N.J., USA). Although for some compositions of the present disclosure it is preferred to employ an HME process to prepare them, it will be appreciated that compositions of the disclosure can be prepared by any means useful for preparing a melt in any convenient apparatus in which an admixture of a compound of Formula I, matrix polymer and dispersing agent can be heated, mixed, and recovered.

In general, when extruding materials, the act of transporting the material through the extruder results in imparting energy to the material, which is converted to heat in the transported material. When heat transfer from the extruder power consumed in material transport is not by itself sufficient to achieve the temperature required to produce the desired dispersion or solution of a compound of Formula I in the polymer matrix, generally the barrel of the extruder is provided with means to impart additional heat to the material. In like manner, different sections of the extruder barrel can be heated or cooled, as needed, to maintain a particular temperature within a section of the extruder barrel or even extract heat in a different section of the extruder barrel to cool the material as it is passing through. In general the extruder temperature, power and transport speed of the extruder are set to provide the minimum temperature excursion and residence time needed to insure that a homogeneous dispersion or solution is prepared, thus minimizing the amount of API that undergoes degradation during processing.

In general, the extrudate emerging from an extruder is in a plastic state and solidifies upon emerging from the barrel due to pressure release and cooling. During this transition, typically the extrudate has a profile shape, for example, noodles, bars, cylinders, etc., and is "cut" into convenient length pieces. Once extrudate pieces are obtained, they can be further mechanically processed to provide a convenient form for incorporation into a dosage form, for example, by milling, grinding, or sieving. As the term is used herein, the material emerging from the extruder, and any form into which that material is subsequently rendered by mechanical processes, for example, milling, grinding, blending, sieving or granulating, is termed the "extrudate". Exemplary extruders include those provided by Leistritz, for example a 27 mm Leistritz twin screw extruder, and those provided by Thermo-Fisher, for example, a 16 mm twin screw Thermo-Fisher extruder. This equipment is generally equipped with means of heating the extruder barrel permitting it to be used in a "hot melt extrusion" operation.

Once the extrudate is rendered into a convenient form for further processing, it can be incorporated into a formulation for use in providing a dosage form suitable for oral administration, for example, a formulation adapted for pressing into tablets or filling into capsules. To achieve the dissolution and disintegration targets needed for effectively administering a compound of Formula I in the provision of migraine therapy, a formulation is prepared which comprises the finished extrudate, preferably milled to provide a powdered form that is easily blended with the other constituents of the formulation, a disintegration system and other excipients, for example diluent and lubricant, useful in preparing a formulation suitable for tableting. For use in a formulation of the present disclosure, the disintegration system comprises a conventional disintegrant, for example, croscarmellose sodium or crospovidone, and Powdered Sodium Chloride, where "Powdered Sodium Chloride" has the meaning presented herein.

For use in a disintegration system of the present disclosure, the phrase "Powdered Sodium Chloride" means sodium chloride which has been processed to a form having a particle distribution which yields the following values: (i) d50 of less than about 210 microns, for example, about 195 microns; (ii) d10 of less than about 50 microns, for example, between 43 microns and 44 microns; (iii) a d90 of less than about 470 microns, for example, about 460 microns, and wherein the material displays a volume mean diameter of less than about 240 microns, for example, about 230 microns. An example of one such type of sodium chloride which is commercially available is provided by Avantor™ under the product designation "Sodium Chloride, Powder, USP GenAR® product no. 7540".

The data shown in Table II illustrate the need to employ Powdered Sodium Chloride in the disintegration system in formulations of the disclosure. Accordingly, test tablets comprising an extrudate of the disclosure (said extrudate comprising PVP-VA matrix, a compound of Formula Ia (FIa-H), and TPGS), a diluent comprising microcrystalline cellulose and a disintegration system consisting of crosscarmellose sodium and the salt shown in the left-hand column of Table II were subjected to a disintegration test complying with USP 31-NF26 Chapt. 701 in a standard disintegration testing apparatus (Pharamatron DT50) using aqueous HCl (pH 1.8) as a disintegration medium at 37° C. As reflected in Table B, surprisingly, only the tablet employing the Powdered Sodium Chloride in the disintegration system was able to meet the disintegration target of less than 5 minutes (tablet compression force controlled to provide tablets of consistent hardness and thickness for all formulations).

TABLE B

| Salt in Disintegration System | Disintegration time, aqueous HCl (pH 1.8) |
| --- | --- |
| None | Greater than 1 hour |
| Powdered Sodium Chloride | 1.5 minutes |
| Granular potassium carbonate | 6 minutes |
| Granular sodium chloride | 18 minutes |
| Granular sodium carbonate | 13 minutes |
| Powdered sodium bicarbonate | 17 minutes |
| Powdered sodium sulfate | 20 minutes |
| Granular sodium phosphate (dibasic) | 22 minutes |

Moreover, when equivalent tablets were made using Powdered Sodium Chloride alone, without croscarmellose sodium, it was found that tablet disintegration times exceeded 5 minutes as well. Accordingly, in some embodiments it is preferable that the disintegration system comprise a conventional disintegrant in conjunction with Powdered Sodium Chloride, and more preferably in a weight ratio of 1:1, Powdered Sodium Chloride:Disintegrant. Without being bound by theory, it is believed that the Powdered Sodium Chloride exhibits dissolution kinetics that are rapid compared with the rate of gelation of the polymer matrix when a tablet of the disclosure is exposed to the intended dissolution environment (human GI tract). Again without being bound by theory, the Powdered Sodium Chloride is believed by virtue of its particulate profile to have a combination of desirable dissolution kinetics and ability to form with sufficient rapidity (more rapidly than the rate of gelation of the matrix polymer) a local boundary layer of sufficient ionic strength to suppress gel-formation in the matrix polymer, and thereby to facilitate release of a compound of Formula I from the tableted formulation, which would otherwise be inhibited by gel formation in the matrix polymer. It will be appreciated that other salts if provided in a form which displays the same combination of rapid dissolution kinetics and the ability to rapidly form a local boundary layer of sufficient ionic strength to suppress gelation can also be employed in a formulation of the disclosure without departing from the scope of the disclosure defined herein.

In formulations of the disclosure, a suitable disintegrant for use in disintegration systems of the disclosure is, for example, croscarmellose sodium (crosslinked sodium carboxymethylcellulose polymer), for example, the AC-Di-Sol® line of polymers available from FMC. It will be appreciated that other disintegrants may be employed to provide an effective disintegration system, for example, crospovidone, if they are used in accordance with the other aspects of the disintegration system described herein and not depart from the scope of the disclosure.

The compounds of Formula I are directed to treatment of migraine, and as such, a rapid-release formulation is thought to be important in providing a therapeutic benefit to human patients to whom such a tablet is administered.

As is known, two qualities of tablet and capsule dosage forms important to release of an active pharmaceutical compound therefrom may be demonstrated using standard tests to measure the disintegration time and/or the dissolution time of the dosage form. A disintegration test measures the amount of time required for the dosage form to visibly disintegrate and wash out of a standard basket contained in a standard apparatus under standard operating conditions. A standard disintegration test is described for tablets and capsules in USP 31-NF26, Chapt. 701, beginning at p 266. There are equivalents thereto described in, for example, the European Pharmacopoeia and the Japanese Pharmacopoeia, which standard tests are generally accepted in the regulatory bodies of most countries. As the term is used herein with reference to formulations and tablets of the disclosure, "disintegration time" means: as determined in accordance with a test complying with this standard run at 37° C. using aqueous HCl (pH 1.8) as a disintegration fluid.

Dosage forms intended for oral administration may also be measured in a dissolution test, wherein the time-rate release of an amount of therapeutic compound dissolved into a standard media in a standard apparatus is measured after introducing the dosage form into the testing medium. A standard dissolution test for tablets and capsules is described in, for example, USP 36, chapt 711. Equivalent tests are described in the European Pharmacopoeia and the Japanese Pharmacopoeia, and in guidance from the US FDA, for example, in "Guidance for Industry, Dissolution Testing of Immediate Release Solid Oral Dosage Forms" published August 1997 by the U.S. Department of Health and Human Services, Food and Drug Administration, Center for Drug Evaluation and Research, pp 1-13 and references therein. As the term is used herein with reference to formulations and tablets of the disclosure, "dissolution time" means: as determined in accordance with a test complying with this standard in a standard dissolution apparatus equipped with USP 2 paddles, operated at 50 rpm, in 900 ml of simulated gastric fluid (pH 1.8) at 37° C.

In one aspect the disclosure provides a formulation adapted to preparing tablets comprising an extrudate of the disclosure, a disintegration system comprising Powdered Sodium Chloride and croscarmellose sodium, and other excipients, for example, diluents, glidants and lubricants, in amounts that, once the formulation is pressed into a table having a hardness of from about 12 kP to about 16 kP, and in some embodiments, 12 kP to about 18 kP, provides a tablet releasing more than 90% of the API contained therein in less than about 20 minutes when subjected to dissolution testing in a standard dissolution apparatus equipped with USP 2 paddles, operated at 50 rpm, in 900 ml of simulated gastric fluid (pH 1.8) at 37° C., in accordance with the procedures outlined in "Guidance for Industry, Dissolution Testing of Immediate Release Solid Oral Dosage Forms" published August 1997 by the U.S. Department of Health and Human Services, Food and Drug Administration, Center for Drug Evaluation and Research, pp 1-13 and references therein where the tablet hardness exceeds.

Where tablet hardness is used herein, it is in reference to a tablet having a 500 mg target weight and a caplet shape or a 652.2 mg target weight in a caplet shape. Accordingly, as the term is used herein, tablets having a hardness in the range of 12 kPa to 16 kPa have a corresponding tensile strength of about 1.75 MPa, and tablets having a hardness in the range of 19 kPa to 22 kPa have a tensile strength of about 2.75 Mpa.

Formulations of the disclosure used in preparation of oral dosage forms (i.e., tablets or capsules) may further comprise other excipients. For example: a typical formulation of the disclosure directed to the preparation of a pressed tablet may contain a diluent (for example, mannitol, article of commerce, and/or microcrystalline cellulose, for example Avicel®); a glidant (for example, colloidal silica, for example Cab-O-Sil®); and a lubricant (for example, sodium stearyl fumarate, article of commerce). It will be appreciated that in formulating compositions of the disclosure, other diluents, glidants, and lubricants may be substituted to effect similar formulations.

The following definitions apply to excipients which may be used in formulations of the disclosure as the terms are used herein:
  a diluent is an excipient which increase the bulk of a dosage form, typically where the active pharmaceutical ingredient in the formulation is too potent to permit convenient processing or administration of a dosage form which does not include a diluent, or where the formulation by itself without a diluent makes formation of the dosage form difficult (for example, where an aliquot of the formulation without a diluent would be of too small of a volume to form the aliquot into a tablet);
  a disintegrant is an excipient that expands and/or dissolves when placed in an aqueous environment, for example, the gastrointestinal tract, which aids a tablet in breaking apart and promotes release of an active pharmaceutical ingredient contained in a tablet;
  a "disintegration system" is a combination of a conventional disintegrant and a rapidly dissolving salt which provides beneficial antigellation effects when placed into an environment in which the dosage form within which the disintegration system is incorporated is placed into an environment in which the dosage form disintegrates, for example, simulate gastric fluid, the gastrointestinal tract of a subject or aqueous HCl at pH 1.8;
  a Glidant is an excipient, for example colloidal silica, that enhances the flow of a granular mixture by reducing interparticle friction.

Pharmaceutical formulations intended for the preparation of oral dosage forms (tablets and capsules) may further contain one or more agents selected from the group consisting of sweetening agents, flavoring agents, coloring agents, and preserving agents to provide pharmaceutically elegant and palatable preparations.

The preparation of formulations of the disclosure suitable for use in providing solid oral dosage forms comprising a composition of the disclosure may involve blending, roller compaction or wet granulation to densify and/or reduce the risk of segregation of components during subsequent handling (e.g., compression into tablets). Granulation steps can also be used to minimize the impact of raw material property variability (e.g., excipient particle size) on subsequent processing (e.g., tablet compression) and ultimate product performance. Lubrication is typically performed prior to roller compaction and tablet compression to reduce the tendency of material to adhere to compression surfaces (e.g., tablet tooling). In general lubricants are derivatives of stearic acid, for example, magnesium stearate or sodium stearly fumarate. Techniques and methods useful in preparation of dosage forms are know, for example, as described in Ansel, Introduction to Pharmaceutical Dosage Forms, Seventh Edition, 1999.

In general, preparation of oral dosage forms from pharmaceutical formulations of the disclosure requires that the pharmaceutical formulation of the disclosure (admixture of excipients, disintegrating system and composition of the disclosure) is compressed into a tablet or charged into a capsules. Tablets can be prepared with a variety of possible shapes (ellipsoidal, capsule, biconvex round, etc.). The powder can also be encapsulated in capsule dosage (e.g., using hard gelatin capsules). Techniques suitable for preparing solid oral dosage forms of the present disclosure are described in Remington's Pharmaceutical Sciences, 18th edition, edited by A. R. Gennaro, 1990, Chapter 89 and in Remington—The Science and Practice of Pharmacy, 21st edition, 2005, Chapter 45. In some embodiments of the present disclosure, it is preferred to prepare a tablet having a hardness of 16 kP or less, where the tablet has a target of providing the equivalent of 50 mg of a compound of Formula Ia (100% freebase), by placing 462.5 to 537.5 mg of the formulation into tableting tooling having an Elizabeth Carbide Die Company™ drawing number P-14305-B and pressing it in a Korsch™ tableting press.

With reference to FIG. 12, in general, compositions of the disclosure are prepared by dry-blending various excipients with milled dispersion (soluble polymer matrix comprising API dispersed therein), and compressing the blend to tablets.

EXAMPLES

Example 1

A phase 1, multicenter, open-label, single-dose, non-randomized, parallel-group study was conducted to assess the PK, safety, and tolerability profile of 100 mg ubrogepant in healthy participants with normal hepatic function and patients with impaired hepatic function after a single dose administration. The study was intended to enroll 24 male and female participants with hepatic impairment (8 mildly impaired, 8 moderately impaired, and 8 severely impaired) and 8 healthy male and female participants with normal hepatic function, aged 18 through 75 years, who were matched closely to the age, weight, and gender of the hepatically impaired groups.

Ubrogepant is mainly metabolized by hepatic CYP enzymes, and thus it is likely that patients with varying degrees of hepatic impairment may achieve higher systemic concentrations of ubrogepant. Accordingly, this study characterized the PK profile of ubrogepant in patients with mild, moderate, or severe hepatic impairment as compared to participants with normal hepatic function.

All participants received a single oral dose of 100 mg ubrogepant under fasted conditions on Day 1.

Participants with hepatic impairment were categorized according to the Child-Pugh classification. Participants with moderate hepatic impairment (Child-Pugh B classification) were not enrolled until 4 patients with mild hepatic impairment (Child-Pugh A classification) had completed the study; participants with severe hepatic impairment (Child-Pugh C classification) were not to be enrolled until 4 patients with moderate hepatic impairment had completed the study. Enrollment for the moderate and severe hepatic impairment groups began after the safety/tolerability/PK profile of ubrogepant was established by the medical safety physician and the clinical pharmacologist. Healthy participants with normal hepatic function were recruited after participants with hepatic impairment had been enrolled in the study, in order to match them as closely as possible to the hepatically impaired participants with respect to age, weight, and gender. Participants with normal hepatic function were matched specifically according to age, not to exceed 5 years between the means of the normal group and the 3 hepatically impaired groups. Weight range deviated <20% between the means of the normal group and the 3 hepatically impaired groups; and gender, as much as possible to match the ratio of the normal hepatic function group to the 3 hepatically impaired groups.

The planned duration of each participant's participation in the study was 4 days (Day −1 through the last PK sample on Day 3), excluding the screening period and 30-day follow-up period.

The study design was chosen in accordance with the requirements of the FDA guidance "Pharmacokinetics in Patients with Impaired Hepatic Function: Study Design, Data Analysis, and Impact on Dosing and Labeling" (U.S. Food and Drug Administration, 2003).

Participants received a single oral dose of 100 mg (2×50 mg tablets) of ubrogepant with 240 mL of water at approximately 0800 hours on Day 1 following an overnight fast. Fasting continued for 4 hours after dosing. Because minimal to no accumulation was expected after once daily repeated dosing for ubrogepant, a single-dose study was considered adequate to satisfy the objectives of the present study.

Participants were queried regarding any AEs or SAEs at the time of each vital sign assessment, as well as at each visit through to the follow-up visit.

Study center personnel were required to report any participant who met potential Hy's Law criteria anytime from the time he or she signed the ICF for the study, until 30 days after the last dose of ubrogepant. Criteria for potential Hy's Law cases were as follows: AST or ALT≥3×ULN and Total Bilirubin≥2×ULN and Alkaline phosphatase<2×ULN.

A total of 28 participants (8 participants each in the healthy, mild, and moderate hepatic impairment groups and 4 in the severe hepatic impairment group) were enrolled in the study. Due to challenges finding sufficient participants with severe hepatic impairment, enrollment was stopped after 4 of the planned 8 participants in the group had entered the study. All 28 participants received IP as planned and completed the study. No participant discontinued from the study prematurely.

Demographics and baseline characteristics are summarized in Table 1.

TABLE 1

Summary of Demographic and Baseline Characteristics (Safety Population)

| | | Hepatic Impairment | | | |
|---|---|---|---|---|---|
| Parameter | Normal Hepatic Function (n = 8) | Mild (N = 8) | Moderate (N = 8) | Severe (N = 4) | Total N = 28 |
| Age (years) | | | | | |
| Mean (SD) | 58.1 (2.8) | 54.0 (8.3) | 57.8 (7.6) | 57.0 (9.6) | 56.7 (6.9) |
| Median | 59.5 | 56.0 | 58.0 | 58.0 | 58.5 |
| Min, Max | 54, 61 | 36, 62 | 45, 70 | 46, 66 | 36, 70 |
| Sex, n (%) | | | | | |
| Male | 4 (50.0) | 2 (25.0) | 5 (62.5) | 3 (75.0) | 14 (50.0) |
| Female | 4 (50.0) | 6 (75.0) | 3 (37.5) | 1 (25.0) | 14 (50.0) |
| Race, n (%) | | | | | |
| White | 8 (100.0) | 8 (100.0) | 6 (75.0) | 4 (100.0) | 26 (92.9) |
| Black/African American | 0 | 0 | 1 (12.5) | 0 | 1 (3.6) |
| Multiple | 0 | 0 | 1 (12.5) | 0 | 1 (3.6) |
| Ethnicity | | | | | |
| Hispanic or Latino | 5 (62.5) | 4 (50.0) | 5 (62.5) | 3 (75.0) | 17 (60.7) |
| Not Hispanic or Latino | 3 (37.5) | 4 (50.0) | 3 (37.5) | 1 (25.0) | 11 (39.3) |
| Weight | | | | | |
| Mean (SD) | 79.41 (8.37) | 85.00 (16.82) | 85.14 (22.63) | 85.75 (8.09) | 83.55 (15.45) |
| Median | 76.20 | 86.70 | 80.75 | 86.00 | 80.00 |
| Min, Max | 148.0, 182.0 | 157.0, 172.3 | 155.5, 176.0 | 155.0, 182.0 | 148.0, 182.0 |

TABLE 1-continued

Summary of Demographic and Baseline Characteristics (Safety Population)

| | | Hepatic Impairment | | | |
|---|---|---|---|---|---|
| Parameter | Normal Hepatic Function (n = 8) | Mild (N = 8) | Moderate (N = 8) | Severe (N = 4) | Total N = 28 |
| | | Height | | | |
| Mean (SD) | 167.76 (11.15) | 164.48 (5.31) | 168.50 (6.71) | 168.88 (11.05) | 167.19 (8.25) |
| Median | 166.55 | 166.25 | 169.50 | 169.25 | 167.50 |
| Min, Max | 148.0, 182.0 | 157.0, 172.3 | 155.5, 176.0 | 155.0, 182.0 | 148.0, 182.0 |
| | | Body Mass Index (km/m$^2$) | | | |
| Mean (SD) | 28.28 (2.35) | 31.32 (5.39) | 29.94 (7.54) | 30.26 (4.05) | 29.91 (5.19) |
| Median | 28.03 | 31.86 | 27.90 | 29.56 | 28.81 |
| Min/Max | 25.7, 33.3 | 22.4, 41.3 | 20.4, 41.6 | 26.2, 35.8 | 20.4, 41.6 |

Participants with hepatic impairment were allowed to continue taking medications prescribed for their hepatic disease or other concurrent diseases common in this population. No concomitant medications were administered to participants with normal hepatic function during the study.

PK sampling was done at the following times to determine ubrogepant plasma concentrations: starting on Day 1 at 0 hour (predose) and 0.5, 1.0, 1.5, 2, 3, 4, 5, 6, 8, 12, 14, 24, 30, 36, and 48 hours post dose. Sampling was also done at the following times for plasma protein binding determinations: Day 1 at 0 hour (predose) and 2 hours post dose.

A summary of the mean PK parameters for ubrogepant when administered to participants with varying degrees of hepatic impairment and in participants with normal hepatic impairment is presented in Table 2.

TABLE 2

Mean (±SD) Ubrogepant Pharmacokinetic Parameters Following Single Dose Oral Administration of Ubrogepant 100 mg in Participants with Mild, Moderate, or Severe Hepatic Impairment and in Participants with Normal Hepatic Function (PK Population)

| PK Parameter | Mild Hepatic Impairment Group | Moderate Hepatic Impairment Group | Severe Hepatic Impairment Group | Normal Hepatic Function Group |
|---|---|---|---|---|
| $C_{max}$ (ng/ml) | 411.36 ± 189.51 | 479.96 ± 188.78 | 509.27 ± 75.78 | 405.76 ± 218.89 |
| $AUC_{0-t}$ (ng · h/mL) | 1745.23 ± 767.40 | 2784.87 ± 2021.70 | 3310.82 ± 704.12 | 1587.83 ± 529.76 |
| $AUC_{0-inf}$ (ng · h/mL) | 1764.09 ± 775.00 | 2815.22 ± 2056.88 | 3327.31 ± 704.93 | 1598.02 ± 532.55 |
| $T_{max}$ (h)$^a$ | 1.50 (1.00-2.00) | 2.00 (1.00-3.00) | 1.50 (0.50-2.00) | 1.75 (1.00-4.00) |
| $t_{1/2}$ (h) | 6.56 ± 5.93 | 5.95 ± 2.68 | 5.62 ± 0.62 | 5.60 ± 3.68 |
| $V_z/F$ (L) | 558.70 ± 358.39 | 365.19 ± 129.63 | 248.14 ± 29.93 | 532.88 ± 319.83 |
| CL/F (L/h) | 66.38 ± 26.15 | 49.78 ± 23.84 | 31.23 ± 7.49 | 69.01 ± 23.54 |

$^a$Median (min-max)

Participants with mild hepatic impairment had 4% higher $C_{max}$ and 7% higher $AUC_{0-\infty}$ when compared to participants with normal hepatic function after administration of a single oral dose of 100 mg ubrogepant. The increase in $C_{max}$ and $AUC_{0-\infty}$ was slightly higher in participants with moderate hepatic impairment, with a 25% higher $C_{max}$ and 52% higher $AUC_{0-\infty}$. As compared to participants with normal hepatic function, those with severe hepatic impairment showed a significantly higher $C_{max}$ and $AUC_{0-\infty}$ of 40% and 115%, respectively.

A summary of comparison of plasma ubrogepant pharmacokinetic parameters following single dose oral administration of 100 mg ubrogepant in participants with mild, moderate, or severe hepatic impairment to participants with normal hepatic function (PK Population) is shown in Table 3.

TABLE 3

Summary of Comparison of Plasma Ubrogepant Pharmacokinetic Parameters Following Single Dose Oral Administration of 100 mg Ubrogepant in Participants with Mild, Moderate, or Severe Hepatic Impairment to Participants with Normal Hepatic Impairment

| Hepatic Function Group | PK Parameter | Geometric LSM | | Ratio of Geometric Means Test/ Reference | 90% Lower CI | 90% Upper CI |
|---|---|---|---|---|---|---|
| | | Test | Reference (Normal Hepatic Function) | | | |
| Mild-Impaired | $C_{max}$ (ng/mL) | 375.33 | 359.86 | 1.04 | 0.72 | 1.51 |
| | $AUC_{0-t}$ (ng · h/mL) | 1608.58 | 1512.10 | 1.06 | 0.72 | 1.57 |
| | $AUC_{0-\infty}$ (ng · h/mL) | 1625.33 | 1522.28 | 1.07 | 0.72 | 1.58 |
| Moderate-Impaired | $C_{max}$ (ng/ml) | 449.39 | 359.86 | 1.25 | 0.86 | 1.81 |
| | $AUC_{0-t}$ (ng · h/mL) | 2299.44 | 1512.10 | 1.52 | 1.03 | 2.24 |
| | $AUC_{0-\infty}$ (ng · h/mL) | 2319.45 | 1522.28 | 1.52 | 1.03 | 2.25 |
| Severe-Impaired | $C_{max}$ (ng/mL) | 505.35 | 359.86 | 1.40 | 0.89 | 2.21 |
| | $AUC_{0-t}$ (ng · h/mL) | 3249.97 | 1512.10 | 2.15 | 1.33 | 3.46 |
| | $AUC_{0-\infty}$ (ng · h/mL) | 3266.51 | 1522.28 | 2.15 | 1.33 | 3.46 |

Figure 1:
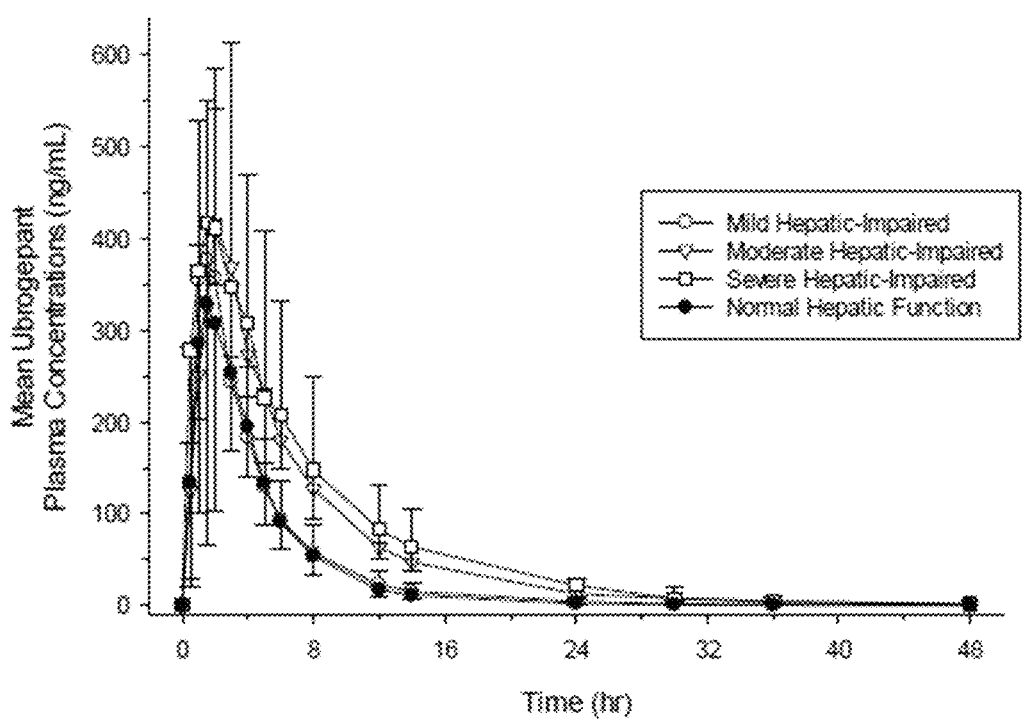
FIG. 1 shows the mean plasma concentration-time profiles following a single oral dose administration of 100 mg ubrogepant in participants with mild, moderate, or severe hepatic impairment and in participants with normal hepatic function as a linear scale.
Figure 2:
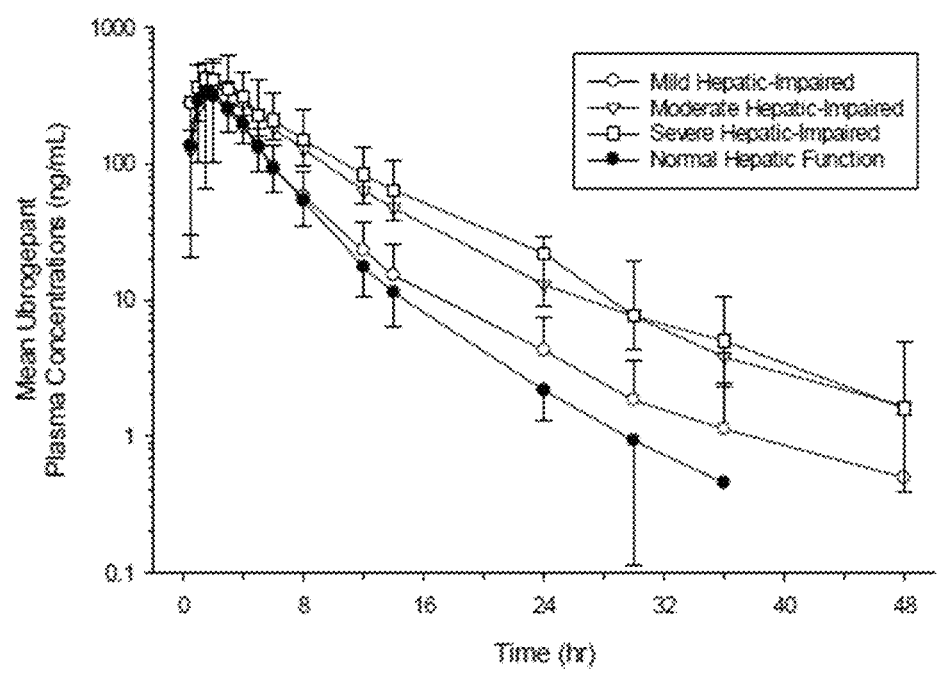
FIG. 2 shows the mean plasma concentration-time profiles following single oral dose administration of 100 mg ubrogepant in participants with mild, moderate, or severe hepatic impairment and in participants with normal hepatic function as a semilogarithmic scale. The rate and extent of ubrogepant systemic exposure was significantly higher in participants with severe hepatic impairment compared to patients with normal hepatic function; moderately higher in participants with moderate hepatic impairment; and slightly higher in participants with mild hepatic impairment.

FIGS. 1 and 2 show the mean plasma concentration-time profiles following single oral dose administration of 100 mg ubrogepant in participants with mild, moderate, or severe hepatic impairment and in participants with normal hepatic function (N=8 in each group, N=4 in severe hepatic impairment group). FIG. 1 shows a Linear Scale, and FIG. 2 shows a semilogarithmic scale.

Protein binding blood samples were collected from all participants starting on Day 1 at 0 hour (predose) and at 2 hours post-dose. The pre-dose samples collected prior to dosing for each participants were spiked with known quantities of ubrogepant. Percent bound ubrogepant was determined using equilibrium dialysis in the 2-hour sample.

Percentage of bound ubrogepant is summarized in Table 4. As shown in Table 4, in participants with mild, moderate, and severe hepatic impairment administered a single oral dose of 100 mg ubrogepant, percentage of protein-bound ubrogepant was 89.9%, 88.2%, and 85.3%, respectively, as compared to 89.3% in participants with normal hepatic function. Thus, plasma protein binding was generally similar across the mild and moderate hepatic impairment groups and in participants with normal hepatic function, and somewhat lower in participants with severe hepatic impairment.

TABLE 4

Summary of Ubrogepant Plasma Bound Protein-Binding in Participants with Mild, Moderate, or Severe Hepatic Impairment and in Participants with Normal Hepatic Function Following a Single Dose Oral Administration of 100 mg Ubrogepant (PK Population)

| Hepatic Function Group | 0 hr | 2 hr |
|---|---|---|
| Mild-Impaired | 88.87 ± 1.12 | 89.85 ± 1.33 |
| Moderate-impaired | 87.42 ± 1.89 | 88.24 ± 1.02 |
| Severe-Impaired | 84.58 ± 0.91 | 85.27 ± 0.94 |
| Normal Hepatic Function | 88.52 ± 0.84 | 89.28 ± 1.54 |

Overall, there was no clinically relevant change in the PK of ubrogepant in participants with mild and moderate hepatic impairment.

The rate ($C_{max}$) and extent ($AUC_{0-\infty}$) of ubrogepant systemic exposure was significantly higher (40% and 115%, respectively) in participants with severe hepatic impairment compared with participants with normal hepatic function. In participants with moderate hepatic impairment, a 25% higher $C_{max}$ and 52% higher $AUC_{0-\infty}$ was observed compared to participants with normal hepatic function. Mean $C_{max}$ and $AUC_{0-\infty}$ were slightly higher in participants with mid hepatic impairment compared to participants with normal hepatic function.

Plasma protein binding did not change in participants with mid and moderate hepatic impairment when compared to participants with normal hepatic function but decreased slightly in participants with severe hepatic impairment.

No deaths, SAEs, or withdrawals due to AEs occurred during the study. AEs occurred in a minority of study participants. Table 5 presents a summary of adverse events.

TABLE 5

Overall Summary of Adverse Events (Safety Population)

| | Normal Hepatic Function (N = 8) n (%) | Hepatic Impairment | | |
|---|---|---|---|---|
| | | Mild (n = 8) n (%) | Moderate (n = 8) n (%) | Severe (n = 4) n (%) |
| Any TEAE | 0 | 3 (37.5) | 2 (25.0) | 0 |
| Any treatment-related TEAE | 0 | 2 (25.0) | 2 (25.0) | 0 |
| Any SAE | 0 | 0 | 0 | 0 |
| AE leading to study discontinuation | 0 | 0 | 0 | 0 |
| Deaths | 0 | 0 | 0 | 0 |

Five participants (17.9%) had TEAEs during the study. The only AE experienced by more than a single participant was headache, in 2 participants.

Table 6 provides an overall summary of adverse events by hepatic function group, system organ class, and preferred term (safety population).

TABLE 6

Overall Summary of Adverse Events by Hepatic Function Group, System Organ Class, and Preferred Term (Safety Population)

| | Normal Hepatic Function (N = 8) n (%) | Hepatic Impairment | | |
|---|---|---|---|---|
| | | Mild (n = 8) n (%) | Moderate (n = 8) n (%) | Severe (n = 4) n (%) |
| Any TEAE | 0 | 3 (37.5) | 2 (25.0) | 0 |
| Gastrointestinal Disorders | 0 | 2 (25.0) | 0 | 0 |
| Diarrhoea | 0 | 1 (12.5) | 0 | 0 |
| Dyspepsia | 0 | 1 (12.5) | 0 | 0 |
| Nervous System Disorders | 0 | 1 (12.5) | 2 (25.0) | 0 |
| Headache | 0 | 1 (12.5) | 1 (12.5) | 0 |
| Dizziness | 0 | 0 | 1 (12.5) | 0 |

No deaths, SAEs, or withdrawals due to AE occurred during the study. AEs of mild to moderate intensity occurred in 5 of 28 participants (17.9%) with mild or moderate hepatic impairment. The only AE experienced by more than a single participant was headache, in 2 of 28 participants (7.1%). Both headaches were mild, self-limiting events that resolved within a day and without intervention. There were no clinically relevant changes in laboratory parameters, vital signs, or ECG measurements.

Ubrogepant was well-tolerated in healthy participants and in participants with mild to severe hepatic impairment. The incidence of treatment emergent AEs was low (17.9% overall) with only mild headaches occurring in more than one participant (2 participants total). No deaths, SAEs, or withdrawals due to AEs occurred during the study. There was no indication of worsening tolerance with increasing hepatic impairment.

Example 2

Clinical drug interaction studies were conducted to assess the impact of CYP3A4 modulators on the PK of ubrogepant. In particular, two phase 1, open-label, fixed-sequence, single-center crossover trials enrolled healthy adults to receive ubrogepant 20 mg with/without verapamil 240 mg (a moderate CYP3A4 inhibitor) or ketoconazole 400 mg (a strong CYP3A4 and P-gp inhibitor) (Study A), or ubrogepant 100 mg with/without rifampin 600 mg (a strong CYP3A4 and P-gp inducer) (Study B).

Outcomes included ubrogepant PK parameters (area under plasma concentration-time curve, time 0 through infinity [$AUC_{0-\infty}$], peak plasma concentration [$C_{max}$]) and safety (Treatment emergent adverse events [TEAEs]). PK parameters were compared between ubrogepant with/without coadministered medications using linear mixed-effects models. $C_{max}$ and $AUC_{0-\infty}$ least squares geometric mean ratios (GMR) of ubrogepant with/without coadministration were constructed.

Study A (verapamil and ketoconazole) comprised 3 treatment periods. In period 1, participants received a single oral dose of ubrogepant 20 mg on day 1 (dosed as two 10 mg tablets). Period 2 commenced at least 3 days after period 1 dosing, and participants received oral doses of verapamil 240 mg once daily (QD) for 7 days with a single oral dose of ubrogepant 20 mg coadministered on day 5. In period 3, which started at least 14 days after the last dose of verapamil in period 2, participants received oral doses of ketoconazole 400 mg QD for 5 days with a single dose of ubrogepant administered on day 2. Ubrogepant was administered under fasted conditions.

Study B (rifampin) had two treatment periods. In period 1, participants received a single oral dose of ubrogepant 100 mg on day 1 (dosed as two 50 mg tablets). Period 2 began after a washout of at least 8 days, and participants received an oral dose of rifampin 600 mg QD for 5 days (days 9-13) with a single oral dose of ubrogepant 100 mg coadministered with rifampin 600 mg on day 14. All treatments were received under fasted conditions.

Healthy adults aged 19-50 years for Study A and 18-45 years for Study B were eligible to participate. Participants had to be continuous nonsmokers without nicotine-containing product use for at least 3 months before dosing in Study A or the previous 2 years for Study B. For Study A, participants had to have a body mass index between 18.5 and 32.0 kg/m$^2$. For study B, participants had to have a BMI between 18.0 and 30 kg/m$^2$. Exclusion criteria for both studies included hypersensitivity to any study drug; exposure to hepatitis B virus, hepatitis C virus, or HIV; or use of any drug or substance known to affect CYP enzymes or P-gp.

Twelve participants enrolled in Study A and 30 enrolled in Study B. In Study A, 11 of 12 participants completed the trial. One participant completed all study procedures except for follow-up (discontinued due to a fatal motor vehicle accident prior to follow-up). Twenty-seven of 30 participants completed study B. Three participants discontinued the trial because of loss to follow up (n=1) and participant decision (n=2). In both studies, most participants were male (58% in Study A, 60% in study B) and most were white (83% in study A, and 87% in study B). The PK and safety analysis sets comprised all 12 participants in Study A and all 30 participants in Study B.

The results of these studies are summarized in Table 7.

TABLE 7

Drug Interactions with CYP3A4 Modulators

| CYP3A4 Modulator | PK Parameter | GMR | 90% Lower CI | 90% Upper CI |
|---|---|---|---|---|
| Verapamil | $C_{max}$ | 2.80 | 2.48 | 3.15 |
| (Moderate inhibitor) | $AUC_{inf}$ | 3.53 | 3.32 | 3.75 |
| Ketoconazole | $C_{max}$ | 5.32 | 4.19 | 6.76 |
| (Strong inhibitor) | $AUC_{inf}$ | 9.65 | 7.27 | 12.81 |
| Rifampin (Strong | $C_{max}$ | 0.31 | 0.27 | 0.36 |
| inducer) | $AUC_{inf}$ | 0.22 | 0.20 | 0.24 |

Figure 3:
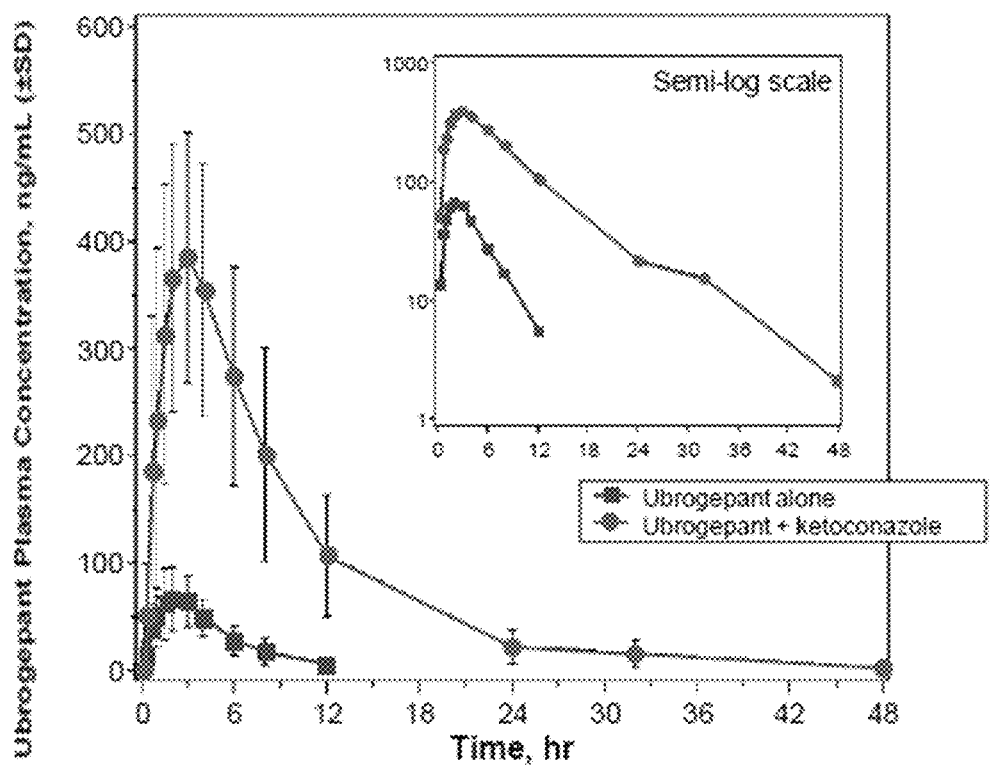
FIG. 3 shows plasma concentration-time profiles of single-dose ubrogepant 20 g alone and following coadministration with multiple doses of ketoconazole 400 mg, a strong CYP3A4 and P-gp inhibitor.

Plasma concentration-time profiles of single-dose ubrogepant 20 mg alone and following coadministration with multiple doses of ketoconazole 400 mg (a strong CYP3A4 and P-gp inhibitor) are shown in FIG. 3. Ketoconazole appeared to have substantially increased the levels of ubrogepant, resulting in a 9.7-fold increase in ubrogepant $AUC_{inf}$ and a 5.3-fold increase in ubrogepant $C_{max}$. Terminal tin of ubrogepant was longer when coadministered with ketoconazole (5.9 hours) compared with ubrogepant administered alone (2.5 hours). PK parameters of ubrogepant alone or coadministered with ketoconazole are shown in Table 8.

TABLE 8

PK Parameters of Ubrogepant alone or coadministered with ketoconazole (n = 12)

| PK Parameter | Ubrogepant | Ubrogepant + Ketoconazole | GMR (90% CI) |
|---|---|---|---|
| $AUC_{0-\infty}$ ng · h/mL, mean (SD) | 213.2 (71.4) | 2072.0 (720.0) | 9.65 (7.27, 12.81) |
| $C_{max}$, ng/ml, mean (SD) | 45.2 (15.0) | 240.2 (70.3) | 5.32 (4.19, 6.76) |
| $T_{max}$, h, median (range) | 2.00 (1.00-4.00) | 2.50 (1.00-8.06) | — |
| Apparent terminal $t_{1/2}$, h, mean (SD) | 2.52 (0.56) | 6.00 (1.27) | — |

$AUC_{0-\infty}$, area under the plasma concentration-time curve from time 0 to infinity;

$C_{max}$, maximum plasma concentration;

GCV, geometric coefficient of variation;

GM, geometric least-squares mean;

GMR, ratio of geometric least squares mean (ubrogepant + ketoconazole/ubrogepant);

PK, pharmacokinetic;

SD, standard deviation;

$t_{1/2}$, half-life;

$t_{max}$, time to maximum plasma concentration

Figure 4:
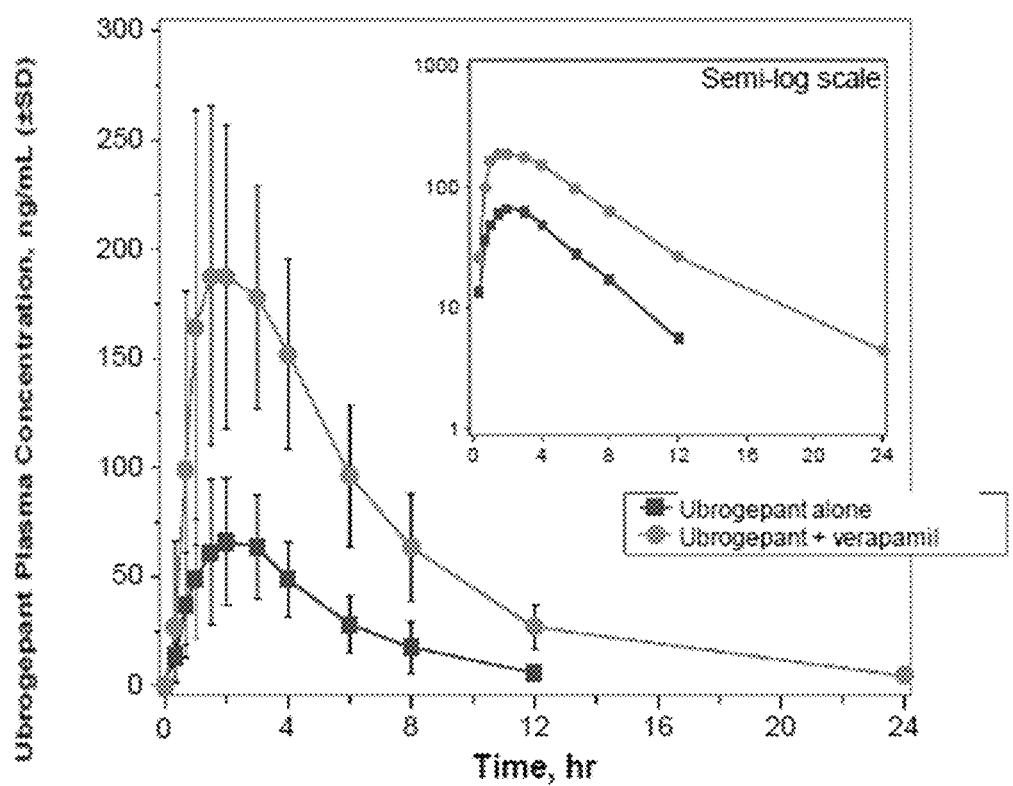
FIG. 4 shows plasma concentration-time profiles of single-dose ubrogepant 20 mg following administration alone and co-administered with multiple-dose verapamil 240 mg, a moderate CYP3A4 inhibitor.

The plasma concentration-time profiles of single-dose ubrogepant 20 mg following administration alone and co-administered with multiple-dose verapamil 240 mg, a moderate CYP3A4 inhibitor, are shown in FIG. 4. Moderate CYP3A4 inhibition with verapamil resulted in about 3.5-fold and 2.8-fold increase in $AUC_{inf}$ and $C_{max}$ of ubrogepant, respectively, relative to ubrogepant administered alone. Statistical comparisons of plasma pharmacokinetics of ubrogepant following administration of a single oral dose of 20 mg ubrogepant alone as compared to a single oral dose of 20 mg ubrogepant with multiple oral doses of 240 mg verapamil is provided in Table 9.

TABLE 9

Statistical Comparisons of Plasma Pharmacokinetics of Ubrogepant Following the Administration of a Single Oral Dose of 20 mg Ubrogepant Alone and Following Administration of a Single Oral Dose of 20 mg Ubrogepant with Multiple Oral Doses of 240 mg Verapamil

| Ubrogepant Pharmacokinetic Parameter | Ubrogepant Alone | | | Ubrogepant with Verapamil (test) | | | Ubrogepant with Verapamil/ Ubrogepant Alone | | Pseudo within subject |
|---|---|---|---|---|---|---|---|---|---|
| | N | AM | SD | N | AM | SD | GMR | 90% CI | % CV |
| $AUC_{0-\infty}$ | 12 | 213.2 | 71.4 | 12 | 742.0 | 212.7 | 3.52 | (3.32, 3.75) | 8.32 |
| $C_{max}$ (ng/mL) | 12 | 45.2 | 15.0 | 12 | 124.8 | 36.4 | 2.80 | (2.48, 3.15) | 16.26 |

TABLE 9-continued

Statistical Comparisons of Plasma Pharmacokinetics of Ubrogepant Following the Administration of a Single Oral Dose of 20 mg Ubrogepant Alone and Following Administration of a Single Oral Dose of 20 mg Ubrogepant with Multiple Oral Doses of 240 mg Verapamil

| Ubrogepant Pharmacokinetic Parameter | Ubrogepant Alone | | | Ubrogepant with Verapamil (test) | | | Ubrogepant with Verapamil/ Ubrogepant Alone | | Pseudo within subject |
|---|---|---|---|---|---|---|---|---|---|
| | N | AM | SD | N | AM | SD | GMR | 90% CI | % CV |
| $T_{max}$ (hr) | 12 | 2.00 | (1.00, 4.00) | 12 | 2.00 | (1.03, 4.00) | | | |
| Apparent terminal $t_{1/2}$ (hr) | 12 | 2.52 | 0.56 | 12 | 4.29 | 0.91 | | | |

Figure 5:
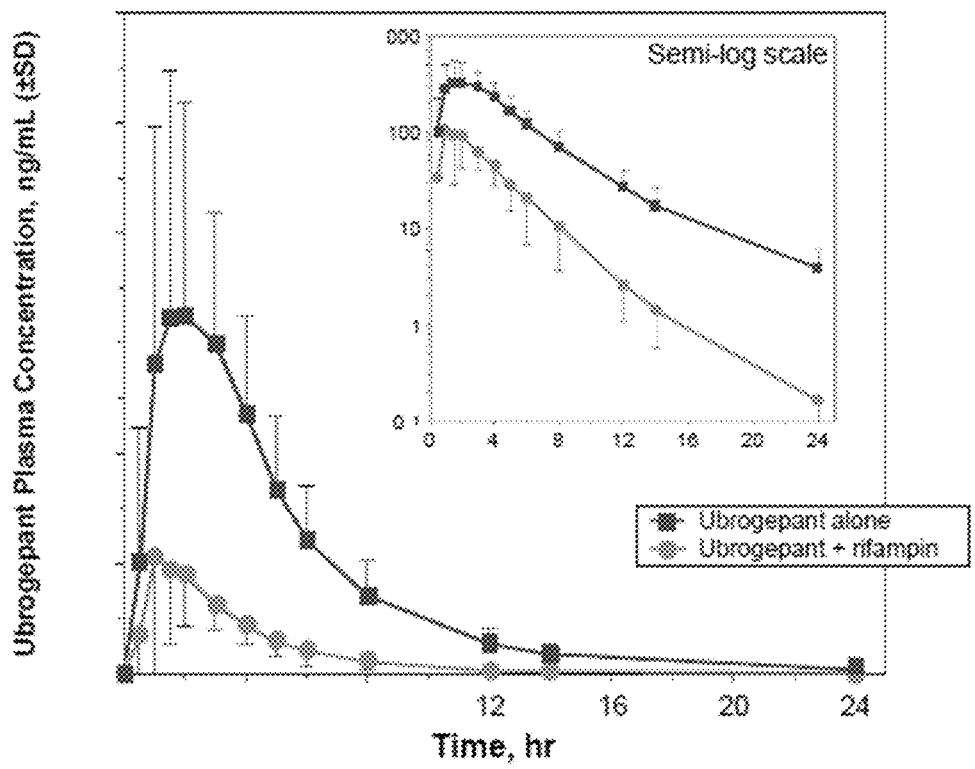
FIG. 5 shows the plasma concentration-time profiles of ubrogepant 100 mg alone and following co-administration with rifampin 600 mg, a strong CYP3A4 and P-gp inducer.

The plasma concentration-time profiles of ubrogepant 100 mg alone and following co-administration with rifampin 600 mg (a strong CYP3A4 and P-gp inducer) are shown in FIG. 5. Co-administration of ubrogepant with rifampin resulted in about 78% reduction in ubrogepant $AUC_{inf}$ and 69% reduction in $C_{max}$ compared to administration of ubrogepant alone. The median $t_{max}$ of ubrogepant was slightly shorter when coadministered with rifampin compared with ubrogepant administered alone (1.5 hours vs. 2.0 hours). Terminal $t_{1/2}$ of ubrogepant was shorter when coadministered with rifampin (3.0 hours) compared with ubrogepant administered alone (4.4 hours). The PK parameters of ubrogepant alone or co-administered with rifampin are summarized in Table 10.

TABLE 10

PK Parameters of Ubrogepant Alone or Coadministered with Rifampin

| PK Parameter | Ubrogepant | Ubrogepant + Rifampin |
|---|---|---|
| $AUC_{0-\infty}$ ng · h/mL, mean (SD) | 1908.31 (834.95) | 397.13 (144.28) |
| $AUC_{0-t}$ ng · h/mL, mean (SD) | 1883.29 (822.98) | 395.96 (144.28) |
| $C_{max}$, ng/ml, mean (SD) | 415.89 (197.55) | 136.07 (96.18) |
| $T_{max}$, h, median (range) | 2.00 (1.00-4.00) | 1.50 (0.50-6.00) |
| Apparent terminal $t_{1/2}$, h, mean (SD) | 4.36 (0.75) | 3.04 (0.64) |
| $V_z/F$ (L) | 390.13 ± 173.68 | 1238.68 ± 486.31 |
| CL/F (L/h) | 62.77 ± 28.33 | 282.87 ± 103.74 |

$AUC_{0-t}$ = area under the plasma concentration versus time curve from time 0 to time t;
$AUC_{0-\infty}$ = area under the plasma concentration versus time curve from time 0 to infinity;
CL/F = apparent total body clearance of drug from plasma after extravascular administration;
$C_{max}$ = maximum plasma drug concentration;
PK = pharmacokinetic(s);
SD = standard deviation;
$T_{max}$ = time of maximum plasma drug concentration;
$t_{1/2}$ = terminal elimination half-life;
$V_z/F$ = apparent volume of distribution during the terminal phase after extravascular administration.

Results from statistical comparisons including the ratio of geometric means and 90% CI are presented in Table 11. In the comparison of a single dose of ubrogepant 100 mg coadministered with multiple doses of rifampin 600 mg versus a single dose of ubrogepant 100 mg administered alone, ubrogepant $AUC_{0-t}$ and $AUC_{0-\infty}$ were 78% lower. Ubrogepant $C_{max}$ was 69% lower when coadministered with rifampin as compared to ubrogepant administered alone.

TABLE 11

Summary of Statistical Analysis Results of Plasma Ubrogepant Pharmacokinetic Parameters following Oral Administration of Rifampin 600 mg in Combination with Ubrogepant 100 mg (Test, n = 28) in Comparison with Ubrogepant 100 mg Administered Alone (Reference n = 30) in Healthy Adult Participants, PK Population.

| PK Parameter | Geometric LSM | | Ratio of Geometric Means | 90% Lower | 90% Upper |
|---|---|---|---|---|---|
| | Test | Reference | Test/Reference | CI | CI |
| $C_{max}$ (ng/ml) | 117.529 | 375.186 | 31.33 | 27.24 | 36.02 |
| $AUC_{0-t}$ (ng · h/mL) | 377.765 | 1722.896 | 21.93 | 19.86 | 24.21 |
| $AUC_{0-\infty}$ (ng · h/mL) | 379.033 | 1745.214 | 21.72 | 19.68 | 23.97 |

$AUC_{0-\infty}$ = area under the plasma concentration versus time curve from time 0 to infinity;
$AUC_{0-t}$ = area under the plasma concentration versus time curve from time 0 to time t;
CI = confidence interval;
$C_{max}$ = maximum plasma drug concentration;
LSM = least squares mean;
PK = pharmacokinetic(s).

In Study A, a single oral dose of ubrogepant appeared to be safe and generally well tolerated when coadministered with multiple doses of verapamil or ketoconazole in healthy adults. Eleven participants reported a total of 39 TEAEs. Nine TEAEs were considered treatment related, and all were related to verapamil only. Most TEAEs were mild in severity, and the most commonly reported TEAE was headache. One participant had a fatal SAE after dosing but before the follow-up visit (traffic accident) that was considered not related to study intervention. No other SAEs, deaths, or discontinuations due to a TEAE occurred in Study A. Additionally, no participants experienced elevations in serum transaminases or bilirubin greater than or equal to 2-fold ULN, and there were no treatment-related changes in laboratory values, vital signs, or ECG parameters.

In study B, a single oral dose of ubrogepant appeared to be safe and generally well tolerated when coadministered with multiple doses of rifampin. Six of thirty participants reported at least one TEAE during the trial, most commonly headache (4 participants, 13.3%). All TEAEs were considered to be treatment related, and all were mild in severity. No SAEs, deaths, or discontinuations for a TEAE occurred in Study B. Changes from baseline in laboratory values, vital signs, and ECG parameters were not clinically meaningful. A summary of adverse events is set forth in Tables 12 and 13.

TABLE 12

Study B-Adverse Events-Overall Summary (Safety Population)

| | Treatment A: Ubrogepant 100 mg (2 × 50 mg) under fasted conditions- single dose (N = 30) n (%) | Treatment B: Repeated doses of 600 mg rifampin (2 × 300 mg Rifadin oral capsules), once daily for 5 days on days 9 to 13 under fasted conditions (N = 30) n (%) | Treatment C: Co-administration of 600 mg rifampin with 100 mg ubrogepant on Day 14 under fasted conditions (N = 28) n (%) | Total[d] (N = 30) n (%) |
|---|---|---|---|---|
| TEAEs[a] | 4 (13.3) | 1 (3.3) | 2 (7.1) | 6 (20.0) |
| Treatment related TEAEs[a] | 4 (13.3) | 1 (3.3) | 2 (7.1) | 6 (20.0) |
| SAEs[b] | 0 | 0 | 0 | 0 |
| Deaths[b] | 0 | 0 | 0 | 0 |
| AEs leading to discontinuation[c] | 0 | 0 | 0 | 0 |

AEs = adverse events;
SAEs = serious adverse events;
TEAEs = treatment-emergent adverse events.
[a]Events that began or worsened on or after treatment date and within 30 days after the treatment end date.
[b]Events that occurred on or after the treatment start date and within 30 days after the treatment end date.
[c]Discontinuation event within treatment period + 30 days after treatment end date.
[d]Total = Participants who took any investigative product (counted only once)

TABLE 13

Study B-Overall summary of Adverse Events by Treatment and by System Organ Class and Preferred Term (Safety Population)

| System Organ Class[a] Preferred Term | Treatment A: Ubrogepant 100 mg (2 × 50 mg) under fasted conditions- single dose (N = 30) n (%) | Treatment B: Repeated doses of 600 mg rifampin (2 × 300 mg Rifadin oral capsules), once daily for 5 days on days 9 to 13 under fasted conditions (N = 30) n (%) | Treatment C: Co-administration of 600 mg rifampin with 100 mg ubrogepant on Day 14 under fasted conditions (N = 28) n (%) | Total[b] (N = 30) n (%) |
|---|---|---|---|---|
| Any AE | 4 (13.3) | 1 (3.3) | 2 (7.1) | 6 (20.0) |
| Gastro-intestinal Disorders | 2 (6.7) | 0 | 2 (7.1) | 4 (13.3) |
| Nausea | 0 | 0 | 2 (7.1) | 2 (6.7) |
| Dry Mouth | 1 (3.3) | 0 | 0 | 1 (3.3) |
| Flatulence | 1 (3.3) | 0 | 0 | 1 (3.3) |
| Nervous System Disorders | 2 (6.7) | 1 (3.3) | 1 (3.6) | 4 (13.3) |
| Headache | 2 (6.7) | 1 (3.3) | 1 (3.6) | 4 (13.3) |

AE = adverse event;
MedDRA = Medical Dictionary for Regulatory Activities;
n = number of participants who had the event;
N = number of participants in the safety population
[a]MedDRA version 20.0
[b]Total = participants who took any investigational product (counted only once)

Systemic exposure of single-dose ubrogepant was increased following coadministration with both verapamil and ketoconazole administered as multiple doses to reach maximal levels of CYP3A4 inhibition. A 3.5 fold increase in ubrogepant exposure ($AUC_{0-\infty}$) was seen with concomitant verapamil, a moderate CYP3A4 inhibitor. Based on these findings, dose modification of ubrogepant is recommended with coadministered with a moderate CYP3A4 inhibitor.

Ketoconazole dose (400 mg) and duration of dosing (administered daily for 2 days before ubrogepant administration) were selected to achieve maximal CYP3A4 inhibition. Exposure of ubrogepant ($AUC_{0-\infty}$) was more than 9 times higher following coadministration with the strong CYP3A4 and P-gp inhibitor ketoconazole. Concomitant use of ubrogepant with strong CYP3A4 inhibitors is contraindicated. The increased exposure of ubrogepant with concomitant verapamil or ketoconazole, together with the increased $t_{1/2}$, suggest interactions at both first-pass and systemic levels. CYP3A4 is also expressed in the gut wall, and selective inhibition or induction of gut enzymes could affect the bioavailability of orally administered ubrogepant.

In study B, the median ubrogepant $T_{max}$ was similar following administration of ubrogepant alone or in combination with rifampin (2 hours vs. 1.5 hours). The mean apparent terminal tin of ubrogepant was reduced by approximately one hour when ubrogepant was administered in combination with rifampin as compared to ubrogepant administered alone.

The $C_{max}$ and systemic exposure (AUC) of ubrogepant were significantly decreased following coadministration of ubrogepant and rifampin compared with ubrogepant administered alone. In particular, a decrease in ubrogepant exposure (78% decrease in $AUC_{0-\infty}$ and 69% decrease in $C_{max}$) was observed following coadministration with the strong CYP3A4 and P-gp inhibitor rifampin. This decrease in ubrogepant exposure is expected to reduce clinical efficacy, and the concomitant use of strong CYP3A4 inducers with ubrogepant should be avoided. Taken together, these findings suggest CYP3A4 and P-gp transport play important roles in the absorption and elimination of ubrogepant.

A single oral dose of ubrogepant appeared to be safe and generally well-tolerated when coadministered with multiple oral doses of verapamil, ketoconazole, or rifampin in healthy adults.

Example 3

The safety of ubrogepant was evaluated in 3,624 subjects who received at least one dose of ubrogepant. In two randomized, double-blind, placebo-controlled, Ph. 3 trials in adult patients with migraine [Study 1 (NCT02828020) and Study 2 (NCT02867709), a total of 1,439 patients received ubrogepant 50 mg or 100 mg. Of the ubrogepant-treated patients in these two studies, approximately 89% were female, 82% were white, 15% were Black, and 17% were of Hispanic or Latino ethnicity. The mean age at study entry was 41 years (range of 18-75 years).

Study 1 randomized patients to placebo (n=559) or Ubrelvy (ubrogepant) 50 mg (n=556) or 100 mg (n=557). Study 2 randomized patients to placebo (n=563) or Ubrelvy (ubrogepant) 50 mg (n=562). In all studies, patients were instructed to treat a migraine with moderate to severe headache pain intensity. A second dose of study medication (Ubrelvy/ubrogepant or placebo) or the patient's usual treatment for migraine, was allowed between 2 to 48 hours after the initial treatment for a non-responding or recurrent migraine headache. Up to 23% of patients were taking preventive medications for migraine at baseline. None of these patients were on concomitant preventive medication that act on the CGRP pathway.

The primary efficacy analyses were conducted in patients who treated a migraine with moderate to severe pain. The efficacy of UBRELVY (ubrogepant) was established by an effect on pain freedom at 2 hours post-dose and most bothersome symptom (MBS) freedom at 2 hours post-dose, compared with placebo, for Studies 1 and 2. Pain freedom was defined as a reduction of moderate or severe headache pain to no pain, and MBS freedom was defined as the absence of the self-identified MBS (i.e., photophobia, phonophobia, or nausea). Among patients who selected an MBS, the most commonly selected was photophobia (56%), followed by phonophobia (24%) and nausea (19%).

The migraine efficacy results for Studies 1 and 2 are shown in Table 14. Table 14 also presents the results of the analyses of the percentage of patients achieving pain relief at 2 hours (defined as a reduction in migraine pain from moderate or severe to mild or none) post-dose and the percentage of patients achieving sustained pain freedom between 2 to 24 hours post-dose.

TABLE 14

Migraine Efficacy Endpoints for Study 1 and Study 2

| | Study 1 | | | Study 2 | |
|---|---|---|---|---|---|
| | Ubrelvy (ubrogepant) 50 mg | Ubrelvy (ubrogepant) 100 mg | Placebo | Ubrelvy (ubrogepant) 50 mg | Placebo |
| Pain free at 2 hours | | | | | |
| N | 422 | 448 | 456 | 464 | 456 |
| % Responders | 19.2 | 21.2 | 11.8 | 21.8 | 14.3 |
| Difference from Placebo (%) | 7.4 | 9.4 | — | 7.5 | — |
| p value | 0.002 | <0.001 | — | 0.007 | — |
| Most Bothersome Symptom Free at 2 hours | | | | | |
| N | 420 | 448 | 454 | 465 | 456 |
| % Responders | 38.6 | 37.7 | 27.8 | 38.9 | 27.4 |
| Difference from Placebo (%) | 10.8 | 9.9 | — | 11.5 | — |
| p value | <0/001 | <0.001 | — | <0.001 | — |
| Pain Relief at 2 hours | | | | | |
| N | 422 | 448 | 456 | 464 | 456 |
| % Responders | 60.7 | 61.4 | 49.1 | 62.7 | 48.2 |
| p value | <0.001 | <0.001 | — | <0.001 | — |
| Sustained pain freedom at 2-24 hours | | | | | |
| N | 418 | 441 | 452 | 457 | 451 |
| % Responders | 12.7 | 15.4 | 8.6 | 14.4 | 8.2 |
| p value | *NS | 0.002 | — | 0.005 | — |

*Not Statistically Significant (NS)

In both studies, the percentage of patients achieving headache pain freedom and MBS freedom 2 hours post dose was significantly greater among patients receiving UBRELVY (ubrogepant) compared to those receiving placebo. The incidence of photophobia and phonophobia was reduced following administration of Ubrogepant at both doses (50 and 100 mg) as compared to placebo.

Figure 6:
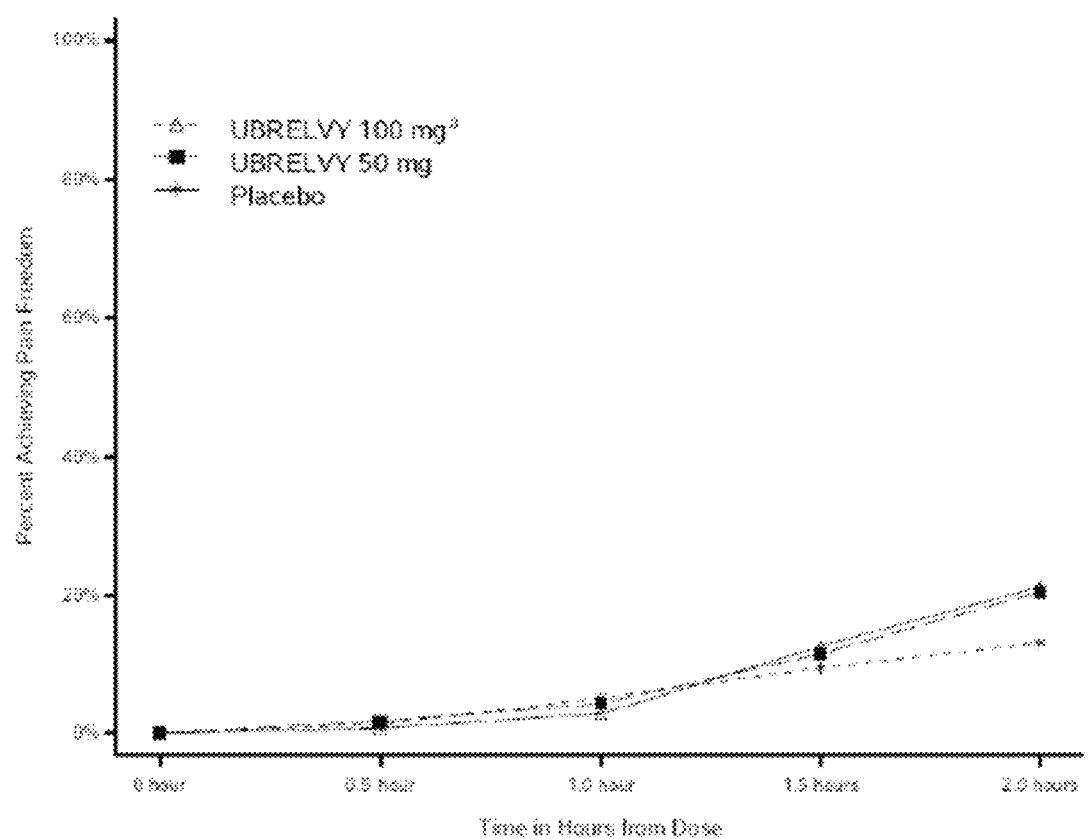
FIG. 6 shows the percentage of patients achieving pain freedom within 2 hours following treatment with ubrogepant in two clinical studies.
Figure 7:
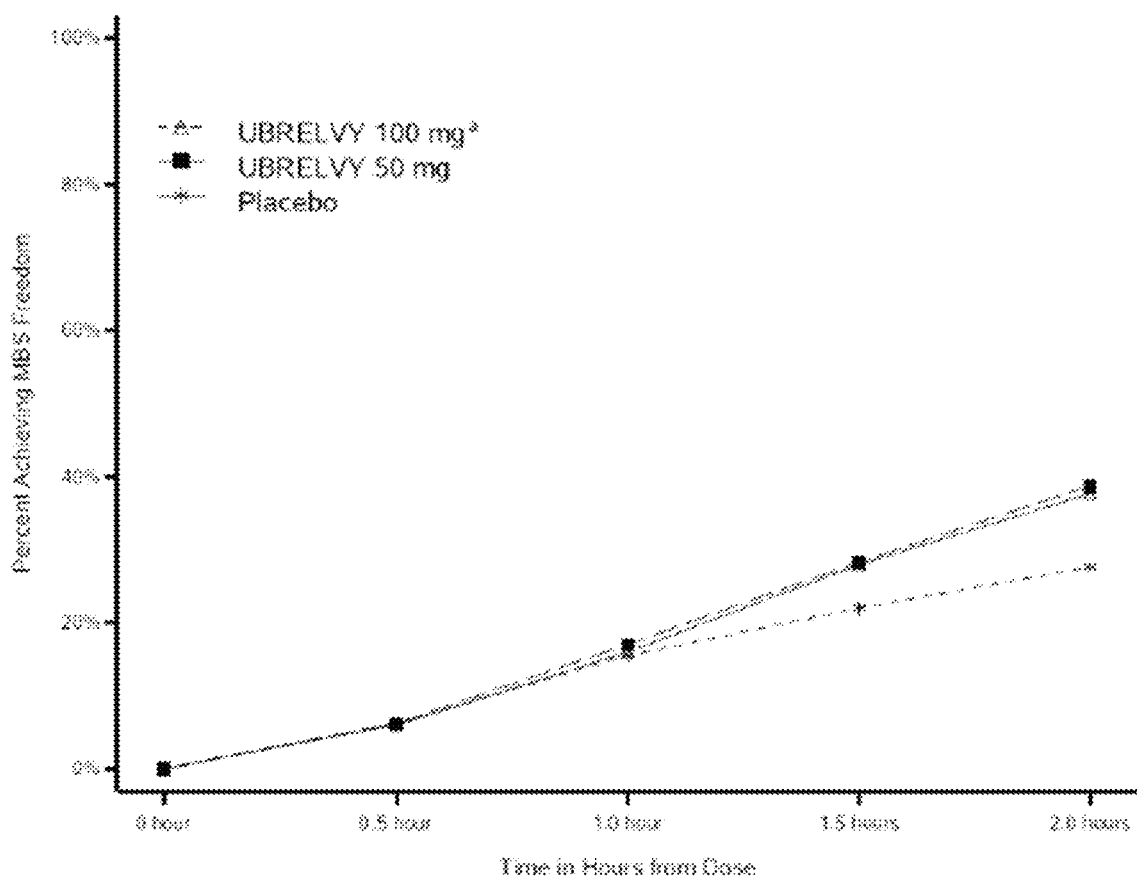
FIG. 7 shows the percentage of patients achieving Most Bothersome Symptom (MBS) freedom within 2 hours following treatment with ubrogepant in two clinical studies.

The percentage of patients achieving migraine pain freedom within 2 hours following treatment in studies 1 and 2 is shown in FIG. 6. The percentage of patients achieving MBS freedom within 2 hours in Studies 1 and 2 is shown in FIG. 7.

Long-term safety was assessed in 813 patients, dosing intermittently for up to 1 year in an open-label extension study. Patients were permitted to treat up to 8 migraines per month with ubrogepant. Of these 813 patients, 421 patients were exposed to 50 mg or 100 mg for at least 6 months, and 364 patients were exposed to these doses for at least one year, all of whom treated at least two migraine attacks per month, on average. In that study, 2.5% of patients were withdrawn from ubrogepant because of an adverse reaction. The most common adverse reaction resulting in discontinuation in the long-term safety study was nausea.

Adverse reactions in Studies 1 and 2 are shown in Table 15.

TABLE 15

Adverse Reactions Occurring in at least 2% and at a Frequency Greater than Placebo in Studies 1 and 2

| | Placebo (N = 984) % | Ubrogepant 50 mg (N = 954) % | Ubrogepant 100 mg (N = 485) % |
|---|---|---|---|
| Nausea | 2 | 2 | 4 |
| Somnolence (includes the adverse reaction-related terms sedation and fatigue) | 1 | 2 | 3 |
| Dry Mouth | 1 | <1 | 2 |

Example 4

ACHIEVE I (NCT02828020) and ACHIEVE II (NCT02867709) were pivotal, randomized, double-blind, placebo-controlled, single-attack trials where adults with migraine treated a qualifying migraine of moderate or severe pain intensity with ubrogepant (ACHIEVE 1: 50 mg or 100 mg; ACHIEVE II: 25 mg or 50 mg) or placebo. Participants who completed either trial could be randomized into a 52-week long-term extension (LTE) trial, treating up to 8 migraine attacks per month (any severity) with ubrogepant 100 mg, ubrogepant 50 mg, or usual care. Consistency of treatment was evaluated for pain freedom and pain relief at 2 hours for participants randomized to the ubrogepant 100 mg dose.

Therapeutic gain (TG) was calculated for the ACHIEVE trial and separately for the first 3 attacks of moderate/severe pain intensity treated in the long term extension trial, using placebo data from ACHIEVE. The TG ratio (TGR) was the TG from the LTE divided by the TG in the ACHIEVE trial multiplied by 100. Following consultation with regulatory agencies, a consistency threshold for the TGR of 50% or greater was used for this analysis.

Overall, 1254 participants were randomized in the long term extension trial, with 808 ubrogepant-treated participants included in the modified intent to treat (mITT) population for efficacy analyses (ubrogepant 10 mg, n=407). The rates for 2 hour pain freedom were 13.0% for the ACHIEVE placebo-treated attacks, 21.2% for ACHIEVE ubrogepant 100 mg-treated attacks, and 21.6% (mean across first 3 attacks) for ubrogepant 100 mg treated attack in the LTE trial. The rates for 2-hour pain relief were 48.7% for the ACHIEVE placebo treated attacks, 61.4% for ACHIEVE ubrogepant 100 mg treated attacks, and 68.0% (mean across first three attacks for ubrogepant 100 mg treated attacks in the LTE trial. The population-level TGRs were 104.9% for pain freedom and 152.0% for pain relief for the ubrogepant 100 mg dose group.

Using the TGR, ubrogepant 100 mg demonstrated population-level consistency of treatment effects from the ACHIEVE trials to the first three treated attacks with moderate or severe pain in the LTE trial.

Example 5

A Phase 1, single-center, single dose, open-label, randomized study included a 2-way crossover study to evaluate the effect of a high-fat meal on the oral bioavailability of the 100-mg Ubrelvy (ubrogepant) tablet formulation. The treatments were administered in 1 of 2 sequences in periods 1 and 2 with a washout period of at least 7 days between each treatment.

Eighteen healthy participants with a mean age of 28.4 years (range: 20 to 39 years) were enrolled. The majority of participants were male (14 of 18, 77.8%). Participants were predominantly black or African American (10 of 18, 55.6%), white (7 of 18, 38.9%); and one participant was Asian (5.6%). Mean (SD) weight was 75.99 (12824) kg and mean (SD) BMI was 25.03 (3.290) kg/m². Participants were randomly assigned one of two treatments in 1 of 2 sequences in Periods 1 and 2, with a washout period of at least 7 days between each study treatment.

TABLE 16

Study Sequences

| | Period 1 | Period 2 |
|---|---|---|
| Sequence I | Single dose of 100 mg ubrogepant tablet under fed conditions | Single dose of 100 mg ubrogepant tablet under fasted conditions |
| Sequence II | Single dose of 100 mg ubrogepant tablet under fasted conditions | Single dose of 100 mg ubrogepant tablet under fed conditions |

Participants in this part of the study had a total of 4 overnight stays per participant (Days −1, 1, 7, and 8). Participants were released from the study center on days 2 and 9, after the 24-hour postdose PK blood draw or after the EOT procedures were completed.

Participants were required to undergo a 10-hour overnight fast on Days-1 and 7 and were randomized to receive the 100-mg ubrogepant tablet formulation on Days 1 and 8, either under fasted conditions or within 30 minutes of starting a high-fat meal. For fed participants, the standardized high-fat (approximately 50% of total caloric content of the meal) and high-calorie (total of approximately 800 to 1000 calories) breakfast derived approximately 150 calories from protein, 250 calories from carbohydrates, and 500 to 600 calories from fat. An example of a high-fat breakfast meal would be 2 eggs fried in butter, 2 strips of bacon, 2 slices of toast with butter, 4 ounces of hash brown potatoes, and 8 ounces of whole milk. Substitutions in this meal could be made as long as the meal provided a similar number of calories from protein, carbohydrates, and fat and had a comparable meal volume and viscosity. Participants who were randomly assigned to receive ubrogepant under fed conditions were required to consume the high-fat, high-calorie breakfast in full. For all participants, no food was allowed for 4 hours following study treatment administration. Water was allowed as desired except for 1 hour before and 1 hour after study treatment administration.

Participants were given appropriate meals on check-in days (Days-1 and 7) based on their check-in time. On dosing days (Days 1 and 8), participants were given a standard lunch, dinner, and snack at approximately 1200, 1800 and 2100 hours, respectively.

While admitted in the study center, participants were provided with standardized low-fat (<20 g) meals, except during 1 period of this part of the study, when the high-fat, high-calorie meal was provided. Meals did not include any xanthine-containing compounds (i.e., caffeine), vegetables from the mustard green family, or grapefruit-containing foods or beverages.

The mean concentration-time profiles for plasma ubrogepant after single-dose administration of the 100 mg tablet under fed and fasted conditions are presented in FIG. 8 (linear scale) and FIG. 9 (semilogarithmic scale). The predose concentrations were below the limits of quantification in each study period for all participants, indicating sufficient washout between treatments. A summary of the PK parameters for ubrogepant after administration of the 100 mg tablet under fed and fasted conditions is presented in Table 17. Geometric mean extent of exposure to plasma ubrogepant (based on $AUC_{0-t}$ and $AUC_{0-inf}$) was similar after administration of the 100 mg tablet under fed and fasted conditions; however, geometric mean maximum exposure (based on $C_{max}$) was lower and the median $T_{max}$ was delayed (from 1 to 3 hours) under fed relative to fasted conditions. The mean tin was approximately 5 hours for both treatments.

TABLE 17

Geometric Mean (Geometric CV %) Plasma Ubrogepant Pharmacokinetic Parameters (PK Population)

| Parameter | Fed Ubrogepant 1 × 100 mg n = 17 | Fasted Ubrogepant 1 × 100 mg n = 17 |
|---|---|---|
| $AUC_{0-t}$ (h*ng/mL) | 1318.98 (25.0) | 1333.66 (34.9) |
| $AUC_{0-inf}$ (h*ng/mL) | 1344.27 (25.5) | 1359.25 (35.1) |
| $C_{max}$ (ng/mL) | 262.36 (34.4) | 334.37 (36.1) |
| $T_{max}^a$ (h) | 3.00 (0.50-4.00) | 1.00 (1.00-3.00) |
| $t_{1/2}$ (h) | 4.64 (11.1) | 4.99 (23.0) |

TABLE 17-continued

Geometric Mean (Geometric CV %) Plasma Ubrogepant Pharmacokinetic Parameters (PK Population)

| Parameter | Fed Ubrogepant 1 × 100 mg n = 17 | Fasted Ubrogepant 1 × 100 mg n = 17 |
|---|---|---|
| CL/F[b] (L/h) | 76.55 (24.1) | 77.29 (29.9) |
| $V_z$/F[b] (L) | 506.93 (22.7) | 535.64 (28.5) |

[a]Median (minimum – maximum) reported for $T_{max}$
[b]Arithmetic mean (CV %) reported for $t_{1/2}$, CL/F, and $V_z$/F A summary of the statistical comparisons of ubrogepant PK parameters after administration of the 100 mg tablet formulation under fed compared to fasted conditions is presented in Table 18.

TABLE 18

Summary of the Statistical Comparisons of Plasma Ubrogepant Pharmacokinetic Parameters: 100 mg Formulation under Fed vs. Fasted Conditions (PK Population)

| | Fed Ubrogepant 1 × 100 mg | | Fasted Ubrogepant 1 × 100 mg | | GMR[b, c] | 90% CI | | Intra-CV % | | Inter- |
|---|---|---|---|---|---|---|---|---|---|---|
| Parameter | N | GLSM[a] | N | GLSM[a] | (%) | Lower | Upper | Fed | Fasted | CV % |
| $AUC_{0-t}$ (h*ng/ml) | 17 | 1325.33 | 17 | 1340.31 | 98.88 | 92.613 | 105.576 | 10.91[d] | | 27.71 |
| $AUC_{0-inf}$ (h*ng/mL) | 17 | 1350.94 | 17 | 1366.14 | 98.89 | 92.808 | 105.366 | 10.56[d] | | 28.18 |
| $C_{max}$ (ng/mL) | 17 | 263.15 | 17 | 335.70 | 78.39 | 65.521 | 93.784 | 29.66 | 31.21% | 18.15 |
| $T_{max}$ (h) | 17 | 3.00 | 17 | 1.00 | 2.00 | | | | | |

[a]Median reported for $T_{max}$
[b]Median difference (test – reference) reported for $T_{max}$
[c]Results for $AUC_{0-t}$ and $AUC_{0-inf}$ provided from models without the repeated statement (allowing for variance of the response to vary across different treatments), as models did not converge
[d]Although reported in the Fed column, intra-CV % is estimated from the overall model and not for each treatment.

A high fat meal did not affect the extent of exposure to plasma ubrogepant (based on $AUC_{0-t}$ and $AUC_{0-inf}$) after administration of a single dose of the 100 mg tablet formulation; however, maximum exposure (based on $C_{max}$) was approximately 22% lower under fed versus fasted conditions. The time to peak exposure (based on $T_{max}$) after administration of the 100 mg tablet formulation was delayed under fed conditions (with a median difference [fed-fasted] of 2 hours); however, terminal elimination half-life was similar under fed and fasted conditions. Based on the GMR, food lowered maximum ubrogepant exposure by approximately 22% for the 100 mg tablet formulation. Additionally, the median difference (fed-fasted) in $T_{max}$ between treatments was 2 hours, suggesting food delayed time to peak exposure after administration of the 100 mg tablet formulation.

Example 6: Preparation of an Extrudate Comprising Kollidon® 64, TPGS and (S)-N-((3S,5S,6R)-6-methyl-2-oxo-5-phenyl-1-(2,2,2-trifluoroethyl)piperidin-3-yl)-2'-oxo-1',2',5,7-tetrahydrospiro[cyclopenta[b]pyridine-6,3'-pyrrolo[2,3-b]pyridine]-3-carboxamide (FIa-H, ubrogepant), a Tableting Formulation and Tablets Prepared Therefrom With reference to FIG. 11, extrudate comprising a water-soluble polymer matrix and dispersed therein API was prepared by:
(i) forming FIa-H/Matrix polymer pre-mix by dry-blending an amount of crystalline FIa-H and polyvinylpyrolidone/vinyl acetate copolymer (Matrix polymer) to provide a pre-mix having a weight ratio of API:Matrix polymer of 1:3.75;
(ii) feeding an amount of the API/Matrix pre-mix and an amount of molten alpha-tocopherol/propylene glycol succinate (TPGS) to provide a weight ratio of 19:1, API premix:TPGS into the extruder; and
(iii) maintaining the extruder apparatus at a barrel temperature, feed rate and screw speed that provides an extrudate comprising a solid solution of the API in a matrix (polyvinylpyrolidone-vinylacetate copolymer/TPGS) comprising about 20 wt % of the active API.

Accordingly, 1.318 Kg of FIa-H (compound of Formula Ia wherein all "R[b]" are —H) trihydrate was blended with 4.382 Kg of matrix polymer. TPGS (0.300 Kg) was melted and added to the blend of FIa-H and VA-64 in a high shear granulator. Blended API, VA-64, and TPGS was prepared in eight separate blending runs using a Diosna high shear granulator with a 6 L bowl, an impeller speed of 1000 rpm, a chopper speed of (600) rpm. In each run the blender was operated form 1 minute to mix FIa-H and the matrix polymer, then melted TPGS was added via pipette over 5 minutes of time maintaining the impeller and chopper speeds. After TPGS addition, the blend was mixed for an additional 1 minute maintaining the impeller and chopper speed.

The blend material was fed into a Thermo-Fischer 16 mm extruder while maintaining a product temperature of from about 146° C. to about 160° C., die pressure from about 14 bar to about 16 bar, a powder feed rate from 30-52 g/min., to provide 6.0 Kg of an extrudate of the present disclosure. This material was milled in a Fitzmill equipped with screen size 0 (0.027") and using the following operating conditions: an impeller speed of 2000-4500 prm, and impact: forward blade direction. The milled extrudate material was sized by passing it through a 600 micron screen providing a powder (extrudate intermediate) having a VMD of approx 195 microns when measured by QICPIC for use in preparing a blend for pressing into tablets (tableting blend).

A tableting blend (6 kg) was prepared using 3.6 kg of extrudate intermediate comprising the equivalent of 200 mg/g of 100% freebase FIa-H, 1.160 kg of mannitol SD 10, 0.600 kg of sodium chloride powder, 0.600 kg of cross carmellose sodium, 0.01500 kg of colloidal silica, 0.09000 kg of sodium stearyl fumarate, and 0.5798 kg of Avicel PH102. The blender speed was 25 rpm and the blender time was 5 minutes.

The tableting blend was sub-divided to 1.250 kg sub-parts and tablets corresponding to hardness ranges of 12-16 kP, 19-22 kP, and 24-28 kP were prepared by compressing aliquots from each portion of the tableting blend on a Korsch X1100 equipped with upper and lower tools with face drawing P14305-B, that is a plain oval tool measuring 14.68 mm×8.33 mm.

Tablets having a hardness in the range of 12 kP to 16 kP were tested in accordance with a test complying with USP 30 NF25 Chapt. 711, paddle stirrer apparatus equipped with USP 2 paddles, operated at 50 rpm, in 900 ml of simulated gastric fluid (pH 1.8) at 37° C., these tablets met the release profile goal of 90% FIa-F contained in the tablet dissolved in less than 20 minutes.

Example 7: Preparation of an Extrudate Comprising Kollidon® 64, TPGS, and (S)-N-((3S,5S,6R)-6-methyl-2-oxo-1-(2,2,2-trifluoroethyl)-5-(2,3,6-trifluorophenyl)piperidin-3-yl)-2'-oxo-1',2',5,7-tetrahydrospiro[cyclopenta[b]pyridine-6,3'-pyrrolo[2,3-b]pyridine]-3-carboxamide) (FIa-F, atogepant), a Tableting Formulation and Tablets Prepared Therefrom Using the general preparation shown in Example 6, 1.421 Kg of FIa-F (compound of Formula Ia wherein all "$R^b$" are —F) was blended with 4.320 Kg of matrix polymer in a 25.0 L Fielder Granulator, impeller speed set to 'fast', chopper speed set to 'high'. Into the granulator was added 0.300 Kg of TPGS over five minutes while maintaining the impeller and chopper speeds. This blended material was hot-melt extruded in a Thermo-Fisher 16 mm extruder set to provide a product temperature of 158° C., powder feed rate of 20 g/minute, and die pressure maintained at 2-4 Bar, yielding 4.52 Kg of extrudate.

The extrudate thus prepared (3.3 Kg) was milled with a Fitzmill, screen size 000 (0.20"), with impact blade set in the 'forward' direction and an impeller speed set to target 3000 rpm (2000 rpm to 6000 rpm). Milled extrudate was screened through a 600 micron screen yielding 3.01 Kg of screened extrudate. A portion of the screened material (3.0 Kg) was blended with sodium stearyl fumarate (0.05625 Kg), silicon dioxide (0.01875 Kg), microcrystalline cellulose (0.9750 Kg), Powdered Sodium Chloride (0.750 Kg) and mannitol (1.950 Kg) using a V-blender operating at 24 rpm.

Two aliquots of the tableting blend prepared above (1.957 Kg) were pressed into tablets corresponding to hardness ranges of 12 kP-18 kP and 20 kP-26 kP respectively, on a Korsch X1100 tableting press equipped with upper and lower tools with face drawing P10165-B (plain/plain) oval tool measuring 15.88 mm×8.81 mm with a tablet target weight of 652.2 mg.

Tablets were dissolved in a paddle stir dissolution apparatus using simulated gastric fluid at 37° C., paddle speed 50 rpm in a test complying with USP 30 NF25 Chapt. 711, these tablets met the release profile goal of 90% of FIa-F contained in the tablet dissolved in less than 20 minutes, and the disintegration goal of complete disintegration in less than 5 minutes when tested using a disintegration test complying with USP 31-NF26 Chapt. 701 in a standard disintegration testing apparatus (Pharamatron DT50) using aqueous HCl (pH 1.8) as a disintegration medium at 37° C. tested in aqueous HCl (pH 1.8) at 37° C.

Embodiments

1. A method for the acute treatment of migraine with or without aura in a patient with severe hepatic impairment, the method comprising administering a first dose of 50 mg of ubrogepant to a patient, wherein the patient has a Child-Pugh score of Child-Pugh Class C.
2. The method of claim 1, further comprising administering a second 50 mg dose of ubrogepant at least 2 hours after the first dose.
3. The method of claim 2, wherein the second dose is taken between 2 and 24 hours after the first dose.
4. A method for the acute treatment of migraine with or without aura in a patient having hepatic impairment, the method comprising:
   determining whether the patient has mild, moderate, or severe hepatic impairment; and
   if the patient has mild hepatic impairment, administering 50 mg or 100 mg ubrogepant to the patient;
   if the patient has moderate hepatic impairment, administering 50 mg or 100 mg ubrogepant to the patient; and
   if the patient has severe hepatic impairment, administering 50 mg ubrogepant to the patient.
5. The method according to claim 4, further comprising administering a second dose of ubrogepant to the patient at least 2 hours after the first dose, wherein
   if the patient has mild hepatic impairment, the second dose is 50 mg or 100 mg ubrogepant, and wherein the maximum dose in a 24 hour period is 200 mg;
   if the patient has moderate hepatic impairment, the second dose is 50 mg or 100 mg ubrogepant, and wherein the maximum dose in a 24 hour period is 200 mg; and
   if the patient has severe hepatic impairment, the second dose is 50 mg ubrogepant.
6. The method according to claim 5, wherein the second dose of ubrogepant is administered between 2 and 24 hours after the first dose of ubrogepant.
7. A method for the acute treatment of migraine with or without aura in a patient with severe renal impairment, the method comprising administering a first dose of 50 mg ubrogepant to a patient, wherein the patient's estimated creatinine clearance as determined using the Cockcroft-Gault equation is 15-29 mL/min.
8. The method of claim 7, further comprising administering a second dose of 50 mg of the ubrogepant at least 2 hours after the first dose.
9. The method of claim 8, wherein the second dose is taken between 2 and 24 hours after the first dose of ubrogepant.
10. A method for the acute treatment of migraine with or without aura in a patient having renal impairment, the method comprising:
    determining whether the patient has mild renal impairment, moderate renal impairment, severe renal impairment, or end-stage renal disease; and
    if the patient has mild renal impairment, administering 50 mg or 100 mg ubrogepant to the patient;
    if the patient has moderate renal impairment, administering 50 or 100 mg ubrogepant to the patient;
    if the patient has severe renal impairment, administering 50 mg ubrogepant to the patient; and
    if the patient has end-stage renal disease, avoiding administration of ubrogepant to the patient.
11. The method according to claim 10, further comprising administering a second dose of ubrogepant to the patient at least 2 hours after the first dose, wherein if the patient has mild renal impairment, the second dose is 50 mg or 100 mg ubrogepant, and wherein the maximum dose in a 24-hour period is 200 mg;
    if the patient has moderate renal impairment, the second dose is 50 mg or 100 mg ubrogepant, and wherein the maximum dose in a 24-hour period is 200 mg; and if the patient has severe renal impairment, the second dose is 50 mg ubrogepant.

12. A method for the acute treatment of migraine with or without aura in patients undergoing treatment with a moderate CYP3A4 inhibitor, the method comprising administering 50 mg ubrogepant to the patient undergoing treatment with the moderate CYP3A4 inhibitor.

13. The method of claim 12, wherein the maximum amount of ubrogepant administered to the patient in a 24-hour period is 50 mg.

14. The method of claim 12, wherein the moderate CYP3A4 inhibitor is verapamil.

15. The method of claim 12, wherein the moderate CYP3A4 inhibitor is administered before, concurrently with, or after ubrogepant.

16. A method for the acute treatment of migraine with or without aura in a patient in need of treatment, the method comprising administering a first dose of 50 mg or 100 mg ubrogepant to the patient, the method further comprising optionally administering a second dose of 50 mg or 100 mg ubrogepant to the patient at least 2 hours after the first 50 mg or 100 mg ubrogepant, wherein if the patient begins treatment with a moderate CYP3A4 inhibitor, the first dose of ubrogepant is adjusted to 50 mg and the optional second dose of ubrogepant is adjusted to 50 mg.

17. The method according to claim 16, wherein the moderate CYP3A4 inhibitor is verapamil.

18. A method for the acute treatment of migraine with or without aura in a patient undergoing treatment with a weak CYP3A4 inhibitor, the method comprising administering 50 mg ubrogepant to the patient undergoing treatment with a weak CYP3A4 inhibitor.

19. The method of claim 18, wherein a second 50 mg dose of ubrogepant is administered at least two hours after the first dose of ubrogepant.

20. The method of claim 19, wherein the second 50 mg dose of ubrogepant is administered between 2 and 24 hours after the first 50 mg dose of ubrogepant.

21. The method of claim 18, wherein the weak CYP3A4 inhibitor is administered before, concurrently with, or after ubrogepant.

22. A method for the acute treatment of migraine with or without aura in a patient in need of treatment, the method comprising administering a first dose of 50 mg or 100 mg ubrogepant to the patient, the method further comprising optionally administering a second dose of 50 mg or 100 mg ubrogepant to the patient at least 2 hours after the first 50 mg or 100 mg ubrogepant, wherein if the patient begins treatment with a weak CYP3A4 inhibitor, the first dose of ubrogepant is adjusted to 50 mg and the optional second dose of ubrogepant is adjusted to 50 mg.

23. A method for the acute treatment of migraine with or without aura in a patient undergoing treatment with a weak or moderate CYP3A4 inducer, the method comprising administering 100 mg ubrogepant to the patient undergoing treatment with the weak or moderate CYP3A4 inducer.

24. The method of claim 23, wherein a second dose of ubrogepant is administered at least 2 hours after the first dose of ubrogepant.

25. The method of claim 24, wherein the second dose is administered between 2 and 24 hours after the first dose of ubrogepant.

26. The method of claim 23, wherein the weak or moderate CYP3A4 inducer is administered before, concurrently with, or after ubrogepant.

27. A method for the acute treatment of migraine with or without aura in a patient in need of treatment, the method comprising administering a first dose of 50 mg or 100 mg ubrogepant to the patient, the method further comprising optionally administering a second dose of 50 mg or 100 mg ubrogepant to the patient at least 2 hours after the first 50 mg or 100 mg dose of ubrogepant, wherein if the patient begins treatment with a weak or moderate CYP3A4 inducer, the first dose of ubrogepant is adjusted to 100 mg and the optional second dose of ubrogepant is adjusted to 100 mg.

28. A method for the acute treatment of migraine with or without aura in a patient undergoing concurrent treatment with a BCRP and/or P-gp only inhibitor, the method comprising administering 50 mg ubrogepant to the patient undergoing treatment with a BCRP and/or P-gp only inhibitor.

29. The method of claim 28, wherein a second dose of 50 mg ubrogepant is administered at least 2 hours after the first dose of ubrogepant.

30. The method of claim 29, wherein the second dose of 50 mg ubrogepant is administered between 2-24 hours after the first dose of ubrogepant.

31. The method of claim 28, wherein ubrogepant is administered before, concurrently with, or after the BCRP and/or P-gp only inhibitor.

32. A method for the acute treatment of migraine with or without aura in a patient in need of treatment, the method comprising administering a first dose of 50 mg or 100 mg ubrogepant to the patient, the method further comprising optionally administering a second dose of 50 mg or 100 mg ubrogepant to the patient at least 2 hours after the first 50 mg or 100 mg dose of ubrogepant, wherein if the patient begins treatment with a BCRP and/or P-gp only inhibitor, the first dose of ubrogepant is adjusted to 50 mg and the optional second dose of ubrogepant is adjusted to 50 mg.

The invention claimed is:
1. A rapidly-disintegrating pharmaceutical tablet comprising:
 (a) an extrudate comprising:
  (i) a polymer matrix,
  (ii) a compound of Formula Ia,

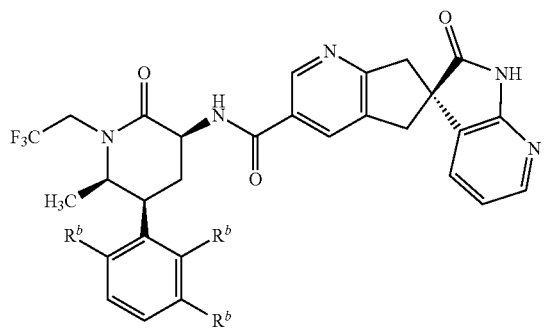

(Ia)

wherein each of R$^b$ is —H, and (iii) a dispersing agent, wherein the compound of Formula Ia is dispersed within the polymer matrix, and (b) a disintegration system;

wherein said tablet achieves complete disintegration in less than about 5 minutes in a tablet disintegration test complying with USP 31-NF26 Chapt. 701 using aqueous HCl at pH 1.8 at 37° C.

2. The tablet according to claim 1, wherein the disintegration system comprises croscarmellose sodium and sodium chloride.

3. The tablet according to claim 2, wherein croscarmellose sodium and sodium chloride are present in a 1:1 weight ratio.

4. The tablet according to claim 1, wherein the dispersing agent is selected from the group consisting of d-alpha-tocopheryl polyethyleneglycol succinate and polyethoxylated castor oil.

5. The tablet according to claim 4, wherein the dispersing agent is d-alpha-tocopheryl polyethyleneglycol succinate.

6. The tablet according to claim 3, wherein the dispersing agent is d-alpha-tocopheryl polyethyleneglycol succinate.

7. The tablet according to claim 5, wherein the dispersing agent is present in an amount of at least about 5 wt % of the extrudate.

8. The tablet according to claim 6, wherein the dispersing agent is present in an amount of at least about 5 wt % of the extrudate.

9. The tablet according to claim 1, wherein the polymer matrix comprises an excipient selected from the group consisting of polyvinylpyrrolidone-vinyl acetate copolymer and HPMCAS.

10. The tablet according to claim 8, wherein the polymer matrix comprises an excipient selected from the group consisting of polyvinylpyrrolidone-vinyl acetate copolymer and HPMCAS.

11. The tablet according to claim 1, wherein the extrudate comprises less than about 0.77 mole % degradation products of the compound of Formula Ia.

12. The tablet according to claim 9, wherein the extrudate comprises less than about 0.77 mole % degradation products of the compound of Formula Ia.

13. The tablet according to claim 1, wherein the tablet has a hardness of from about 12 kP to about 18 kP.

14. The tablet according to claim 8, wherein the tablet has a hardness of from about 12 kP to about 18 kP.

15. The tablet according to claim 1, wherein when said tablet is subjected to a dissolution test complying with USP 30 NF25 Chapt. 711, in a paddle-stirring apparatus equipped with USP 2 paddles, operated at 50 rpm, in 900 ml of simulated gastric fluid at pH 1.8 at 37° C. releases at least about 90% of the compound of Formula Ia contained therein in less than about 20 minutes.

16. The tablet according to claim 11, wherein when said tablet is subjected to a dissolution test complying with USP 30 NF25 Chapt. 711, in a paddle-stirring apparatus equipped with USP 2 paddles, operated at 50 rpm, in 900 ml of simulated gastric fluid at pH 1.8 at 37° C. releases at least about 90% of the compound of Formula Ia contained therein in less than about 20 minutes.

17. The tablet according to claim 1, wherein the tablet comprises about 50 mg of the compound of Formula Ia.

18. The tablet according to claim 8, wherein the tablet comprises about 50 mg of the compound of Formula Ia.

19. The tablet according to claim 10, wherein the tablet comprises about 50 mg of the compound of Formula Ia.

20. The tablet according to claim 1, wherein the tablet further comprises mannitol, colloidal silica, microcrystalline cellulose, and sodium stearyl fumarate.

21. A rapidly-disintegrating pharmaceutical tablet comprising:

(a) an extrudate comprising:

(i) a polymer matrix selected from the group consisting of polyvinylpyrrolidone vinyl acetate copolymer and HPMCAS, (ii) d-alpha-tocopheryl polyethyleneglycol succinate, (iii) a compound of Formula Ia,

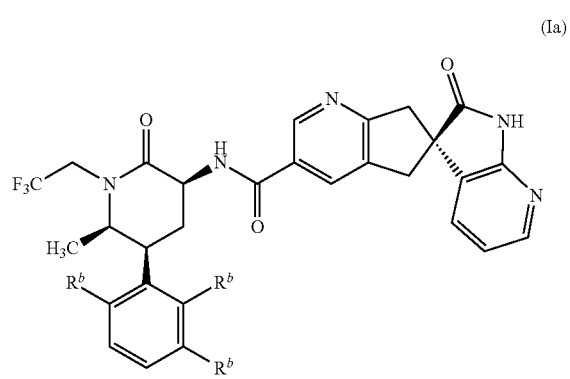

(Ia)

wherein each of R$^b$ is —H, and wherein the compound of Formula Ia is dispersed within the polymer matrix; and (b) a disintegration system comprising sodium chloride and croscarmellose sodium;

wherein said tablet achieves complete disintegration in less than about 5 minutes in a tablet disintegration test complying with USP 31-NF26 Chapt. 701 using aqueous HCl at pH 1.8 at 37° C.

22. The tablet according to claim 21, wherein the tablet further comprises mannitol.

23. The tablet according to claim 21, wherein the tablet further comprises colloidal silica.

24. The tablet according to claim 21, wherein the tablet further comprises sodium stearyl fumarate.

25. The tablet according to claim 21, wherein the tablet further comprises microcrystalline cellulose.

26. The tablet according to claim 21, wherein the tablet further comprises mannitol, colloidal silica, sodium stearyl fumarate, and microcrystalline cellulose.

27. The tablet according to claim 26, wherein the d-alpha-tocopheryl polyethyleneglycol succinate is present in an amount of at least about 5 wt % of the extrudate.

28. The tablet according to claim 27, wherein the sodium chloride and the croscarmellose sodium are present in a 1:1 weight ratio.

29. A rapidly-disintegrating pharmaceutical tablet comprising:

(a) an extrudate comprising:

(i) a polymer matrix, wherein the polymer matrix comprises an excipient selected from the group consisting of polyvinylpyrrolidone and HPMCAS, (ii) d-alpha-tocopheryl polyethyleneglycol succinate present in an amount of at least about 5 weight % of the extrudate,
(iii) a compound of Formula Ia,

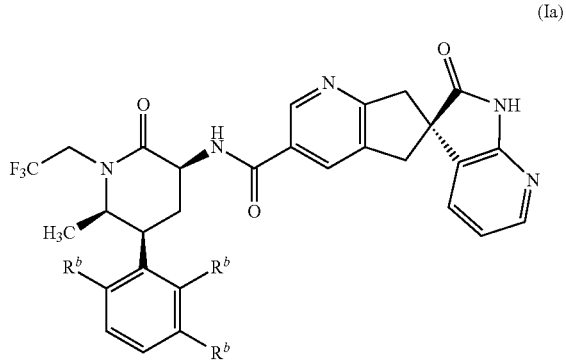

(Ia)

wherein each of $R^b$ is —H, and
wherein the compound of Formula Ia is dispersed within the polymer matrix;
(b) a disintegration system comprising sodium chloride and croscarmellose sodium in a 1:1 weight ratio;
(c) mannitol;
(d) colloidal silica;
(e) microcrystalline cellulose; and
(f) sodium stearyl fumarate;
wherein said tablet achieves complete disintegration in less than about 5 minutes in a tablet disintegration test complying with USP 31-NF26 Chapt. 701 using aqueous HCl at pH 1.8 at 37° C.

30. The tablet according to claim 29, wherein the tablet comprises about 50 mg of the compound of Formula Ia.

* * * * *